(12) United States Patent
Delaney et al.

(10) Patent No.: US 11,827,904 B2
(45) Date of Patent: Nov. 28, 2023

(54) MODIFIED STEM CELLS AND USES THEREOF

(71) Applicant: FRED HUTCHINSON CANCER CENTER, Seattle, WA (US)

(72) Inventors: Colleen Delaney, Seattle, WA (US); Stanley R. Riddell, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 0 days.

(21) Appl. No.: 15/570,209

(22) PCT Filed: Apr. 29, 2016

(86) PCT No.: PCT/US2016/030283
§ 371 (c)(1),
(2) Date: Oct. 27, 2017

(87) PCT Pub. No.: WO2016/176652
PCT Pub. Date: Nov. 3, 2016

(65) Prior Publication Data
US 2018/0142210 A1 May 24, 2018

Related U.S. Application Data

(60) Provisional application No. 62/154,573, filed on Apr. 29, 2015.

(51) Int. Cl.
*A61K 38/17* (2006.01)
*C12N 5/0789* (2010.01)
*C12N 15/86* (2006.01)
*C12N 15/85* (2006.01)

(52) U.S. Cl.
CPC ........... *C12N 5/0647* (2013.01); *C12N 15/85* (2013.01); *C12N 15/86* (2013.01); *C07K 2317/524* (2013.01); *C07K 2317/526* (2013.01); *C12N 2510/00* (2013.01); *C12N 2740/16043* (2013.01); *C12N 2740/16045* (2013.01); *C12N 2810/6081* (2013.01)

(58) Field of Classification Search
None
See application file for complete search history.

(56) References Cited

U.S. PATENT DOCUMENTS

| | | | |
|---|---|---|---|
| 5,283,173 A | 2/1994 | Fields et al. | |
| 5,420,032 A | 5/1995 | Marshall et al. | |
| 5,468,614 A | 11/1995 | Fields et al. | |
| 6,103,493 A * | 8/2000 | Skerra | C07K 14/36 435/252.3 |
| 6,291,158 B1 | 9/2001 | Winter et al. | |
| 6,291,161 B1 | 9/2001 | Lerner et al. | |
| 6,303,373 B1 | 10/2001 | Bogan et al. | |
| 6,410,319 B1 | 6/2002 | Raubitschek et al. | |
| 6,423,498 B1 | 7/2002 | Markland et al. | |
| 6,759,243 B2 | 7/2004 | Kranz et al. | |
| 6,833,252 B1 | 12/2004 | Dujon et al. | |
| 7,399,633 B2 | 7/2008 | Bernstein et al. | |
| 7,446,191 B2 | 11/2008 | Jensen | |
| 7,514,537 B2 | 4/2009 | Jensen | |
| 7,575,925 B2 | 8/2009 | Schmitt et al. | |
| 7,776,562 B2 | 8/2010 | Busch et al. | |
| 7,981,632 B2 * | 7/2011 | Schmidt | C07K 14/36 435/69.1 |
| 8,119,772 B2 | 2/2012 | Yang et al. | |
| 8,361,794 B2 | 1/2013 | Jakobsen | |
| 8,697,359 B1 | 4/2014 | Zhang | |
| 8,735,153 B2 * | 5/2014 | Wolffe | A61K 35/545 435/377 |
| 8,822,647 B2 | 9/2014 | Jensen | |
| 9,233,125 B2 | 1/2016 | Davila et al. | |
| 9,574,000 B2 | 2/2017 | Langermann et al. | |
| 10,494,434 B2 * | 12/2019 | Riddell | C12N 5/0637 |
| 2002/0034733 A1 | 3/2002 | Lohning | |
| 2002/0103345 A1 * | 8/2002 | Zhu | A61P 9/00 530/388.15 |
| 2003/0013192 A1 | 1/2003 | Laeng et al. | |
| 2003/0083474 A1 | 5/2003 | Schmidt | |
| 2003/0115614 A1 | 6/2003 | Kanda et al. | |
| 2003/0219876 A1 | 11/2003 | Ledbetter et al. | |
| 2004/0002092 A1 | 1/2004 | Arnould et al. | |
| 2005/0031600 A1 | 2/2005 | Mickle et al. | |
| 2005/0042225 A1 | 2/2005 | Serrero | |
| 2005/0227312 A1 | 10/2005 | Erdmann et al. | |

(Continued)

FOREIGN PATENT DOCUMENTS

| | | |
|---|---|---|
| EP | 1878744 A1 | 1/2008 |
| EP | 2871189 A1 | 5/2015 |

(Continued)

OTHER PUBLICATIONS

Oliveira et al Modification of Hematopoietic Stem/Progenitor Cells with CD19-Specific Chimeric Antigen Receptors as a Novel Approach for Cancer Immunotherapy Human Gene Therapy 24:824-839 (Oct. 2013).*

Abate-Daga et al., Review Article CAR models: next-generation CAR modifications for enhanced T-cell function Molecular Therapy—Oncolytics vol. 3, 2016, pp. 1-7<brclass="minwidth empty">.*

Jensen et al Design and implementation of adoptive therapy with chimeric antigen receptor-modified T cells Immunological Reviews 2014 vol. 257: 127-144.*

Stemberger et al., Novel Serial Positive Enrichment Technology Enables Clinical Multiparameter Cell Sorting PLoS ONE. 2012; pp. 1-11.*

(Continued)

*Primary Examiner* — Maria G Leavitt
(74) *Attorney, Agent, or Firm* — Seed IP Law Group LLP

(57) ABSTRACT

Stem cells are modified to express an extracellular component including a tag cassette. The tag cassette can be used to detect, enrich, isolate, activate, track, deplete, or eliminate modified cells. The cells can be administered before or following differentiation into a more committed cell type.

17 Claims, 11 Drawing Sheets

Specification includes a Sequence Listing.

(56) References Cited

U.S. PATENT DOCUMENTS

| | | |
|---|---|---|
| 2006/0078552 A1 | 4/2006 | Arnould et al. |
| 2006/0153826 A1 | 7/2006 | Arnould et al. |
| 2006/0206949 A1 | 9/2006 | Arnould et al. |
| 2007/0065431 A1 | 3/2007 | Coia et al. |
| 2007/0117128 A1 | 5/2007 | Smith et al. |
| 2007/0179092 A1 | 8/2007 | Ohta et al. |
| 2009/0042795 A1 | 2/2009 | Fernando et al. |
| 2009/0220501 A1 | 9/2009 | Fey et al. |
| 2010/0065818 A1 | 3/2010 | Kim et al. |
| 2010/0105136 A1 | 4/2010 | Carter et al. |
| 2010/0203021 A1 | 8/2010 | Goumans et al. |
| 2011/0189141 A1 | 8/2011 | Kieback et al. |
| 2011/0243972 A1 | 10/2011 | Jaffee |
| 2011/0301073 A1 | 12/2011 | Gregory et al. |
| 2012/0082667 A1 | 4/2012 | Yokoseki et al. |
| 2012/0107282 A1 | 5/2012 | Kim |
| 2012/0129229 A1 | 5/2012 | McBride et al. |
| 2012/0308530 A1 | 12/2012 | Hu et al. |
| 2012/0329714 A1 | 12/2012 | Shingo et al. |
| 2013/0115213 A1 | 5/2013 | Le Gall et al. |
| 2013/0243779 A1 | 9/2013 | Nagy et al. |
| 2013/0251690 A1 | 9/2013 | Van Dyke et al. |
| 2013/0315962 A1 | 11/2013 | Garcia-Bennett et al. |
| 2013/0330306 A1 | 12/2013 | Oh et al. |
| 2014/0068797 A1 | 3/2014 | Doudna et al. |
| 2014/0106449 A1 | 4/2014 | June et al. |
| 2014/0113370 A1 | 4/2014 | Camphausen et al. |
| 2014/0186843 A1 | 7/2014 | Zhang et al. |
| 2014/0234348 A1 | 8/2014 | Scholler et al. |
| 2014/0308256 A1 | 10/2014 | Lu et al. |
| 2014/0335059 A1 | 11/2014 | Pitaru et al. |
| 2014/0370598 A1 | 12/2014 | Colton et al. |
| 2015/0017718 A1 | 1/2015 | Nakatsuji et al. |
| 2015/0329640 A1 | 11/2015 | Finer |
| 2018/0355318 A1 | 12/2018 | Delaney et al. |
| 2020/0262894 A1 | 8/2020 | Liu et al. |
| 2021/0023132 A1 | 1/2021 | Liu et al. |

FOREIGN PATENT DOCUMENTS

| | | | |
|---|---|---|---|
| GB | 1320573.7 | * | 11/2013 |
| GB | 1410934.2 | * | 6/2014 |
| GB | 1415347.2 | * | 8/2014 |
| JP | 2017501702 A | | 1/2017 |
| JP | 2017507919 A | | 3/2017 |
| WO | WO 9942577 A2 | | 8/1999 |
| WO | WO 2006072620 A1 | | 7/2006 |
| WO | WO 2006095164 A1 | | 9/2006 |
| WO | WO 2007098934 A1 | | 9/2007 |
| WO | WO 2008045437 A2 | | 4/2008 |
| WO | WO 2009040338 A1 | | 4/2009 |
| WO | WO 2010040073 A1 | | 4/2010 |
| WO | WO 2010084158 A1 | | 7/2010 |
| WO | WO 2011041093 A1 | | 4/2011 |
| WO | WO 2011089527 A1 | | 7/2011 |
| WO | WO 2011147890 A1 | | 12/2011 |
| WO | WO 2012127464 A2 | | 9/2012 |
| WO | WO2012136231 | | 10/2012 |
| WO | WO 2013025779 A1 | | 2/2013 |
| WO | WO 2013044225 A1 | | 3/2013 |
| WO | WO 2013123061 A1 | | 8/2013 |
| WO | WO 2013124474 A2 | | 8/2013 |
| WO | WO 2014031687 A1 | | 2/2014 |
| WO | WO 2014190273 A1 | | 11/2014 |
| WO | WO2015075469 | * | 11/2014 |
| WO | WO2015066551 | | 5/2015 |
| WO | WO 2015067768 A1 | | 5/2015 |
| WO | WO 2015071474 A2 | | 5/2015 |
| WO | WO2015095895 A1 | | 6/2015 |
| WO | WO2016030691 | * | 3/2016 |
| WO | WO 2016040724 A1 | | 3/2016 |
| WO | WO 2016054638 A1 | | 4/2016 |
| WO | WO 2016134333 A1 | | 8/2016 |
| WO | WO 2016176651 A2 | | 11/2016 |
| WO | WO 2017021526 A1 | | 2/2017 |
| WO | WO 2018134691 A2 | | 7/2018 |

OTHER PUBLICATIONS

Jensen, et al., "Design and implementation of adoptive therapy with chimeric antigen receptor-modified T cells", NIH Public Access Author Manuscript.

Mummery, et al., "Differentiation of Human ES and iPS Cells to Cardiomyocytes: A Methods Overview," Circ Res. Jul. 20, 2012; 111(3): 344-358.

Invitiation to Pay Additional Fees dated Sep. 20, 2016 for International Application No. PCT/US16/30283.

Corrected International Preliminary Report on Patentability dated May 5, 2017 for International Application No. PCT/US16/30283.

Search Report and Written Opinion dated Nov. 28, 2016 for International Application No. PCT/US2016/030283.

Cartellieri, et al., "A Novel Ex Vivo Isolation and Expansion Procedure for Chimeric Antigen Receptor Engrafted Human T Cells," PLOS ONE, vol. 9, No. 4, 2014, 12 pages.

Extended Search Report dated Oct. 22, 2018 in European Application No. 16787280.3, 9 pages.

Kwon, et al., "Cellular Manipulation of Human Embryonic Stem Cells by TAT-PDXI Protein Transduction," Mol. Ther., vol. 12, No. 1, 2005, pp. 28-32.

Liu, et al., "Inclusion of Strep-tag II in design of antigen receptors for T-cell immunotherapy," Nat. Biol., vol. 34, No. 4, 2016, pp. 430-434.

Paszkiewicz, et al., "Targeted antibody-mediated depletion of murine CD19 CART cells permanently reverses B cell aplasia", J. Clin. Invest., vol. 126, No. 11, 2016, pp. 4262-4272.

Richard, et al., "Expansion of genetically modified primary humanhemopoietic cells using chemical inducers of dimerization," Blood, vol. 95, No. 2, 2000, pp. 430-436.

Chu, et al., "CS1-Specific Chimeric Antigen Receptor (CAR)-Engineered Natural Killer Cells Enhance In Vitro and In Vivo Anti tumor Activity Against Human Multiple Myeloma," Leukemia, vol. 28, No. 4, 2014, pp. 917-927.

Esser, et al., "NK cells engineered to express a GD2-specific antigen receptor display built-in ADCC-like activity against tumour cells of neuroectodermal origin," J. Cell. Mol. Med., vol. 16, No. 3, 2012, pp. 569-581.

Zuccolotto, et al., "PSMA-Specific CAR-Engineered T Cells Eradicate Disseminated Prostate Cancer in Preclinical Models," PLoS One, vol. 9, No. 10, 2014, 12 pages.

Office Action dated Jul. 20, 2020 for European Application No. 16787279.5, 4 pages.

Office Action dated Jun. 23, 2020 for Japanese Application No. 2017-556597, 6 pages.

Bejcek, et al., "Development and characterization of three recombinant single chain antibody fragments (scFvs) directed against the CD19 antigen," Cancer Res., vol. 55, No. 11, 1995, pp. 2346-2351.

Cooper, et al., "T-cell clones can be rendered specific for CD19: toward the selective augmentation of the graft-versus-B-lineage leukemia effect", Blood, vol. 101, No. 4, 2003, pp. 1637-1644.

Corrected International Preliminary Report on Patentability dated Jul. 14, 2017 for International Application No. PCT/US2016/030281.

De Oliveira, et al., "Modification of Hematopoietic Stem/Progenitor Cells with CD19-Specific Chimeric Antigen Receptors as a Novel Approach for Cancer Immunotherapy", Human Gene Therapy, vol. 24, No. 10, 2013, pp. 324-839.

The European Office Action dated May 15, 2020 for European Patent Application No. 16787280.3, a counterpart foreign application of the U.S. Appl. No. 15/570,209, 3 pages.

The Extended European Search Report dated Nov. 15, 2018 for European Patent Application No. 16787279.5, 12 pages.

Liu et al, "Design of Novel Multifunctional Chimeric Antigen Receptors (Tag/CARs) for Cancer Immunotherapy", retrieved on Mar. 17, 2015 at <<http://www.abstracts2view.comjasgctjview.php?nu=ASGCT14L1_428>>, May 22, 2014, 1 page.

(56) References Cited

OTHER PUBLICATIONS

Vloon et al, "Multifactorial T-cell Hypofunction That Is Reversible Can Limit the Efficacy of Chimeric Antigen Receptor-Transduced Human T cells in Solid Tumors", Clinical Cancer Research, vol. 20, No. 16, Jun. 11, 2014, pp. 4262-4273.
PCT Invitation to Pay Additional Fees dated Aug. 11, 2016 in International Application No. PCT/US2016/030281.
PCT International Preliminary Report on Patentability dated Jul. 14, 2017 for PCT Application No. PCT/US2016/030281.
Search Report and Written Opinion dated Oct. 17, 2016 for International Application No. PCT/US2016/030281.
Pezzutto, et al., "CD19 monoclonal antibody HD37 inhibits anti-immunoglobulin-induced B cell activation and proliferation," J. Immunol., vol. 138, No. 9, 1987, pp. 2793-2799.
Scholten, et al., "Codon modification of T cell receptors allows enhanced functional expression in transgenic human T cells," Clin. Immunol., vol. 119, No. 2, 2006, pp. 135-145.
Topfer et al, "DAP12-Based Activating Chimeric Antigen Receptor for NK Cell Tumor Immunotherapy", The Journal of Immunology. vol 194, No. 7, Mar. 4, 2015, pp. 3201-3212.
Wang et al, "A transgene-encoded cell surface polypeptide for selection, in vivo tracking, and ablation of engineered cells", blood, vol. 118, No. 5, Aug. 4, 2011, pp. 1255-1263.
Office Action dated Mar. 26, 2021 for European Patent Application No. 16787279.5, 5 pages.
Office Action dated Mar. 2, 2021 for Japanese Patent Application No. 2017-556597, 3 pages.
Alder et al., "Antibody responses of variable lymphocyte receptors in the lamprey," Nature Immunology 9(3):319-327, Mar. 2008.
Alexeev et al., "Recombinant DNA Technology in Emerging Modalities for Melanoma Immunotherapy," Chapter 6, in Duc (ed.), Melanoma—From Early Detection To Treatment, IntechOpen, 2013, pp. 175-196.
Altschul et al., "Gapped BLAST and PSI-BLAST: a new generation of protein database search programs," Nucleic Acids Research 25(17):3389-3402, Jul. 16, 1997.
Argast et al., "I-PpoI and I-CreI Homing Site Sequence Degeneracy Determined by Random Mutagenesis and Sequential in Vitro Enrichment," J. Mol. Biol. 280:345-353, 1998.
Ashworth et al., "Computational redesign of endonuclease DNA binding and cleavage specificity," Nature 441(7093):656-659 (2006).
Baral et al., "Experimental therapy of African trypanosomiasis with a nanobody-cojugated human trypanolytic factor," Nature Medicine 12(5):580-584, May 2006.
Barthelemy et al., "Comprehensive Analysis of the Factors Contributing to the Stability and Solubility of Autonomous Human VH Domains," The Journal of Biological Chemistry 283(6):3639-3654, Feb. 8, 2008.
Beavil et al., "α-Helical coiled-coil stalks in the low-affinity receptor for IgE (FcεRII/CD23) and related C-type lectins," Proc. Natl. Acad. Sci. USA 89:753-757, 1992.
Belfort et al., "Homing endonucleases: keeping the house in order," Nucleic Acids Research 25(17):3379-3388, 1997.
Besser et al., "Clinical Responses in a Phase II Study Using Adoptive Transfer of Short-term Cultured Tumor Infiltration Lymphocytes in Metastatic Melanoma Patients," Clinical Cancer Research 16(9):2646-2655, 2010. (11 pages).
Beste et al., "Small antibody-like proteins with prescribed ligand specificities derived from the lipocalin fold," Proc. Natl. Acad. Sci. USA 96:1898-1903, 1999.
Binz et al., "Designing Repeat Proteins: Well-expressed, Soluble and Stable Proteins from Combinatorial Libraries of Consensus Ankyrin Repeat Proteins," J. Mol. Biol. 332(2):489-503, 2003.
Binz et al., "Engineering novel binding proteins from nonimmunoglobulin domains," Nat. Biotechnol. 23(10): 1257-1268, 2005.
Binz et al., "High-affinity binders selected from designed ankyrin repeat protein libraries," Nat. Biotechnol. 22(5):575-582, 2004.
Boersma et al., "DARPins and other repeat protein scaffolds: advances in engineering and applications," Current Opinion in Biotechnology 22:849-857, 2011.

Bowdish et al., "Conserved domains of the class A scavenger receptors: evolution and function," Immunological Reviews 277:19-31, 2009.
Bowerman et al., "Engineering the Binding Properties of the T Cell Receptor: Peptide:MHC Ternary Complex that Governs T Cell Activity," Mol Immunol. 46(15):3000-3008, Sep. 2009.
Boyington et al., "Structure of CD94 Reveals a Novel C-Type Lectin Fold: Implications for the NK Cell-Associated CD94/NKG2 Receptors," Immunity 10:75-82, 1999.
Brentjens et al., "CD19-targeted T cells rapidly induce molecular remissions in adults with chemotherapy-refractory acute lymphoblastic leukemia," Sci Transl Med. 5(177):177ra38, Mar. 20, 2013. (19 pages).
Brentjens et al., "Genetically Targeted T Cells Eradicate Systemic Acute Lymphoblastic Leukemia Xenografts," Clin Cancer Res 13(18):5426-5435, Sep. 15, 2007. (11 pages).
Brinkmann et al., "The making of bispecific antibodies," MABS 9(2):182-212, 2017.
Capon et al., "Designing CD4 immunoadhesins for AIDS therapy," Nature 337:525-531, 1989.
Chao, "Calign: aligning sequences with restricted affine gap penalties," Bioinformatics 15(4): 298-304 (1999).
Chen et al., "Fusion protein linkers: Property, design and functionality," Advanced Drug Delivery Reviews 65:1357-1369, 2013.
Chevalier et al., "Design, Activity, and Structure of a Highly Specific Artificial Endonuclease," Molecular Cell 10:895-905, Oct. 2002.
Chothia et al., "The outline structure of the T-cell αβ receptor," The EMBO Journal 7(12): 3745-3755, 1988. (11 pages).
Clark, Jr. et al., "The Histogenesis and Biologic Behavior of Primary Human Malignant Melanomas of the Skin," Cancer Research 29:705-726, 1969. (23 pages).
Coiffier et al., "Chop Chemotherapy Plus Rituximab Compared With Chop Alone in Elderly Patients With Diffuse Large-B-Cell Lymphoma," N Engl J Med 346(4):235-242, Jan. 24, 2002.
Cole et al., "CD8: Adhesion Molecule, Co-Receptor and Immuno-Modulator," Cellular & Molecular Immunology 1(2):81-88, Apr. 2004. (8 pages).
Cortajarena et al., "Designed TPR Modules as Novel Anticancer Agents," ACS Chem. Biol. 3(3): 161-166, 2008.
Cortez-Retamozo et al., "Efficient Cancer Therapy with a Nanobody-Based Conjugate," Cancer Research 64:2853-2857, Apr. 15, 2004.
Dangaj et al., "Novel Recombinant Human B7-H4 Antibodies Overcome Tumoral Immune Escape to Potentiate T-Cell Antitumor Responses," Cancer Res 73(15):4820-4829, Aug. 1, 2013. (10 pages).
Darcy et al., "Expression in cytotoxic T lymphocytes of a single-chain anti-carcinoembryonic antigen antibody. Redirected Fas ligand-mediated lysis of colon carcinoma," Eur. J. Immunol. 28:1663-1672, 1998.
Desjarlais et al., "Use of a zinc-finger consensus sequence framework and specificity rules to design specific DNA binding proteins," Proc. Natl. Acad. Sci. USA 90:2256-2260, Mar. 1993. (5 pages).
Dossett et al., "Adoptive Immunotherapy of Disseminated Leukemia With TCR-transduced, CD8+ T Cells Expressing a Known Endogenous TCR," Molecular Therapy 17(4): 742-749, Apr. 2009. (8 pages).
Dotti et al., "Design and Development of Therapies using Chimeric Antigen Receptor-Expressing T cells," Immunol. Rev. 257(1): 107-126, 2014. (35 pages).
Dudley et al., "Cancer Regression and Autoimmunity in Patients After Clonal Repopulation with Antitumor Lymphocytes," Science 298(5594):850-854, 2002. (10 pages).
Dujon et al., "Mobile introns: definition of terms and recommended nomenclature," Gene 82:115-118, 1989.
Ebersbach et al., "Affilin-Novel Binding Molecules Based On Human γ-B-Crystallin, an All γ-Sheet Protein," J. Mol. Biol. 372(1): 172-185, 2007.
Engels et al., "Retroviral Vectors for High-Level Transgene Expression in T Lymphocytes," Human Gene Therapy 14:1155-1168, Aug. 10, 2003.

(56) References Cited

OTHER PUBLICATIONS

Epinat et al., "A novel engineered meganuclease induces homologous recombination in yeast and mammalian cells," *Nucleic Acids Research* 31(11):2952-2962, 2003. (11 pages).
Figdor et al., "C-Type Lectin Receptors on Dendritic Cells and Langerhans Cells," Nature Reviews Immunology 2:77-84, 2002. (9 pages).
Floros et al., "Anticancer Cytokines: Biology and Clinical Effects of IFN-α2, IL-2, IL-15, IL-21, and IL-12," *Semin Oncol.* 42(4):539-548, Aug. 2015. (HHS Public Access, Author Manuscript, available in PMC Aug. 1, 2016) (17 pages).
Frecha et al., "Advances in the Field of Lentivector-based Transduction of T and B Lymphocytes for Gene Therapy," Molecular Therapy 18(10): 1748-1757, Oct. 2010.
Friese et al., "In vivo Imaging with Antibodies and Engineered Fragments," Mol Immunol. 67(2 0 0): 142-152, Oct. 2015.
Gao et al., "Molecular interactions of coreceptor CD8 and MHC class I: the molecular basis for functional coordination with the T-cell receptor," *Immunology Today* 21(12):630- 636, Dec. 2000.
Genosys Biotechnologies, Inc., "Strep-tag: Production of Recombinant Proteins," Product Brochure, Jul. 1998, 32 pages.
Geurts et al., "Gene Transfer into Genomes of Human Cells by the *Sleeping Beauty* Transposon System," *Molecular Therapy* 8(1): 108-117, Jul. 2003.
Ghahroudi et al., "Selection and identification of single domain antibody fragments from camel heavy-chain antibodies," *FEBS Letters* 414:521-526, 1997.
Gimble et al., "Substrate Recognition and Induced DNA Distortion by the PI-SceI Endonuclease, an Enzyme Generated by Protein Splicing," *J. Mol. Biol.* 263: 163-180, 1996. (18 pages).
Green et al., "Mitochondria and Apoptosis," *Science* 281: 1309-1312, Aug. 28, 1998.
Guest et al., "The Role of Extracellular Spacer Regions in the Optimal Design of Chimeric Immune Receptors," *J Immunother* 28(3):203-211, May/Jun. 2005.
Hackel et al., "Picomolar Affinity Fibronectin Domains Engineered Utilizing Loop Length Diversity, Recursive Mutagenesis, and Loop Shuffling," J. Mol. Biol. 381(5):1238-1252, 2008. (27 pages).
Hamers-Casterman et al., "Naturally occurring antibodies devoid of light chains," Nature 363(6428):446-448, 1993.
Harris et al., "Adoptive T Cell Therapies: A Comparison of T Cell Receptors and Chimeric Antigen Receptors," *Trends Pharmacol Sci*. 37(3):220-230, Mar. 2016.
Haso et al., "Anti-CD22-chimeric antigen receptors targeting B-cell precursor acute lymphoblastic leukemia," *Blood* 121(7):1165-1174, Feb. 14, 2013.
Herrin et al., "Structure and specificity of lamprey monoclonal antibodies," *PNAS* 105(6): 2040-2045, Feb. 12, 2008.
Hoet et al., "Generation of high-affinity human antibodies by combining donor-derived and synthetic complementarity-determining-region diversity," Nature Biotechnology 23(3):344-348, 2005.
Huang et al., "Scorpion-Toxin Mimics of CD4 in Complex with Human Immunodeficiency Virus gp120: Crystal Structures, Molecular Mimicry, and Neutralization Breadth," Structure 13(5):755-768, 2005.
Hudecek et al., "The non-signaling extracellular spacer domain of chimeric antigen receptors is decisive for in vivo antitumor activity," Cancer Immunol. Res. 3(2): 125-135, 2015. (20 pages).
James et al., "Antigen sensitivity of CD22-specific chimeric T cell receptors is modulated by target epitope distance from the cell membrane," *J Immunol*. 180(10): 7028-7038, May 15, 2008.
Janeway, Jr. et al., *Immunobiology: The Immune System in Health and Disease, 3rd Ed.*, Current Biology Ltd/Garland Publishing Inc, 1997, Chapter 3, "Structure of the Antibody Molecule and Immunoglobulin Genes, " pp. 3:1-3:11.
Jasin, "Genetic manipulation of genomes with rare-cutting endonucleases," *TIG* 12(6):224-228, Jun. 1996.
Jespers et al., "Aggregation-resistant domain antibodies selected on phage by heat denaturation," *Nature Biotechnology* 22(9): 1161-1165, Sep. 2004.

Jinek et al., "A programmable dual RNA-guided DNA endonuclease in adaptive bacterial immunity," *Science* 337(6096):816-821, Aug. 17, 2012. (HHMI Public Access, Author Manuscript, available in PMC Dec. 7, 2018) (14 pages).
Jolly, "Emerging Viral Vectors," in Friedmann (ed.), The Development of Human Gene Therapy, Cold Spring Harbor Laboratory Press, New York, 1999, pp. 209-240.
Jores et al., "Resolution of hypervariable regions in T-cell receptor β chains by a modified Wu-Kabat index of amino acid diversity," *Proc. Natl. Acad. Sci. USA* 87:9138-9142, Dec. 1990. (5 pages).
June, "Adoptive T cell therapy for cancer in the clinic," The Journal of Clinical Investigation 117(6): 1466-1476, 2007.
Kalos et al., "T Cells with Chimeric Antigen Receptors Have Potent Antitumor Effects and Can Establish Memory in Patients with Advanced Leukemia," *Sci Transl Med*. 3(95): 95ra73, 21 pages, Aug. 10, 2011.
Kim et al., "High Cleavage Efficiency of a 2A Peptide Derived from Porcine Teschovirus-1 in Human Cell Lines, Zebrafish and Mice," *PLoS One* 6(4):e318556, Apr. 2011. (8 pages).
Kitchen et al., "Engineering Antigen-Specific T Cells from Genetically Modified Human Hematopoietic Stem Cells in Immunodeficient Mice," PLoS ONE 4(12):e8208, 2009. (9 pages).
Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor," Journal of Clinical Oncology 33(6):540-549, Feb. 20, 2015.
Kowolik et al., "CD28 Costimulation Provided through a CD19-Specific Chimeric Antigen Receptor Enhances In vivo Persistence and Antitumor Efficacy of Adoptively Transferred T Cells," *Cancer Res* 66(22): 10995-11004 (2006).
Krisky et al., "Development of herpes simplex virus replication-defective multigene vectors for combination gene therapy applications," Gene Therapy 5:1517-1530, 1998.
Kuball et al., "Facilitating matched pairing and expression of TCR chains introduced into human T cells," Blood 109(6): 2331-2338, Mar. 15, 2007.
Lake et al., "Construction and binding analysis of recombinant single-chain TCR derived from tumor-infiltrating lymphocytes and a cytotoxic T lymphocyte clone directed against MAGE-1," *International Immunology* 11(5): 745-751, 1999.
Ledbetter et al., "CD28 Ligation in T-Cell Activation: Evidence for Two Signal Transduction Pathways," *Blood* 75(7): 1531-1539, 1990. (10 Pages).
Lee et al., "T cells expressing CD19 chimeric antigen receptors for acute lymphoblastic leukaemia in children and young adults: a phase 1 dose-escalation trial," The Lancet 385:517-528, Feb. 7, 2015.
Leen et al., "Improving T Cell Therapy for Cancer," *Annu. Rev. Immunol*. 25:243-265, 2007. (26 pages).
Lefranc et al., "IMGT unique numbering for immunoglobulin and T cell receptor variable domains and Ig superfamily V-like domains," *Developmental and Comparative Immunology* 27:55-77, 2003. (23 pages).
Liu et al., "Selective inhibition of IDO1 effectively regulates mediators of antitumor immunity," *Blood* 115(17):3520-3530, Apr. 29, 2010. (11 pages).
Living Pharma, Personalized CAR T Cell TherapyTM, URL=https://livingpharma.com/technology, 2022. (2 pages).
Luo et al., "Development of genetically engineered CD4+ and CD8+ T cells expressing TCRs specific for a M. *tuberculosis* 38-kDa antigen," *J. Mol. Med*. 89:903-913, 2011.
Madhurantakam et al., "Structure-based optimization of designed Armadillo-repeat proteins," *Protein Science* 21:1015-1028, 2012.
Main et al., "Design of Stable α-Helical Arrays from an Idealized TPR Motif," Structure 11:497-508, 2003.
Martin et al., "Rational design of a CD4 mimic that inhibits HIV-1 entry and exposes cryptic neutralization epitopes," Nat. Biotechnol. 21(1):71-76, 2003.
Masters et al., "Clinical Cancer Advances 2015: Annual Report on Progress Against Cancer From the American Society of Clinical Oncology," *Journal of Clinical Oncology* 33(7):786-809, Mar. 1, 2015.

(56) References Cited

OTHER PUBLICATIONS

Mautino et al., "Abstract 491: NLG919, a novel indoleamine-2,3-dioxygenase (IDO)-pathway inhibitor drug candidate for cancer therapy," Proceedings: AACR 104th Annual Meeting 2013, Washington, DC, Apr. 6-10, 2013. (4 pages).
Maynard et al., "High-level bacterial secretion of single-chain αβ T-cell receptors," J. Immunol. Methods 306(1-2):51-67, 2005.
Meyer et al., "Click Chemistry and Radiochemistry: The First 10 Years," Bioconjug Chem. 27(12): 2791-2807, Dec. 21, 2016.
Moek et al., "Theranostics Using Antibodies and Antibody-Related Therapeutics," J Nucl Med 58:83S-90S, 2017.
Molloy et al., "Soluble T cell receptors: novel immunotherapies," Curr. Opin. Pharmacol. 5(4): 438-443, 2005.
Morgan et al., "Cancer Regression in Patients After Transfer of Genetically Engineered Lymphocytes," *Science* 314(5796): 126-129, 2006. (10 pages).
Morgan et al., "Case Report of a Serious Adverse Event Following the Administration of T Cells Transduced With a Chimeric Antigen Receptor Recognizing *ERBB2*," *Molecular Therapy* 18(4): 843-851, Apr. 2010.
Mátés et al., "Molecular evolution of a novel hyperactive *Sleeping Beauty* transposase enables robust stable gene transfer in vertebrates," *Nature Genetics, Advance Online Publication*, May 3, 2009. (33 pages).
Nareshkumar et al., "Current ADC Linker Chemistry," Pharm Res 32:3526-3540, 2015.
Nguyen et al., "Heavy-chain antibodies in *Camelidae*; a case of evolutionary innovation," *Immunogenetics* 54:39-47, 2002.
Nguyen et al., "Identification of a murine CD28 dileucine motif that suppresses single-chain chimeric T-cell receptor expression and function," Blood 102(13):4320-4325, Dec. 15, 2003.
Nguyen et al., "The Specific Variable Domain of Camel Heavy-chain Antibodies is Encoded in the Germline," *J. Mol. Biol.* 275:413-418, 1998.
Nord et al., "A combinatorial library of an α-helical bacterial receptor domain," Protein Eng. 8(6): 601-608, 1995.
Nord et al., "Binding proteins selected from combinatorial libraries of an α-helical bacterial receptor domain," Nat. Biotechnol. 15(8): 772-777, 1997.
Nord et al., "Recombinant human factor VIII-specific affinity ligands selected from phage-displayed combinatorial libraries of protein A," Eur. J. Biochem. 268(15):4269-4277, 2001.
Parker et al., "Antibody mimics based on human fibronectin type three domain engineered for thermostability and high-affinity binding to vascular endothelial growth factor receptor two," Protein Eng. Des. Sel. 18(9):435-444, 2005.
Parslow et al., "Antibody-Drug Conjugates for Cancer Therapy," *Biomedicines* 4(14), 2016. (17 pages).
Patel et al., "Impact of chimeric immune receptor extracellular protein domains on T cell function," Gene Therapy 6:412-419, 1999.
Penman et al., "The Type I and Type II Bovine Scavenger Receptors Expressed in Chinese Hamster Ovary Cells Are Trimeric Proteins with Collagenous Triple Helical Domains Comprising Noncovalently Associated Monomers and Cys[83]-Disulfide-Linked Dimers," J. Biol. Chem. 266(35): 23985-23993, 1991.
Perler et al., "Protein splicing elements: inteins and exteins—a definition of terms and recommended nomenclature," *Nucleic Acids Research* 22(7): 1125-1127, 1994. (3 pages).
Pfeifer et al., "Gene Therapy: Promises and Problems," *Annu. Rev. Genomics Hum. Genet.* 2:177-211, 2001. (37 pages).
Porter et al., "Chimeric antigen receptor T cells persist and induce sustained remissions in relapsed refractory chronic lymphocytic leukemia," *Science Translational Medicine* 7(303): 303ra139, Sep. 2, 2015.
Porteus et al., "Gene targeting using zinc finger nucleases," *Nature Biotechnology* 23(8): 967-973, Aug. 2005. (7 pages).
Pâques et al., "Meganucleases and DNA Double-Strand Break-Induced Recombination: Perspectives for Gene Therapy," *Current Gene Therapy* 7:49-66, 2007.

Rapoport, "Protein translocation across the eukaryotic endoplasmic reticulum and bacterial plasma membranes," Nature vol. 450 (29), Nov. 2007, pp. 663-669.
Ren et al., "Multiplex genome editing to generate universal CAR T cells resistant to PD1 inhibition," *Clin Cancer Res* 23(9): 2255-2266, May 1, 2017. (HHS Public Access, Author Manuscript, available in PMC May 1, 2018) (21 pages).
Richards et al., "Engineered Fibronectin Type III Domain with a RGDWXE Sequence Binds with Enhanced Affinity and Specificity to Human αvβ3 Integrin," J. Mol. Biol. 326(5): 1475-1488, 2003.
Riddell et al., "The use of anti-CD3 and anti-CD28 monoclonal antibodies to clone and expand human antigen-specific T cells," J. Immunol. Methods 128(2): 189-201, 1990.
Rossi et al., "Genetic therapies against HIV," Nature Biotechnology 25(12):1444-1454, 2007.
Roux et al., "Structural analysis of the nurse shark (new) antigen receptor (NAR): Molecular convergence of NAR and unusual mammalian immunoglobulins," *Proc. Natl. Acad. Sci. USA* 95:11804-11809, Sep. 1998.
Sadelain et al., "The basic principles of chimeric antigen receptor (CAR) design," *Cancer Discov.* 3(4):388-398, Apr. 2013. (NIH Public Access, Author Manuscript, available in PMC Apr. 2, 2014) (21 pages).
Sandberg et al., "Human T-cell lines with well-defined T-cell receptor gene rearrangements as controls for the BIOMED-2 multiplex polymerase chain reaction tubes," Leukemia 21(2):230-237, 2007.
Sato et al., "Genes encoding putative natural killer cell C-type lectin receptors in teleostean fishes," Proc. Natl. Acad. Sci. USA 100(13): 7779-7784, 2003.
Savoldo et al., "CD28 costimulation improves expansion and persistence of chimeric antigen receptor-modified T cells in lymphoma patients," *J Clin Invest.* 121(5): 1822-1826, May 2011.
Sazinsky et al., "Aglycosylated immunoglobulin G1 variants productively engage activating Fc receptors," *PNAS* 105(51):20167-20172, Dec. 23, 2008.
Scatchard, "The Attractions of Proteins for Small Molecules and Ions," Annals of the New York Academy of Sciences 51(4): 660-672, May 31, 1949.
Schmidt et al., "Adoptive T-Cell Therapy of Melanoma: Promises and Challenges," Chapter 8, in Murph (ed.), Melanoma in the Clinic—Diagnosis, Management and Complications of Malignancy, InTech, Shanghai, China, 2011, pp. 115-132. (19 pages).
Schmidt et al., "The *Strep*-tag system for one-step purification and high-affinity detection or capturing of proteins," *Nature Protocols* 2(6): 1528-1535, Jun. 14, 2007.
Schmitt et al., "Induction of T cell development and establishment of T cell competence from embryonic stem cells differentiated in vitro," Nat. Immunol. 5(4):410-417, 2004.
Schmitt et al., "T Cell Receptor Gene Therapy for Cancer," *Human Gene Therapy* 20:1240-1248, Nov. 2009. (9 pages).
Schönfeld et al., "An engineered lipocalin specific for CTLA-4 reveals a combining site with structural and conformational features similar to antibodies," Proc. Natl. Acad. Sci. USA 106(20):8198-8203, 2009.
Shaner et al., "A guide to choosing fluorescent proteins," Nat Methods 2(12):905-909, Dec. 2005.
Shi et al., "The role of PD-1 and PD-L1 in T-cell immune suppression in patients with hematological malignancies," Journal of Hematology & Oncology 6:74, 2013. (6 pages).
Spiess et al., "Alternative molecular formats and therapeutic applications for bispecific antibodies," *Mol. Immunol.* 67:95-106, 2015.
Stone et al., "A novel T cell receptor single-chain signaling complex mediates antigen- specific T cell activity and tumor control," *Cancer Immunol. Immunother*. 63(11): 1163-1176, Nov. 2014. (NIH Public Access, Author Manuscript, available in PMC Nov. 1, 2015) (23 pages).
Stumpp et al., "Designing Repeat Proteins: Modular Leucine-rich Repeat Protein Libraries Based on the Mammalian Ribonuclease Inhibitor Family," J. Mol. Biol. 332(2):471-487, 2003.
Sussman et al., "Isolation and Characterization of New Homing Endonuclease Specificities at Individual Target Site Positions," *J. Mol. Biol.* 342:31-41, 2004.

(56) References Cited

OTHER PUBLICATIONS

Szymczak et al., "Correction of multi-gene deficiency in vivo using a single 'self-cleaving' 2A peptide-based retroviral vector," Nat. Biotechnol. 22(5):589-594, 2004.
Terentis et al., "The Selenazal Drug Ebselen Potently Inhibits Indoleamine 2,3-Dioxygenase by Targeting Enzyme Cysteine Residues," Biochemistry 49:591-600, 2010.
Till et al., "Adoptive immunotherapy for indolent non-Hodgkin lymphoma and mantle cell lymphoma using genetically modified autologous CD20-specific T cells," Blood 112(6):2261-2271, Sep. 15, 2008. (11 pages).
Till et al., "CD20-specific adoptive immunotherapy for lymphoma using a chimeric antigen receptor with both CD28 and 4-1BB domains: pilot clinical trial results," Blood 119(17):3940-3950, Apr. 26, 2012.
Torikai et al., "A foundation for universal T-cell based immunotherapy: T cells engineered to express a CD19-specific chimeric-antigen-receptor and eliminate expression of endogenous TCR," Blood 119(24):5697-5705, Jun. 14, 2012. (10 pages).
Torikai et al., "Genetic editing of HLA expression in hematopoietic stem cells to broaden their human application," Nature Scientific Reports 6:21757, Feb. 23, 2016. (11 pages).
Torikai et al., "Toward eliminating HLA class I expression to generate universal cells from allogeneic donors," Blood 122(8): 1341-1349, Aug. 22, 2013. (9 pages).
Verhoeyen et al., Methods in Molecular Biology, Methods and Protocols vol. 506, Humana Press, 2009, Chapter 8, "Lentiviral Vector Gene Transfer into Human T Cells," pp. 97-114.
Vincke et al., "General Strategy to Humanize a Camelid Single-domain Antibody and Identification of a Universal Humanized Nanobody Scaffold," J. Biol. Chem. 284(5):3273- 3284, 2009.
Vita et al., "Scorpion toxins as natural scaffolds for protein engineering," Proc. Natl. Acad. Sci. USA 92(14):6404-6408, 1995.
Voss et al., "Mutagenesis of a flexible loop in streptavidin leads to higher affinity for the Strep-tag II peptide and improved performance in recombinant protein purification," Protein Engineering 10(8):975-982, 1997.
Walseng et al., "A TCR-based Chimeric Antigen Receptor," Scientific Reports 7(10713):1-10, Sep. 6, 2017.
Wang et al., "Optimizing Adoptive Polyclonal T Cell Immunotherapy of Lymphomas, Using a Chimeric T Cell Receptor Possessing CD28 and CD137 Costimulatory Domains," Human Gene Therapy 18:712-725, Aug. 2007.
Weidle et al., "The Emerging Role of New Protein Scaffold-based Agents for Treatment of Cancer," Cancer Genomics & Proteomics 10(4): 155-168, 2013.
Weisel et al., "A Model for Fibrinogen: Domains and Sequence," Science 230(4732): 1388-1390, 1985. (4 pages).
Wilson, "Analyzing Biomolecular Interactions," Science 295:2103-2105, Mar. 15, 2002.
Wolfe et al., "Analysis of Zinc Fingers Optimized via Phage Display: Evaluating the Utility of a Recognition Code," J. Mol. Biol. 285:1917-1934, 1999. (18 pages).
Wolff et al., "Monoclonal Antibody Homodimers: Enhanced Anti-tumor Activity in Nude Mice," Cancer Research 53:2560-2565, Jun. 1, 1993.
Wälchli et al., "A Practical Approach to T-Cell Receptor Cloning and Expression," PLoS One 6(11):e27930, Nov. 2011. (11 pages).
Xie et al., "sgRNAcas9: A Software Package for Designing CRISPR sgRNA and Evaluating Potential Off-Target Cleavage Sites," PLoS ONE 9(6): e100448, Jun. 23, 2014. (9 pages).
Yam et al., "Design of HIV Vectors for Efficient Gene Delivery into Human Hematopoietic Cells," Molecular Therapy 5(4):479-484, 2002.
Yang et al., "Therapeutic Potential and Challenges of Targeting Receptor Tyrosine Kinase ROR1 with Monoclonal Antibodies in B-Cell Malignancies," PLoS One 6(6):e21018, 2011. (15 pages).
Yu et al., "Targeting Strategies for Multifunctional Nanoparticles in Cancer Imaging and Therapy," Theranostics 2(1):3-44, 2012.
Zelensky et al., "The C-type lectin-like domain superfamily," FEBS J. 272(24):6179-6217, 2005.
Zhang et al., "Transduction of Human T Cells with a Novel T-Cell Receptor Confers Anti-HCV Reactivity," PLoS Pathogens 6(7):e1001018, 2010. (13 pages).
Zhao et al., "Primary Human Lymphocytes Transduced with NY-ESO-1 Antigen-Specific TCR Genes Recognize and Kill Diverse Human Tumor Cell Lines," The Journal of Immunology 174:4415-4423, 2005.

\* cited by examiner

FIG. 1A:

Strep-Tag II

SEQ ID NO: 1

Trp Ser His Pro Gln Phe Glu Lys

FIG. 1B:

Myc tag

SEQ ID NO: 2

Glu Gln Lys Leu Ile Ser Glu Glu Asp Leu

FIG. 1C:

V5 tag

SEQ ID NO: 3

Gly Lys Pro Ile Pro Asn Pro Leu Leu Gly Leu Asp Ser Thr

FIG. 1D:

Flag Tag

SEQ ID NO: 4

Asp Tyr Lys Asp Asp Asp Asp Lys

FIG. 1E:

Linker

SEQ ID NO: 5

Gly Gly Gly Gly Ser Gly Gly Gly Gly Ser

FIG. 1F:

Linker

SEQ ID NO: 6

Gly Gly Gly Ser Gly Gly Gly Ser

FIG. 1G:

Linker

SEQ ID NO: 7

Gly Gly Gly Ser Gly Gly Gly Ser Gly Gly Ser

FIG. 1H:

Core Hinge Region

SEQ ID NO: 8

Cys Pro Pro Cys Pro

FIG. 1I:

Strep-tag II Coding Sequence

SEQ ID NO: 9 tggagccacccgcagttcgaaaaa

FIG. 1J:

Linker

SEQ ID NO: 10

Gly Gly Ser Gly Ser Gly

FIG. 1K:

Xpress tag

SEQ ID NO: 11

Asp Leu Tyr Asp Asp Asp Asp Lys

FIG. 1L:

Avi Tag

SEQ ID NO: 12

Gly Leu Asn Asp Ile Phe Glu Ala Gln Lys Ile Glu Trp
His Glu

FIG. 1M:

Calmodulin Tag

SEQ ID NO: 13

Lys Arg Arg Trp Lys Lys Asn Phe Ile Ala Val Ser Ala Ala

Asn Arg Phe Lys Lys Ile Ser Ser Ser Gly Ala Leu

FIG. 1N:

HA Tag

SEQ ID NO: 14

Tyr Pro Tyr Asp Val Pro Asp Tyr Ala

FIG. 1O:

Soft Tag 1

SEQ ID NO: 15

Ser Leu Ala Glu Leu Leu Asn Ala Gly Leu Gly Gly Ser

FIG. 1P:

Softag 3

SEQ ID NO: 16

Thr Gln Asp Pro Ser Arg Val Gly

FIG. 1Q:

Strep-Tag

SEQ ID NO: 17

Trp Arg His Pro Gln Phe Gly Gly

FIG. 1R:

Engineered Tag of a Minimal Chelation Site

SEQ ID NO: 18

His Gly Gly His His Gly

FIG. 1S

Linker + Tag

SEQ ID NO: 19

Gly Gly Gly Gly Ser Gly Gly Gly Gly Ser Trp Ser His Pro Gln Phe Glu Lys

FIG. 1T:

Linker + Tag

SEQ ID NO: 20

Trp Ser His Pro Gln Phe Glu Lys Gly Gly Gly Gly Ser Gly Gly Gly Gly Ser

FIG. 1U:

Linker + Tag

SEQ ID NO: 21

Gly Gly Gly Gly Ser Gly Gly Gly Gly Ser Trp Ser His Pro Gln Phe Glu Lys Gly Gly Gly Ser Gly Gly Gly Ser Gly Gly Ser Trp Ser His Pro Gln Phe Glu Lys

FIG. 1V:

Linker + Tag

SEQ ID NO: 22

Trp Ser His Pro Gln Phe Glu Lys Gly Gly Gly Ser Gly Gly Gly Ser Gly Gly Ser Trp Ser His Pro Gln Phe Glu Lys Gly Gly Gly Gly Ser Gly Gly Gly Gly Ser

FIG. 1W:

Linker + Tag

SEQ ID NO: 23

Gly Gly Gly Gly Ser Gly Gly Gly Gly Ser Trp Ser His Pro Gln Phe Glu Lys Gly Gly Gly Ser Gly Gly Gly Ser Gly Gly Ser Trp Ser His Pro Gln Phe Glu Lys Gly Gly Gly Gly Ser Gly Gly Gly Gly Ser Trp Ser His Pro Gln Phe Glu Lys

FIG. 1X:

Linker + Tag

SEQ ID NO: 24

Trp Ser His Pro Gln Phe Glu Lys Gly Gly Gly Gly Ser Gly Gly Gly Gly Ser Trp Ser His Pro Gln Phe Glu Lys Gly Gly Gly Ser Gly Gly Gly Ser Gly Gly Ser Trp Ser His Pro Gln Phe Glu Lys Gly Gly Gly Gly Ser Gly Gly Gly Gly Ser

FIG. 1Y:

Linker

SEQ ID NO: 25

Gly Gly Gly Gly Ser

FIG. 1Z:

Linker

SEQ ID NO: 26

Gly Gly Gly Ser

FIG. 1AA:

Linker

SEQ ID NO: 27

Gly Gly Gly Ser Gly Gly Gly Gly Ser

FIG. 1BB:

Linker

SEQ ID NO: 28

Gly Gly Gly Ser Gly Gly Ser

FIG. 1CC:

Linker

SEQ ID NO: 29

Gly Ser Gly Ser Gly

FIG. 2 tEGFR (SEQ ID NO: 32)

MLLLVTSLLLCELPHPAFLLIPRKVCNGIGIGEFKDSLSINATNIKHFKNCTSISGDLHILP
VAFRGDSFTHTPPLDPQELDILKTVKEITGFLLIQAWPENRTDLHAFENLEIIRGRTKQH
GQFSLAVVSLNITSLGLRSLKEISDGDVIISGNKNLCYANTINWKKLFGTSGQKTKIISN
RGENSCKATGQVCHALCSPEGCWGPEPRDCVSCRNVSRGRECVDKCNLLEGEPRE
FVENSECIQCHPECLPQAMNITCTGRGPDNCIQCAHYIDGPHCVKTCPAGVMGENNT
LVWKYADAGHVCHLCHPNCTYGCTGPGLEGCPTNGPKIPSIATGMVGALLLLLVVALG
IGLFM

FIG. 2 (cont'd)

| | | |
|---|---|---|
| Human IgG1 | EPKSCDKTHTCPPCP | (SEQ ID NO: 33) |
| Human IgG2 | ERKCCVECPPCP | (SEQ ID NO: 34) |
| Human IgG3 | ELKTPLGDTHTCPRCP | |
| | (EPKSCDTPPCPRCP)₃ | (SEQ ID NO: 35) |
| Human IgG4 | ESKYGPPCPSCP | (SEQ ID NO: 36) |
| Modified Human IgG4 | ESKYGPPCPPCP | (SEQ ID NO: 37) |
| Modified Human IgG4 | YGPPCPPCP | (SEQ ID NO: 38) |
| Modified Human IgG4 | KYGPPCPPCP | (SEQ ID NO: 39) |
| Modified Human IgG4 | EVVKYGPPCPPCP | (SEQ ID NO: 40) |

Leader (SEQ ID NO: 41)

MLLLVTSLLLCELPHPAFLLIP

Hinge/Spacer (SEQ ID NO: 42)

ESKYGP<u>PCPPCP</u>

CH2 (SEQ ID NO: 43)

<u>APEFLGGPS</u>VFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTISKAK

CH3 (SEQ ID NO: 44)

GQPREPQVYTLPPSQEEMTKNQVSLTCLVKGFYPSDIAVEWESNGQPENNYKTTPP
VLDSDGSFFLYSRLTVDKSRWQEGNVFSCSVMHEALHNHYTQKSLSLSLGK

CD28 Transmembrane Domain (SEQ ID NO: 45)

MFWVLVVVGGVLACYSLLVTVAFIIFWV

T2A (SEQ ID NO: 46)

LEGGGEGRGSLLTCGDVEENPGPR

FIG. 2 (cont'd)

4-1BB (SEQ ID NO: 47)

KRGRKKLLYIFKQPFMRPVQTTQEEDGCSCRFPEEEEGGCEL

CD3 zeta (SEQ ID NO: 48)

RVKFSRSADAPAYQQGQNQLYNELNLGRREEYDVLDKRRGRDPEMGGKPRRKNPQEG
LYNELQKDKMAEAYSEIGMKGERRRGKGHDGLYQGLSTATKDTYDALHMQALPPR

ITAM1 (SEQ ID NO: 49)

APAYQQGQNQLYNELNLGRREEYDVLDKR

ITAM2 (SEQ ID NO: 50)

PQRRKNPQEGLYNELQKDKMAEAYSEIGM

ITAM3 (SEQ ID NO: 51)

ERRRGKGHDGLYQGLSTATKDTYDALHMQ

FIG. 3

Intermediate Spacer (e.g., IgG4 hinge region sequence and a CH3 region (*e.g.*, SEQ ID NO: 31))

Glu Ser Lys Tyr Gly Pro Pro Cys Pro Pro Cys Pro Gly Gln Pro Arg Glu Pro Gln Val Tyr Thr Leu Pro Pro Ser Gln Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Arg Leu Thr Val Asp Lys Ser Arg Trp Gln Glu Gly Asn Val Phe Ser Cys Ser Val Met His Glu Ala Leu His Asn His Tyr Thr Gln Lys Ser Leu Ser Leu Ser Leu Gly Lys

Long spacer (e.g., IgG4 hinge region sequence, a CH2 region, and a CH3 region (e.g., SEQ ID NO: 30))

Glu Ser Lys Tyr Gly Pro Pro Cys Pro Pro Cys Pro Ala Pro Glu Phe Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Gln Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Arg Leu Thr Val Asp Lys Ser Arg Trp Gln Glu Gly Asn Val Phe Ser Cys Ser Val Met His Glu Ala Leu His Asn His Tyr Thr Gln Lys Ser Leu Ser Leu Ser Leu Gly Lys

FIG. 3 (cont'd)

Variant of CD3ζ and a portion of the 4-1BB intracellular signaling domain

4-1BB
```
DNA: AAACGGGGCAGAAAGAAACTCCTGTATATATTCAAACAACCATTTATG
AA:  K   R   G   R   K   K   L   L   Y   I   F   K   Q   P   F   M

DNA: AGACCAGTACAAACTACTCAAGAGGAAGATGGCTGTAGCTGCCGATTTCCA
AA:  R   P   V   Q   T   T   Q   E   E   D   G   C   S   C   R   F   P
                                                        CD3Zeta
DNA: GAAGAAGAAGAAGGAGGATGTGAACT:GCGGGTGAAGTTCAGCAGAAGCGCC
AA:  E   E   E   E   G   G   C   E   L   R   V   K   F   S   R   S   A DNA: GACGCCCTGCCTACCAGCAGGGCCAGAATCAGCTGTACAACGAGCTGAAC
AA:  D   A   P   A   Y   Q   Q   G   Q   N   Q   L   Y   N   E   L   N DNA: CTGGGCAGAAGGGAAGAGTACGACGTCCTGGATAAGCGGAGAGGCCGGGAC
AA:  L   G   R   R   E   E   Y   D   V   L   D   K   R   R   G   R   D DNA: CCTGAGATGGGCGGCAAGCCTCGGCGGAAGAACCCCCAGGAAGGCCTGTAT
AA:  P   E   M   G   G   K   P   R   R   K   N   P   Q   E   G   L   Y DNA: AACGAACTGCAGAAAGACAAGATGGCCGAGGCCTACAGCGAGATCGGCATG
AA:  N   E   L   Q   K   D   K   M   A   E   A   Y   S   E   I   G   M DNA: AAGGGCGAGCGGAGGCGGGGCAAGGGCCACGACGGCCTGTATCAGGGCCTG
AA:  K   G   E   R   R   R   G   K   G   H   D   G   L   Y   Q   G   L DNA: TCCACCGCCACCAAGGATACCTACGACGCCCTGCACATGCAGGCCCTGCCC
AA:  S   T   A   T   K   D   T   Y   D   A   L   H   M   Q   A   L   P

DNA: CCAAGG   (SEQ ID NO: 52)
AA:  P   R    (SEQ ID NO: 53)
```

SEQUENCE LISTING

```
<160> NUMBER OF SEQ ID NOS: 53

<210> SEQ ID NO 1
<211> LENGTH: 8
<212> TYPE: PRT
<213> ORGANISM: Artificial Sequence
<220> FEATURE:
<223> OTHER INFORMATION: STREP-TAG II

<400> SEQUENCE: 1

Trp Ser His Pro Gln Phe Glu Lys
1               5
```

```
<210> SEQ ID NO 2
<211> LENGTH: 10
<212> TYPE: PRT
<213> ORGANISM: Artificial Sequence
<220> FEATURE:
<223> OTHER INFORMATION: Myc tag

<400> SEQUENCE: 2

Glu Gln Lys Leu Ile Ser Glu Glu Asp Leu
1               5                   10

<210> SEQ ID NO 3
<211> LENGTH: 14
<212> TYPE: PRT
<213> ORGANISM: Artificial Sequence
<220> FEATURE:
<223> OTHER INFORMATION: V5 tag

<400> SEQUENCE: 3

Gly Lys Pro Ile Pro Asn Pro Leu Leu Gly Leu Asp Ser Thr
1               5                   10

<210> SEQ ID NO 4
<211> LENGTH: 8
<212> TYPE: PRT
<213> ORGANISM: Artificial Sequence
<220> FEATURE:
<223> OTHER INFORMATION: FLAG Tag

<400> SEQUENCE: 4

Asp Tyr Lys Asp Asp Asp Asp Lys
1               5

<210> SEQ ID NO 5
<211> LENGTH: 10
<212> TYPE: PRT
<213> ORGANISM: Artificial Sequence
<220> FEATURE:
<223> OTHER INFORMATION: Linker

<400> SEQUENCE: 5

Gly Gly Gly Gly Ser Gly Gly Gly Gly Ser
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Linker

<400> SEQUENCE: 6

Gly Gly Gly Ser Gly Gly Gly Ser
1               5

<210> SEQ ID NO 7
<211> LENGTH: 11
<212> TYPE: PRT
<213> ORGANISM: Artificial Sequence
<220> FEATURE:
<223> OTHER INFORMATION: Linker

<400> SEQUENCE: 7

Gly Gly Gly Ser Gly Gly Gly Ser Gly Gly Ser
1               5                   10
```

```
<210> SEQ ID NO 8
<211> LENGTH: 5
<212> TYPE: PRT
<213> ORGANISM: Artificial Sequence
<220> FEATURE:
<223> OTHER INFORMATION: Core Hinge Region

<400> SEQUENCE: 8

Cys Pro Pro Cys Pro
1               5

<210> SEQ ID NO 9
<211> LENGTH: 24
<212> TYPE: DNA
<213> ORGANISM: Artificial Sequence
<220> FEATURE:
<223> OTHER INFORMATION: STREP-TAG II Coding Sequence

<400> SEQUENCE: 9
tggagccacc cgcagttcga aaaa                                              24

<210> SEQ ID NO 10
<211> LENGTH: 6
<212> TYPE: PRT
<213> ORGANISM: Artificial Sequence
<220> FEATURE:
<223> OTHER INFORMATION: Linker

<400> SEQUENCE: 10

Gly Gly Ser Gly Ser Gly
1               5

<210> SEQ ID NO 11
<211> LENGTH: 8
<212> TYPE: PRT
<213> ORGANISM: Artificial Sequence
<220> FEATURE:
<223> OTHER INFORMATION: Xpress tag

<400> SEQUENCE: 11

Asp Leu Tyr Asp Asp Asp Asp Lys
1               5

<210> SEQ ID NO 12
<211> LENGTH: 15
<212> TYPE: PRT
<213> ORGANISM: Artificial Sequence
<220> FEATURE:
<223> OTHER INFORMATION: Avi Tag

<400> SEQUENCE: 12

Gly Leu Asn Asp Ile Phe Glu Ala Gln Lys Ile Glu Trp His Glu
1               5                   10                  15

<210> SEQ ID NO 13
<211> LENGTH: 26
<212> TYPE: PRT
<213> ORGANISM: Artificial Sequence
<220> FEATURE:
<223> OTHER INFORMATION: Calmodulin Tag

<400> SEQUENCE: 13

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25
```

```
<210> SEQ ID NO 14
<211> LENGTH: 9
<212> TYPE: PRT
<213> ORGANISM: Artificial Sequence
<220> FEATURE:
<223> OTHER INFORMATION: HA Tag

<400> SEQUENCE: 14

Tyr Pro Tyr Asp Val Pro Asp Tyr Ala
1               5

<210> SEQ ID NO 15
<211> LENGTH: 13
<212> TYPE: PRT
<213> ORGANISM: Artificial Sequence
<220> FEATURE:
<223> OTHER INFORMATION: Soft Tag 1

<400> SEQUENCE: 15

Ser Leu Ala Glu Leu Leu Asn Ala Gly Leu Gly Gly Ser
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Softag 3

<400> SEQUENCE: 16

Thr Gln Asp Pro Ser Arg Val Gly
1               5

<210> SEQ ID NO 17
<211> LENGTH: 8
<212> TYPE: PRT
<213> ORGANISM: Artificial Sequence
<220> FEATURE:
<223> OTHER INFORMATION: Strep-Tag

<400> SEQUENCE: 17

Trp Arg His Pro Gln Phe Gly Gly
1               5

<210> SEQ ID NO 18
<211> LENGTH: 6
<212> TYPE: PRT
<213> ORGANISM: Artificial Sequence
<220> FEATURE:
<223> OTHER INFORMATION: Engineered Tag of a Minimal Chelation Site

<400> SEQUENCE: 18

His Gly Gly His His Gly
1               5

<210> SEQ ID NO 19
<211> LENGTH: 18
<212> TYPE: PRT
<213> ORGANISM: Artificial Sequence
<220> FEATURE:
<223> OTHER INFORMATION: Linker + Tag

<400> SEQUENCE: 19

Gly Gly Gly Gly Ser Gly Gly Gly Ser Trp Ser His Pro Gln Phe
1               5                   10                  15

Glu Lys
```

```
<210> SEQ ID NO 20
<211> LENGTH: 18
<212> TYPE: PRT
<213> ORGANISM: Artificial Sequence
<220> FEATURE:
<223> OTHER INFORMATION: Linker + Tag

<400> SEQUENCE: 20

Trp Ser His Pro Gln Phe Glu Lys Gly Gly Gly Ser Gly Gly Gly
1               5                   10                  15

Gly Ser

<210> SEQ ID NO 21
<211> LENGTH: 37
<212> TYPE: PRT
<213> ORGANISM: Artificial Sequence
<220> FEATURE:
<223> OTHER INFORMATION: Linker + Tag

<400> SEQUENCE: 21

Gly Gly Gly Gly Ser Gly Gly Gly Gly Ser Trp Ser His Pro Gln Phe
1               5                   10                  15

Glu Lys Gly Gly Gly Gly Ser Gly Gly Gly Ser Gly Gly Ser Trp Ser His
                20                  25                  30

Pro Gln Phe Glu Lys
        35

<210> SEQ ID NO 22
<211> LENGTH: 37
<212> TYPE: PRT
<213> ORGANISM: Artificial Sequence
<220> FEATURE:
<223> OTHER INFORMATION: Linker + Tag

<400> SEQUENCE: 22

Trp Ser His Pro Gln Phe Glu Lys Gly Gly Gly Ser Gly Gly Gly Ser
1               5                   10                  15

Gly Gly Ser Trp Ser His Pro Gln Phe Glu Lys Gly Gly Gly Gly Ser
                20                  25                  30

Gly Gly Gly Gly Ser
        35

<210> SEQ ID NO 23
<211> LENGTH: 55
<212> TYPE: PRT
<213> ORGANISM: Artificial Sequence
<220> FEATURE:
<223> OTHER INFORMATION: Linker + Tag

<400> SEQUENCE: 23

Gly Gly Gly Gly Ser Gly Gly Gly Gly Ser Trp Ser His Pro Gln Phe
1               5                   10                  15

Glu Lys Gly Gly Gly Gly Ser Gly Gly Gly Ser Gly Gly Ser Trp Ser His
                20                  25                  30

Pro Gln Phe Glu Lys Gly Gly Gly Gly Ser Gly Gly Gly Ser Trp
        35                  40                  45

Ser His Pro Gln Phe Glu Lys
        50                  55

<210> SEQ ID NO 24
<211> LENGTH: 55
```

<212> TYPE: PRT
<213> ORGANISM: Artificial Sequence
<220> FEATURE:
<223> OTHER INFORMATION: Linker + Tag

<400> SEQUENCE: 24

Trp Ser His Pro Gln Phe Glu Lys Gly Gly Gly Ser Gly Gly Gly
1               5                   10                  15
Gly Ser Trp Ser His Pro Gln Phe Glu Lys Gly Gly Gly Ser Gly Gly
            20                  25                  30
Gly Ser Gly Gly Ser Trp Ser His Pro Gln Phe Glu Lys Gly Gly Gly
        35                  40                  45
Gly Ser Gly Gly Gly Ser
    50                  55

<210> SEQ ID NO 25
<211> LENGTH: 5
<212> TYPE: PRT
<213> ORGANISM: Artificial Sequence
<220> FEATURE:
<223> OTHER INFORMATION: Linker

<400> SEQUENCE: 25

Gly Gly Gly Gly Ser
1               5

<210> SEQ ID NO 26
<211> LENGTH: 4
<212> TYPE: PRT
<213> ORGANISM: Artificial Sequence
<220> FEATURE:
<223> OTHER INFORMATION: Linker

<400> SEQUENCE: 26

Gly Gly Gly Ser
1

<210> SEQ ID NO 27
<211> LENGTH: 9
<212> TYPE: PRT
<213> ORGANISM: Artificial Sequence
<220> FEATURE:
<223> OTHER INFORMATION: Linker

<400> SEQUENCE: 27

Gly Gly Gly Ser Gly Gly Gly Gly Ser
1               5

<210> SEQ ID NO 28
<211> LENGTH: 7
<212> TYPE: PRT
<213> ORGANISM: Artificial Sequence
<220> FEATURE:
<223> OTHER INFORMATION: Linker

<400> SEQUENCE: 28

Gly Gly Gly Ser Gly Gly Ser
1               5

<210> SEQ ID NO 29
<211> LENGTH: 5
<212> TYPE: PRT
<213> ORGANISM: Artificial Sequence
<220> FEATURE:
<223> OTHER INFORMATION: Linker -continued

```
<400> SEQUENCE: 29

Gly Ser Gly Ser Gly
1               5

<210> SEQ ID NO 30
<211> LENGTH: 229
<212> TYPE: PRT
<213> ORGANISM: Artificial Sequence
<220> FEATURE:
<223> OTHER INFORMATION: Long spacer

<400> SEQUENCE: 30

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 31
<211> LENGTH: 119
<212> TYPE: PRT
<213> ORGANISM: Artificial Sequence
<220> FEATURE:
<223> OTHER INFORMATION: Intermediate Spacer

<400> SEQUENCE: 31

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45
```

```
Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                    85                  90                  95

Cys Ser Val Met His Glu Ala Leu His Asn His Tyr Thr Gln Lys Ser
                100                 105                 110

Leu Ser Leu Ser Leu Gly Lys
            115

<210> SEQ ID NO 32
<211> LENGTH: 357
<212> TYPE: PRT
<213> ORGANISM: Homo sapiens

<400> SEQUENCE: 32

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
                20                  25                  30

Glu Phe Lys Asp Ser Leu Ser Ile Asn Ala Thr Asn Ile Lys His Phe
                35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
                100                 105                 110

Glu Ile Ile Arg Gly Arg Thr Lys Gln His Gly Gln Phe Ser Leu Ala
                115                 120                 125

Val Val Ser Leu Asn Ile Thr Ser Leu Gly Leu Arg Ser Leu Lys Glu
            130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
                180                 185                 190

Gln Val Cys His Ala Leu Cys Ser Pro Glu Gly Cys Trp Gly Pro Glu
            195                 200                 205

Pro Arg Asp Cys Val Ser Cys Arg Asn Val Ser Arg Gly Arg Glu Cys
            210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
                260                 265                 270

His Tyr Ile Asp Gly Pro His Cys Val Lys Thr Cys Pro Ala Gly Val
            275                 280                 285

Met Gly Glu Asn Asn Thr Leu Val Trp Lys Tyr Ala Asp Ala Gly His
290                 295                 300
```

-continued

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
            340                 345                 350

Ile Gly Leu Phe Met
        355

<210> SEQ ID NO 33
<211> LENGTH: 15
<212> TYPE: PRT
<213> ORGANISM: Homo sapiens

<400> SEQUENCE: 33

Glu Pro Lys Ser Cys Asp Lys Thr His Thr Cys Pro Pro Cys Pro
1               5                   10                  15

<210> SEQ ID NO 34
<211> LENGTH: 12
<212> TYPE: PRT
<213> ORGANISM: Homo sapiens

<400> SEQUENCE: 34

Glu Arg Lys Cys Cys Val Glu Cys Pro Pro Cys Pro
1               5                   10

<210> SEQ ID NO 35
<211> LENGTH: 61
<212> TYPE: PRT
<213> ORGANISM: Homo sapiens

<400> SEQUENCE: 35

Glu Leu Lys Thr Pro Leu Gly Asp Thr His Thr Cys Pro Arg Cys Pro
1               5                   10                  15

Glu Pro Lys Ser Cys Asp Thr Pro Pro Pro Cys Pro Arg Cys Pro Glu
                20                  25                  30

Pro Lys Ser Cys Asp Thr Pro Pro Pro Cys Pro Arg Cys Pro Glu Pro
            35                  40                  45

Lys Ser Cys Asp Thr Pro Pro Pro Cys Pro Arg Cys Pro
        50                  55                  60

<210> SEQ ID NO 36
<211> LENGTH: 12
<212> TYPE: PRT
<213> ORGANISM: Homo sapiens

<400> SEQUENCE: 36

Glu Ser Lys Tyr Gly Pro Pro Cys Pro Ser Cys Pro
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Modified Human IgG4

<400> SEQUENCE: 37

Glu Ser Lys Tyr Gly Pro Pro Cys Pro Pro Cys Pro
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Modified Human IgG4

<400> SEQUENCE: 38

Tyr Gly Pro Pro Cys Pro Pro Cys Pro
1               5

<210> SEQ ID NO 39
<211> LENGTH: 10
<212> TYPE: PRT
<213> ORGANISM: Artificial Sequence
<220> FEATURE:
<223> OTHER INFORMATION: Modified Human IgG4

<400> SEQUENCE: 39

Lys Tyr Gly Pro Pro Cys Pro Pro Cys Pro
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Modified Human IgG4

<400> SEQUENCE: 40

Glu Val Val Lys Tyr Gly Pro Pro Cys Pro Pro Cys Pro
1               5                   10

<210> SEQ ID NO 41
<211> LENGTH: 22
<212> TYPE: PRT
<213> ORGANISM: Artificial Sequence
<220> FEATURE:
<223> OTHER INFORMATION: Leader

<400> SEQUENCE: 41

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 42
<211> LENGTH: 12
<212> TYPE: PRT
<213> ORGANISM: Artificial Sequence
<220> FEATURE:
<223> OTHER INFORMATION: Hinge/Spacer

<400> SEQUENCE: 42

Glu Ser Lys Tyr Gly Pro Pro Cys Pro Pro Cys Pro
1               5                   10

<210> SEQ ID NO 43
<211> LENGTH: 110
<212> TYPE: PRT
<213> ORGANISM: Pan troglodytes

<400> SEQUENCE: 43

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 44
<211> LENGTH: 107
<212> TYPE: PRT
<213> ORGANISM: Homo sapiens

<400> SEQUENCE: 44

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 45
<211> LENGTH: 28
<212> TYPE: PRT
<213> ORGANISM: Homo sapiens

<400> SEQUENCE: 45

Met Phe Trp Val Leu Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 46
<211> LENGTH: 24
<212> TYPE: PRT
<213> ORGANISM: Thosea asigna

<400> SEQUENCE: 46

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 47
<211> LENGTH: 42
<212> TYPE: PRT

```
<213> ORGANISM: Artificial Sequence
<220> FEATURE:
<223> OTHER INFORMATION: 4-1BB

<400> SEQUENCE: 47

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 48
<211> LENGTH: 112
<212> TYPE: PRT
<213> ORGANISM: Artificial sequence
<220> FEATURE:
<223> OTHER INFORMATION: CD3 Zeta

<400> SEQUENCE: 48

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 49
<211> LENGTH: 29
<212> TYPE: PRT
<213> ORGANISM: Artificial sequence
<220> FEATURE:
<223> OTHER INFORMATION: ITAM1

<400> SEQUENCE: 49

Ala Pro Ala Tyr Gln Gln Gly Gln Asn Gln Leu Tyr Asn Glu Leu Asn
1               5                   10                  15

Leu Gly Arg Arg Glu Glu Tyr Asp Val Leu Asp Lys Arg
            20                  25

<210> SEQ ID NO 50
<211> LENGTH: 29
<212> TYPE: PRT
<213> ORGANISM: Artificial sequence
<220> FEATURE:
<223> OTHER INFORMATION: ITAM2

<400> SEQUENCE: 50

Pro Gln Arg Arg Lys Asn Pro Gln Glu Gly Leu Tyr Asn Glu Leu Gln
1               5                   10                  15

Lys Asp Lys Met Ala Glu Ala Tyr Ser Glu Ile Gly Met
            20                  25
```

```
<210> SEQ ID NO 51
<211> LENGTH: 29
<212> TYPE: PRT
<213> ORGANISM: Artificial sequence
<220> FEATURE:
<223> OTHER INFORMATION: ITAM3

<400> SEQUENCE: 51

Glu Arg Arg Arg Gly Lys Gly His Asp Gly Leu Tyr Gln Gly Leu Ser
1               5                   10                  15

Thr Ala Thr Lys Asp Thr Tyr Asp Ala Leu His Met Gln
            20                  25

<210> SEQ ID NO 52
<211> LENGTH: 462
<212> TYPE: DNA
<213> ORGANISM: Artificial Sequence
<220> FEATURE:
<223> OTHER INFORMATION: Variant of CD3 Zeta and a portion of the 4-1BB
      intracellular signaling domain

<400> SEQUENCE: 52
aaacggggca gaaagaaact cctgtatata ttcaaacaac catttatgag accagtacaa       60
actactcaag aggaagatgg ctgtagctgc cgatttccag aagaagaaga aggaggatgt      120
gaactgcggg tgaagttcag cagaagcgcc gacgcccctg cctaccagca gggccagaat      180
cagctgtaca acgagctgaa cctgggcaga agggaagagt acgacgtcct ggataagcgg      240
agaggccggg accctgagat gggcggcaag cctcggcgga agaaccccca ggaaggcctg      300
tataacgaac tgcagaaaga caagatggcc gaggcctaca gcgagatcgg catgaagggc      360
gagcggaggc ggggcaaggg ccacgacggc ctgtatcagg gcctgtccac cgccaccaag      420 gataccacg acgccctgca catgcaggcc ctgccccaa gg                         462

<210> SEQ ID NO 53
<211> LENGTH: 154
<212> TYPE: PRT
<213> ORGANISM: Artificial Sequence
<220> FEATURE:
<223> OTHER INFORMATION: Variant of CD3 Zeta and a portion of the 4-1BB
      intracellular signaling domain

<400> SEQUENCE: 53

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Arg Val Lys Phe Ser Arg
        35                  40                  45

Ser Ala Asp Ala Pro Ala Tyr Gln Gln Gly Gln Asn Gln Leu Tyr Asn
    50                  55                  60

Glu Leu Asn Leu Gly Arg Arg Glu Glu Tyr Asp Val Leu Asp Lys Arg
65                  70                  75                  80

Arg Gly Arg Asp Pro Glu Met Gly Gly Lys Pro Arg Arg Lys Asn Pro
                85                  90                  95

Gln Glu Gly Leu Tyr Asn Glu Leu Gln Lys Asp Lys Met Ala Glu Ala
            100                 105                 110

Tyr Ser Glu Ile Gly Met Lys Gly Glu Arg Arg Arg Gly Lys Gly His
        115                 120                 125

Asp Gly Leu Tyr Gln Gly Leu Ser Thr Ala Thr Lys Asp Thr Tyr Asp
    130                 135                 140
```

```
Ala Leu His Met Gln Ala Leu Pro Pro Arg
145                 150
```

US 11,827,904 B2

MODIFIED STEM CELLS AND USES THEREOF

CROSS REFERENCE TO RELATED APPLICATION

This application claims priority to U.S. Provisional Patent Application No. 62/154,573, filed on Apr. 29, 2015, the entire contents of which are incorporated herein.

FIELD OF THE DISCLOSURE

Stem cells are modified to express an extracellular component including a tag cassette. The tag cassette can be used to detect, enrich for, isolate, activate, track, deplete, or eliminate the cells. The modified cells can be administered before or following differentiation into a more committed cell type.

BACKGROUND OF THE DISCLOSURE

A goal of medicine is to regenerate the architecture and/or function of tissues and organs totally or partially lost due to disease, trauma, or aging. Stem cells are an important tool in such regenerative medicine strategies.

SUMMARY OF THE DISCLOSURE

The current disclosure provides genetically modified stem cells that can be more-readily detected, enriched for, isolated, activated, tracked, depleted, or eliminated before or after administration to a subject (e.g., in vitro, in vivo or ex vivo). The stem cells are modified to express an extracellular component including a tag cassette that specifically binds an exogenous cognate binding molecule that can be used to detect, enrich for, isolate, activate, track, deplete, or eliminate a modified stem cell before or after administration to a subject. The modified stem cells can also be differentiated to a number of different cell types for administration to subjects. Administered differentiated cells can also be detected, enriched for, isolated, activated, tracked, depleted, or eliminated before or after administration to a subject based on continued expression of the tag cassette. The modified stem cells have beneficial uses in manufacturing, research, and therapy.

BRIEF DESCRIPTION OF THE FIGURES

FIGS. 1A-1CC. Exemplary Exogenous Cognate Binding Molecule and Supporting Sequences. FIG. 1A: Strep-Tag II (SEQ ID NO:1); FIG. 1B: Myc tag (SEQ ID NO:2); FIG. 1C: V5 tag (SEQ ID NO:3); FIG. 1D: Flag Tag (SEQ ID NO:4); FIG. 1E: Linker (SEQ ID NO:5); FIG. 1F: Linker (SEQ ID NO:6); FIG. 1G: Linker (SEQ ID NO:7); FIG. 1H: Core Hinge Region (SEQ ID NO:8); FIG. 1I: Strep-tag II Coding Sequence (SEQ ID NO:9); FIG. 1J: Linker (SEQ ID NO:10); FIG. 1K: Xpress tag (SEQ ID NO:11); FIG. 1L: Avi Tag (SEQ ID NO:12); FIG. 1M: Calmodulin Tag (SEQ ID NO:13); FIG. 1N: HA Tag (SEQ ID NO:14); FIG. 1O: Soft Tag 1 (SEQ ID NO:15); FIG. 1P: Softag 3 (SEQ ID NO:16); FIG. 1Q: Strep-Tag (SEQ ID NO:17); FIG. 1R: Engineered Tag of a Minimal Chelation Site (SEQ ID NO:18); FIG. 1S: Linker+Tag (SEQ ID NO:19); FIG. 1T: Linker+Tag (SEQ ID NO:20); FIG. 1U: Linker+Tag (SEQ ID NO:21); FIG. 1V: Linker+Tag (SEQ ID NO:22); FIG. 1W: Linker+Tag (SEQ ID NO:23); FIG. 1X: Linker+Tag (SEQ ID NO:24); FIG. 1Y: Linker (SEQ ID NO:25); FIG. 1Z: Linker (SEQ ID NO:26); FIG. 1AA: Linker (SEQ ID NO: 27); FIG. 1BB: Linker (SEQ ID NO: 28); and FIG. 1CC: Linker (SEQ ID NO: 29).

FIGS. 2 and 3 depict additional exemplary sequences described herein (SEQ ID NOs: 30-54).

DETAILED DESCRIPTION

A goal of medicine is to regenerate the architecture and/or function of tissues and organs totally or partially lost due to disease, trauma, or aging. Stem cells are an important tool in such regenerative medicine strategies.

The current disclosure provides genetically modified stem cells that can be more-readily detected, enriched for, isolated, activated, tracked, depleted, or eliminated before or after administration to a subject (e.g., in vitro, in vivo or ex vivo). The stem cells are modified to express an extracellular component including a tag cassette that specifically binds an exogenous cognate binding molecule that can be used to detect, enrich for, isolate, activate, track, deplete, or eliminate a modified stem cell before or after administration to a subject. The modified stem cells can also be differentiated to a number of different cell types for administration to subjects. Administered differentiated cells can also be detected, enriched for, isolated, activated, tracked, depleted, or eliminated before or after administration to a subject based on continued expression of the tag cassette.

More particularly, stem cells are genetically modified to express chimeric molecules having an extracellular component including a tag cassette. "Tag cassette" refers to a unique peptide sequence affixed to, fused to, or that is part of a protein of interest, to which a cognate binding molecule (e.g., receptor, ligand, antibody, or other binding partner) is capable of specifically binding where the binding property can be used to detect, enrich for, isolate, activate, track, deplete, or eliminate a tagged protein or cells expressing a tagged protein, particularly when a tagged protein is part of a heterogeneous population of proteins or other material, or when cells expressing a tagged protein are part of a heterogeneous population of cells (e.g., a biological sample like peripheral blood). In particular embodiments, the cognate binding molecule is an exogenous cognate binding molecule (ExoCBM). In certain embodiments, a cell expressing a tag cassette can be contacted with an ExoCBM to induce a biological response, such as to promote cell activation (e.g., expansion, differentiation, and/or function) or cell death (e.g., depletion or elimination).

"Exogenous" refers to any gene, protein, compound, molecule or activity that is not native to a host cell or a subject, or is any gene, protein, compound, molecule or activity native to a host cell or a subject but has been altered or mutated such that the structure, activity or both is different as between the native and mutated molecules. In certain embodiments, exogenous molecules are not endogenous to a host cell or subject, but instead nucleic acids encoding such molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). Exogenous molecules can include heterologous and non-endogenous molecules. "Homologous" or "homolog" refers to a molecule or activity found in or derived from a host cell, species or strain. For example, a heterologous molecule or gene encoding the molecule may be homologous to a native host cell or subject molecule or gene that encodes the molecule, respectively, but may have an altered structure, sequence, expression level or combinations thereof. A non-endogenous molecule may be from the same species, a different species or a combination thereof.

The term "endogenous" or "native" refers to a gene, protein, compound, molecule or activity that is normally present in a host cell or a subject. Exogenous molecules are not endogenous or native.

Tag Cassettes. A tag cassette included within an expressed chimeric molecule (e.g., a single chain fusion protein) can be an extracellular component or part of an extracellular component that can specifically bind to a cognate binding molecule with high affinity or avidity, wherein, in particular embodiments, the cognate binding molecule is exogenous to a host or a cell expressing the chimeric molecule.

Tag cassettes that bind EndoCBMs include, e.g., a truncated EGFR. An exemplary gene sequence encoding the truncated EGFR is shown in FIG. 2 (SEQ ID NO: 32). Tag cassettes that bind ExoCBMs include, e.g., Strep® tag (IBA, GmbH, Goettingen, Germany; which refers the original Strep tag, Strep tag II, or any variant thereof; see, e.g., U.S. Pat. No. 7,981,632), His tag, Flag tag, Xpress tag, Avi tag, Calmodulin tag, Polyglutamate tag, HA tag, Myc tag, Nus tag, S tag, SBP tag, Softag 1, Softag 3, V5 tag, CREB-binding protein (CBP), glutathione S-transferase (GST), maltose binding protein (MBP), green fluorescent protein (GFP), Thioredoxin tag, or any combination thereof. In certain embodiments, a tag cassette is a Strep tag having an amino acid sequence of SEQ ID NO:1 or SEQ ID NO:17. In other embodiments, a tag cassette may be a genetically engineered affinity site, such as a minimal chelation site (e.g., SEQ ID NO:18).

Tag cassettes may be present in multiple copies in fusion proteins. For example, a fusion protein can have one, two, three, four or five tag cassettes (e.g., Strep tag). In certain embodiments, a chimeric molecule can include one tag cassette, two tag cassettes, three tag cassettes, four tag cassettes, or five tag cassettes. Each of the plurality of tag cassettes may be the same or different. Exemplary embodiments include a chimeric molecule having two Strep tag cassettes, or a His tag and a Strep tag cassette, or a HA tag and a Strep tag cassette, or a Myc tag and a Strep tag cassette. Alternatively, a chimeric molecule will have multiple tag cassettes of the same type or same amino acid sequence, such as two, three, four or five Strep tag cassettes (e.g., Strep tag II).

In some embodiments, a first tag cassette can provide an activation signal and a distinct second tag cassette might be used to associate with a detection reagent or associate with an antibody-toxin conjugate or with an antibody-imaging agent conjugate.

A chimeric molecule including one or more tag cassettes will be capable of associating with a cognate binding molecule, wherein the cognate binding molecule is exogenous to the host or cell expressing a fusion protein including a tag cassette as described herein. In certain embodiments, a tag cassette present in a chimeric molecule is a Strep tag, which has streptavidin, Strep-tactin® (IBA, GmbH, Goettingen, Germany) or both as a cognate binding molecule, or is recognized by antibodies specific for a Strep tag. In certain embodiments, the cognate binding molecule (e.g., receptor, protein, antibody) may be soluble, part of a matrix composition, or conjugated to a solid surface (e.g., plate, bead). Exemplary solid surfaces include beads and particles (e.g., micro and nano), such as magnetic beads and particles.

In particular embodiments modified cells expressing chimeric molecules can be identified by flow cytometry using a tag cassette specific cognate binding molecule such as an ExoCBM. In particular examples, purified modified cells expressing chimeric molecules are detected using anti-strep tag II (STII) allophycocyanin (APC) and/or Strep-tactin APC ExoCBMs.

In particular embodiments modified cells expressing chimeric molecules can be sorted by flow cytometry from low purity (e.g., 1%-30%) to high purity (e.g., 75%-99%) with a tag-specific cognate binding molecule linked to a fluorochrome. In particular embodiments, the tag cassette can include Strep tag II and the tag-specific ExoCBM can be an anti-STII mAb linked to a fluorochrome.

In particular embodiments modified cells expressing chimeric molecules (e.g., with three Strep tag cassettes) can be directly enriched by using Strep-tactin beads of various sizes. Thus, in certain embodiments, cells expressing a chimeric molecule can be detected, enriched for, isolated, tracked, depleted, or eliminated by binding to cognate binding molecule antibodies that specifically bind a tag cassette (e.g., anti-tag antibodies), or by other proteins that specifically bind a tag cassette (e.g., Strep-tactin binding to the Strep tag), which are conjugated to beads, a cell culture plate, agarose, or any other solid surface matrix. In certain embodiments, such cells are detected, enriched for, isolated, depleted, or eliminated by using an affinity column.

An advantage of the instant disclosure is that modified cells expressing a chimeric molecule can be administered to a subject and then can be depleted or eliminated using the ExoCBM to a tag cassette. In certain embodiments, the present disclosure provides a method for depleting or eliminating a modified cell expressing a chimeric molecule by using an ExoCBM that specifically binds the tag cassette, or by using a second modified cell expressing an ExoCBM that specifically binds the tag cassette. Depletion or elimination of modified cells may be accomplished using depletion or elimination agents specific for a tag cassette. For example, if a Strep tag is used, then an anti-Strep tag antibody, anti-Strep tag scFv, or Strep-tactin each fused to or conjugated to a cell-toxic reagent (such as a toxin or radiometal) may be used, or an anti-Strep tag/anti-CD3 bispecific scFv, or an anti-Strep tag CAR T cell may be used.

In certain further embodiments, modified cells expressing chimeric molecules as disclosed herein are activated in vivo, such as at the site of a treatment. For example, a composition (e.g., alginate, basement membrane matrix (MATRIGEL®), biopolymer, or other matrix) or a carrier (e.g., microbead, nanoparticle, or other solid surface) including a tag cassette cognate binding molecule can be used to locally activate at the site of a treatment a modified cell expressing a chimeric molecule as disclosed herein.

In certain embodiments, modified cells expressing a chimeric molecule may be detected or tracked in vivo by using ExoCBMs that specifically bind a tag cassette (e.g., anti-Tag antibodies, or Strep-tactin binding to Strep tag), which ExoCBMs for the tag cassette are conjugated to a fluorescent dye, radio-tracer, iron-oxide nanoparticle or other imaging agent known in the art for detection by X-ray, CT-scan, MRI-scan, PET-scan, ultrasound, flow-cytometry, near infrared imaging systems, or other imaging modalities (see, e.g., Yu, et al., 2012, *Theranostics* 2:3).

In further embodiments, modified cells expressing chimeric molecules of the instant disclosure may be used in diagnostic methods or imaging methods, including methods used in relation to the indications or conditions identified herein.

In other embodiments, ExoCBMs may further comprise a cytotoxic component (e.g., chemotherapeutic drugs such as anti-mitotics (e.g., vindesine), antifolates, alkylating agents (e.g., temozolomide), bacterial toxins, ricin, anti-virals, radioisotopes, radiometals), which is useful for specific killing or disabling of cells. In further embodiments, ExoCBMs may further comprise a detectable component (e.g., biotin, fluorescent moiety, radionuclide), which is useful for tracking or imaging cells. In still further embodiments, ExoCBMs may further comprise a functional component (e.g., an immunostimulatory moiety, cytokine, immune modulator, immunoglobulin protein, or the like).

Thus, modified cells expressing tag cassettes can be, e.g., more readily detected, enriched for, isolated, activated, tracked, depleted, or eliminated as compared to a modified cell without a tag cassette. That is, a tag cassette can essentially function as a handle or beacon to allow for, e.g., the detection, enrichment, isolation, activation, tracking, depletion, or elimination of cells expressing a chimeric molecule in vitro, in vivo and/or ex vivo.

In certain embodiments, a tag cassette includes from five to 500 amino acids, or from six to 100 amino acids, or from seven to 50 amino acids, or from eight to 20 amino acids. In some embodiments, a tag cassette has seven to ten amino acids. In particular embodiments, a tag cassette is non-immunogenic or minimally immunogenic. In particular embodiments, a tag cassette is immunogenic and provides adjuvant properties.

In particular embodiments, the ExoCBM can be a protein that binds the tag cassette Strep-Tag II (SEQ ID NO:1); Myc tag (SEQ ID NO:2); V5 tag (SEQ ID NO:3); Flag Tag (SEQ ID NO:4); Xpress tag (SEQ ID NO:11); Avi Tag (SEQ ID NO:12); Calmodulin Tag (SEQ ID NO:13); HA Tag (SEQ ID NO:14); Soft Tag 1 (SEQ ID NO:15); Softag 3 (SEQ ID NO:16); Strep-Tag (SEQ ID NO: 17); or Engineered Tag of a Minimal Chelation Site (SEQ ID NO: 18). In particular embodiments, an ExoCBM is a single chain Fv fragment (scFv) that includes VH and VL regions specific for the tag cassette Strep-Tag II (SEQ ID NO:1); Myc tag (SEQ ID NO:2); V5 tag (SEQ ID NO:3); Flag Tag (SEQ ID NO:4); Xpress tag (SEQ ID NO:11); Avi Tag (SEQ ID NO:12); Calmodulin Tag (SEQ ID NO:13); HA Tag (SEQ ID NO:14); Soft Tag 1 (SEQ ID NO:15); Softag 3 (SEQ ID NO:16); Strep-Tag (SEQ ID NO:17); or Engineered Tag of a Minimal Chelation Site (SEQ ID NO:18). In particular embodiments, the VH and VL regions are human.

ExoCBMs that specifically bind tag cassette sequences disclosed herein are commercially available. As non-limiting examples, Strep tag antibodies are commercially available from suppliers including Abcam, Iba, and Qiagen. His tag antibodies are commercially available from suppliers including Life Technologies, Pierce Antibodies, and GenScript. Flag tag antibodies are commercially available from suppliers including Pierce Antibodies, GenScript, and Sigma-Aldrich. Xpress tag antibodies are commercially available from suppliers including Pierce Antibodies, Life Technologies and GenScript. Avi tag antibodies are commercially available from suppliers including Pierce Antibodies, IsBio, and Genecopoeia. Calmodulin tag antibodies are commercially available from suppliers including Santa Cruz Biotechnology, Abcam, and Pierce Antibodies. HA tag antibodies are commercially available from suppliers including Pierce Antibodies, Cell Signal and Abcam. Myc tag antibodies are commercially available from suppliers including Santa Cruz Biotechnology, Abcam, and Cell Signal.

As stated, antibodies are one example of cognate binding molecules and include whole antibodies or binding fragments of an antibody, e.g., Fv, Fab, Fab', F(ab')$_2$, Fc, and single chain (sc) forms and fragments thereof that specifically bind a tag cassette. Additional examples include scFv-based grababodies and soluble VH domain antibodies. These antibodies form binding regions using only heavy chain variable regions. See, e.g., Jespers, et al., 2004, *Nat. Biotechnol.* 22:1161; Cortez-Retamozo, et al., 2004, *Cancer Res.* 64:2853; Baral, et al., 2006, *Nature Med.* 12:580; and Barthelemy, et al., 2008, *J. Biol. Chem.* 283:3639).

Antibodies or antigen binding fragments can include all or a portion of polyclonal antibodies, monoclonal antibodies, human antibodies, humanized antibodies, synthetic antibodies, chimeric antibodies, bispecific antibodies, mini bodies, and linear antibodies.

Antibodies from human origin or humanized antibodies have lowered or no immunogenicity in humans and have a lower number of non-immunogenic epitopes compared to non-human antibodies. Antibodies and their fragments will generally be selected to have a reduced level or no antigenicity in human subjects.

Antibodies that specifically bind a particular tag cassette can be prepared using methods of obtaining monoclonal antibodies, methods of phage display, methods to generate human or humanized antibodies, or methods using a transgenic animal or plant engineered to produce antibodies as is known to those of ordinary skill in the art (see, e.g., U.S. Pat. Nos. 6,291,161 and 6,291,158). Phage display libraries of partially or fully synthetic antibodies are available and can be screened for an antibody or fragment thereof that can bind to a tag cassette. For example, binding domains may be identified by screening a Fab phage library for Fab fragments that specifically bind to a tag cassette of interest (see Hoet, et al., 2005, *Nat. Biotechnol.* 23:344). Phage display libraries of human antibodies are also available. Additionally, traditional strategies for hybridoma development using a tag cassette of interest as an immunogen in convenient systems (e.g., mice, HUMAB MOUSE® (GenPharm Int'l. Inc., Mountain View, Calif.), TC MOUSE® (Kirin Pharma Co. Ltd., Tokyo, JP), KM-MOUSE® (Medarex, Inc., Princeton, N.J.), llamas, chicken, rats, hamsters, rabbits, etc.) can be used to develop ExoCBMs that specifically bind tag cassettes. In particular embodiments, ExoCBMs specifically bind to a tag cassette preferentially expressed by a modified cell type and do not cross react with nonspecific components or unrelated targets. Once identified, the amino acid sequence of the ExoCBMs and gene sequences encoding them can be isolated and/or determined.

An alternative source of ExoCBMs includes sequences that encode random peptide libraries or sequences that encode an engineered diversity of amino acids in loop regions of alternative non-antibody scaffolds, such as scTCR (see, e.g., Lake, et al., 1999, *Int. Immunol.* 11:745; Maynard, et al., 2005, *J. Immunol. Methods* 306:51; U.S. Pat. No. 8,361,794), fibrinogen domains (see, e.g., Weisel, et al., 1985, *Science* 230:1388), Kunitz domains (see, e.g., U.S. Pat. No. 6,423,498), designed ankyrin repeat proteins (DARPins; Binz, et al., *J. Mol. Biol.* 332:489, 2003 and Binz, et al., 2004, *Nat. Biotechnol.* 22:575), fibronectin binding domains (adnectins or monobodies; Richards, et al., 2003, *J. Mol. Biol.* 326:1475; Parker, et al., 2005, *Protein Eng. Des. Selec.* 18:435, and Hackel, et al. 2008, *J. Mol. Biol.* 381:1238-1252), cysteine-knot miniproteins (Vita, et al., 1995, *Proc. Nat'l. Acad. Sci.* (USA) 92:6404-6408; Martin, et al., 2002, *Nat. Biotechnol.* 21:71, and Huang, et al. 2005, *Structure* 13:755), tetratricopeptide repeat domains (Main, et al., 2003, *Structure* 11:497 and Cortajarena, et al., 2008, *ACS Chem. Biol.* 3:161), leucine-rich repeat domains (Stumpp, et al., 2003, *J. Mol. Biol.* 332:471), lipocalin domains (see, e.g., WO 2006/095164, Beste, et al., 1999, *Proc. Nat'l. Acad. Sci.* (USA) 96:1898 and Schonfeld, et al., 2009, *Proc. Nat'l. Acad. Sci.* (USA) 106:8198), V-like domains (see, e.g., U.S. Publication No. 2007/0065431), C-type lectin domains (Zelensky and Gready, 2005, *FEBS J.* 272:6179; Beavil, et al., 1992, *Proc. Nat'l. Acad. Sci.* (USA) 89:753 and Sato, et al., 2003, *Proc. Nat'l. Acad. Sci.* (USA) 100:7779), mAb2 or Fcab™ (see, e.g., WO 2007/098934 and WO 2006/072620), armadillo repeat proteins (see, e.g., Madhurantakam, et al., 2012, *Protein Sci.* 21: 1015; WO 2009/040338), affilin (Ebersbach, et al., 2007, *J. Mol. Biol.* 372: 172), affibody, avimers, knottins, fynomers, atrimers, cytotoxic T-lymphocyte associated protein-4 (Weidle, et al., 2013, *Cancer Gen. Proteo.* 10:155), or the like (Nord, et al., 1995, *Protein Eng.* 8:601; Nord, et al., 1997, *Nat. Biotechnol.* 15:772; Nord, et al., 2001, *Euro. J. Biochem.* 268:4269; Binz, et al., 2005, *Nat. Biotechnol.* 23:1257; Boersma and Pluckthun, 2011, *Curr. Opin. Biotechnol.* 22:849).

Peptide aptamers include a peptide loop (which is specific for a tag cassette) attached at both ends to a protein scaffold. This double structural constraint increases the binding affinity of peptide aptamers to levels comparable to antibodies. The variable loop length is typically 8 to 20 amino acids and the scaffold can be any protein that is stable, soluble, small, and non-toxic. Peptide aptamer selection can be made using different systems, such as the yeast two-hybrid system (e.g., Gal4 yeast-two-hybrid system), or the LexA interaction trap system.

Extracellular components can also include tag cassettes that bind endogenous cognate binding molecules (EndoCBMs). Tag cassettes that bind EndoCBMs will generally be specific to particular endogenous activation factors (e.g., growth factors, differentiation factors and/or survival factors) as described herein.

In additional embodiments, modified cells additionally express a hydrophobic portion. A "hydrophobic portion" means any amino acid sequence having a three-dimensional structure that is thermodynamically stable in a cell membrane, and generally ranges in length from 15 amino acids to 30 amino acids. The structure of a hydrophobic portion may include an alpha helix, a beta barrel, a beta sheet, a beta helix, or any combination thereof. A hydrophobic portion can be a transmembrane domain.

A hydrophobic portion contained in a chimeric molecule will allow a fusion protein to associate with a cellular membrane such that a portion of the fusion protein will be located extracellularly (e.g., a tag cassette). A hydrophobic portion will generally be disposed within the cellular membrane phospholipid bilayer.

In certain embodiments, a hydrophobic portion is a transmembrane domain. The transmembrane domain can anchor the expressed chimeric molecule to the modified cell's membrane. The transmembrane domain can be derived either from a natural and/or a synthetic source. When the source is natural, the transmembrane domain can be derived from any membrane-bound or transmembrane protein. Particular examples can be derived from an integral membrane protein (e.g., receptor, cluster of differentiation (CD) molecule, enzyme, transporter, cell adhesion molecule, or the like). Transmembrane domains can include at least the transmembrane region(s) of the alpha, beta or zeta chain of a T-cell receptor, CD8, CD27, CD28, CD3, CD45, CD4, CD5, CD9, CD16, CD22; CD33, CD37, CD64, CD80, CD86, CD134, CD137 and CD154. Transmembrane domains can include those shown in the FIGS.

In particular embodiments, the transmembrane domain includes the amino acid sequence of the CD28 transmembrane domain as shown in FIG. 2 (SEQ ID NO: 45) or the amino acid sequence of the CD4 transmembrane domain.

Extracellular components of expressed chimeric molecules can also include spacer regions, linker sequences and/or junction amino acids.

Spacer regions can facilitate the interaction of tag cassettes with CBMs, including ExoCBMs. Thus, in particular embodiments, a spacer region is found between the tag cassette and hydrophobic portion of an expressed chimeric molecule. In particular embodiments, the spacer region is part of the extracellular component of an expressed chimeric molecule.

The length of a spacer region can be customized for individual tag cassettes on modified cells to optimize recognition by CBMs, including ExoCBMs. In particular embodiments, a spacer region length can be selected based upon the location of a tag cassette, affinity of an ExoCBM for the tag cassette, and/or the ability of the modified cells expressing the molecule to proliferate in vitro, in vivo and/or ex vivo in response to CBM/tag cassette binding.

Typically a spacer region is found between the tag cassette and a hydrophobic portion of an expressed chimeric molecule. Spacer regions can provide for flexibility of the tag cassette and allow for high expression levels in modified cells. In particular embodiments, a spacer region can have at least 10 to 250 amino acids, at least 10 to 200 amino acids, at least 10 to 150 amino acids, at least 10 to 100 amino acids, at least 10 to 50 amino acids, or at least 10 to 25 amino acids. In further embodiments, a spacer region has 250 amino acids or less; 200 amino acids or less, 150 amino acids or less; 100 amino acids or less; 50 amino acids or less; 40 amino acids or less; 30 amino acids or less; 20 amino acids or less; or 10 amino acids or less.

In particular embodiments, spacer regions can include or be derived from a hinge region of an immunoglobulin like molecule, e.g., all or a portion of the hinge region from a human IgG1, IgG2, IgG3, or IgG4. Hinge regions can be modified to avoid undesirable structural interactions such as dimerization. In particular embodiments, all or a portion of a hinge region can be combined with one or more domains of a constant region of an immunoglobulin. For example, a portion of a hinge region can be combined with all or a portion of a CH2 or CH3 domain. In particular embodiments, the spacer region does not include the 47-48 amino acid hinge region sequence from CD8a.

In particular embodiments, the spacer region is selected from the group including a hinge region sequence from IgG1, IgG2, IgG3, or IgG4 in combination with all or a portion of a CH2 region; all or a portion of a CH3 region; or all or a portion of a CH2 region and all or a portion of a CH3 region.

In particular embodiments, a short spacer region has 12 amino acids or less and includes all or a portion of a IgG4 hinge region sequence (FIG. 2, SEQ ID NO: 42), an intermediate spacer region has 119 amino acids or less and includes all or a portion of a IgG4 hinge region sequence and a CH3 region (e.g., FIG. 3; SEQ ID NO:31), and a long spacer has 229 amino acids or less and includes all or a portion of a IgG4 hinge region sequence, a CH2 region, and a CH3 region (e.g., FIG. 3; SEQ ID NO:30).

In particular embodiments, a "hinge region" or a "hinge" refers to (a) an immunoglobulin hinge sequence (made up of, e.g., upper and core regions) or a functional fragment or variant thereof, (b) a type II C-lectin interdomain (stalk) region or a functional fragment or variant thereof, or (c) a cluster of differentiation (CD) molecule stalk region or a functional variant thereof. A "wild type immunoglobulin hinge region" refers to a naturally occurring upper and middle hinge amino acid sequences interposed between and connecting the CH1 and CH2 domains (e.g., for IgG, IgA, and IgD) or interposed between and connecting the CH1 and CH3 domains (e.g., for IgE and IgM) found in the heavy chain of an antibody. In certain embodiments, a hinge region is human, and in particular embodiments, includes a human IgG hinge region.

A "stalk region" of a type II C-lectin or CD molecule refers to the portion of the extracellular domain of the type II C-lectin or CD molecule that is located between the C-type lectin-like domain (CTLD; e.g., similar to CTLD of natural killer cell receptors) and the hydrophobic portion (e.g., a transmembrane domain). For example, the extracellular domain of human CD94 (GenBank Accession No. AAC50291.1) corresponds to amino acid residues 34-179, but the CTLD corresponds to amino acid residues 61-176, so the stalk region of the human CD94 molecule includes amino acid residues 34-60, which are located between the hydrophobic portion (e.g., transmembrane domain) and CTLD (see Boyington, et al., 1999, *Immunity* 10:75; for descriptions of other stalk regions, see also Beavil, et al., 1992, *Proc. Nat'l. Acad. Sci. USA* 89:753; and Figdor, et al., 2002, *Nat. Rev. Immunol.* 2:77). These type II C-lectin or CD molecules may also have junction amino acids between the stalk region and the transmembrane region or the CTLD. In another example, the 233 amino acid human NKG2A protein (GenBank Accession No. P26715.1) has a hydrophobic portion (e.g., a transmembrane domain) ranging from amino acids 71-93 and an extracellular domain ranging from amino acids 94-233. The CTLD includes amino acids 119-231, and the stalk region includes amino acids 99-116, which may be flanked by additional junction amino acids. Other type II C-lectin or CD molecules, as well as their extracellular binding domains, stalk regions, and CTLDs are known in the art (see, e.g., GenBank Accession Nos. NP_001993.2; AAH07037.1; NP_001773.1; AAL65234.1; CAA04925.1; for the sequences of human CD23, CD69, CD72, NKG2A and NKG2D and their descriptions, respectively).

A "derivative" of a stalk region hinge, or fragment thereof, of a type II C-lectin or CD molecule includes an eight to 150 amino acid sequence in which one, two, or three amino acids of the stalk region of a wild type II C-lectin or CD molecule have a deletion, insertion, substitution, or any combination thereof. For instance, a derivative can include one or more amino acid substitutions and/or an amino acid deletion. In certain embodiments, a derivative of a stalk region is more resistant to proteolytic cleavage as compared to the wild-type stalk region sequence, such as those derived from eight to 20 amino acids of NKG2A, NKG2D, CD23, CD64, CD72, or CD94.

In certain embodiments, stalk region hinges may include from seven to 18 amino acids and can form an α-helical coiled coil structure. In certain embodiments, stalk region hinges contain 0, 1, 2, 3, or 4 cysteines. Exemplary stalk region hinges include fragments of the stalk regions, such as those portions including from ten to 150 amino acids from the stalk regions of CD69, CD72, CD94, NKG2A and NKG2D.

Alternative hinges that can be used in chimeric molecules are from portions of cell surface receptors (interdomain regions) that connect immunoglobulin V-like or immunoglobulin C-like domains. Regions between Ig V-like domains where the cell surface receptor contains multiple Ig V-like domains in tandem and between Ig C-like domains where the cell surface receptor contains multiple tandem Ig C-like regions are also contemplated as hinges useful in chimeric molecules. In certain embodiments, hinge sequences including cell surface receptor interdomain regions may further contain a naturally occurring or added motif, such as an IgG core hinge sequence to provide one or more disulfide bonds to stabilize the chimeric molecule dimer formation. Additional examples of hinges include interdomain regions between the Ig V-like and Ig C-like regions of CD2, CD4, CD22, CD33, CD48, CD58, CD66, CD80, CD86, CD150, CD166, and CD244.

In certain embodiments, hinge sequences include 5 to 150 amino acids, 5 to 10 amino acids, 10 to 20 amino acids, 20 to 30 amino acids, 30 to 40 amino acids, 40 to 50 amino acids, 50 to 60 amino acids, 5 to 60 amino acids, 5 to 40 amino acids, for instance, 8 to 20 amino acids or 10 to 15 amino acids. The hinges may be primarily flexible, but may also provide more rigid characteristics or may contain primarily α-helical structure with minimal β-sheet structure.

In certain embodiments, a hinge sequence is stable in plasma and serum, and is resistant to proteolytic cleavage. For example, the first lysine in an IgG1 upper hinge region may be mutated or deleted to minimize proteolytic cleavage, and hinges may include junction amino acids. In some embodiments, a hinge sequence may contain a naturally occurring or added motif, such as an immunoglobulin hinge core structure CPPCP (SEQ. ID. NO. 8) that confers the capacity to form a disulfide bond or multiple disulfide bonds to stabilize dimer formation.

In certain embodiments, an expressed chimeric molecule may include a "linker sequence" that is an amino acid sequence having from two up to 500 amino acids, which can provide flexibility and room for conformational movement between two regions, domains, motifs, cassettes or modules connected by a linker. Exemplary linker sequences include those having from one to ten repeats of $Gly_xSer_y$, wherein x and y are independently an integer from 0 to 10 provided that x and y are not both 0 (e.g., $(Gly_4Ser)_2$ (e.g., SEQ ID NO:5), $(Gly_3Ser)_2$ (e.g., SEQ ID NO:6), $Gly_2Ser$, or a combination thereof such as $(Gly_3Ser)_2Gly_2Ser)$(e.g., SEQ ID NO:7). In certain other embodiments, a connector region may have a linker sequence that includes one or more immunoglobulin heavy chain constant regions, such as a CH3 alone or a CH2CH3 sequence.

Linker sequences often provide junction amino acids. Junction amino acids refer to one or more (e.g., 2-20) amino acid residues between two adjacent motifs, regions or domains of a polypeptide, such as between a tag cassette or a spacer and a hydrophobic portion. Junction amino acids may result from the construct design of a fusion protein (e.g., amino acid residues resulting from use of a restriction enzyme site during the construction of a nucleic acid molecule encoding a fusion protein). For example, a single junction amino acid, asparagine, can be encoded by the AAT codon between a nucleic acid sequence encoding a secretory signal sequence and the sequence encoding a tag cassette. Similarly, an asparagine (N) junction amino acid can be found between a flexible linker amino acid sequence of GGSGSG (SEQ ID NO:10) and the amino acid tag sequence SEQ ID NO:1.

In particular embodiments, an expressed chimeric molecule may include a hinge and one or more linker sequences, or an expressed chimeric molecule may include a hinge, one or more linker sequences, and one or more tag cassettes. In particular embodiments, expressed chimeric molecules can vary in length, for instance, from five to 500 amino acids, or from ten to 350 amino acids, or from 15 to 100 amino acids, or from 20 to 75 amino acids, or from 25 to 35 amino acids.

Within a chimeric molecule structure, a tag cassette may be located (a) immediately amino-terminal to a spacer region, linker sequence, junction amino acid or hydrophobic portion, (b) interposed between and connecting a spacer region, linker sequence, junction amino acid or hydrophobic portion, and/or (c) immediately carboxy-terminal to a spacer region, linker sequence, junction amino acid or hydrophobic portion. In certain embodiments, one or more junction amino acids may be disposed between and connecting a tag cassette with a hydrophobic portion, or disposed between and connecting a tag cassette with a linker sequence.

In further embodiments, the two or more first tag cassettes may be located in different areas of a chimeric molecule. In certain embodiments, a first tag cassette is located at the amino-terminus.

In certain embodiments, a linker sequence can be adjacent to a tag cassette, wherein the linker sequence with the tag cassette has an amino acid sequence of (Gly-Gly-Gly-Gly-Ser)$_2$-Trp-Ser-His-Pro-Gln-Phe-Glu-Lys (SEQ ID NO:19), Trp-Ser-His-Pro-Gln-Phe-Glu-Lys-(Gly-Gly-Gly-Gly-Ser)$_2$ (SEQ ID NO:20), (Gly-Gly-Gly-Gly-Ser)$_2$-Trp-Ser-His-Pro-Gln-Phe-Glu-Lys-(Gly-Gly-Gly-Ser)$_2$-Gly-Gly-Ser-Trp-Ser-His-Pro-Gln-Phe-Glu-Lys (SEQ ID NO:21), Trp-Ser-His-Pro-Gln-Phe-Glu-Lys-(Gly-Gly-Gly-Ser)$_2$-Gly-Gly-Ser-Trp-Ser-His-Pro-G n-Phe-Glu-Lys-(Gly-Gly-Gly-Gly-Ser)$_2$ (SEQ ID NO:22), (Gly-Gly-Gly-Gly-Ser)$_2$-Trp-Ser-His-Pro-Gln-Phe-Glu-Lys-(Gly-Gly-Gly-Ser)$_2$-Gly-Gly-Ser-Trp-Ser-His-Pro-Gln-Phe-Glu-Lys-(Gly-Gly-Gly-Gly-Ser)$_2$-Trp-Ser-His-Pro-Gln-Phe-Glu-Lys (SEQ ID NO:23), or Trp-Ser-His-Pro-Gln-Phe-Glu-Lys-(Gly-Gly-Gly-Gly-Ser)$_2$-Trp-Ser-His-Pro-Gln-Phe-Glu-Lys-(Gly-Gly-Gly-Ser)$_2$-Gly-Gly-Ser-Trp-Ser-His-Pro-Gln-Phe-Glu-Lys-(Gly-Gly-Gly-Gly-Ser)$_2$ (SEQ ID NO:24).

In additional embodiments, modified cells express an intracellular component. The hydrophobic portion can link the tag cassette of an extracellular component to an intracellular component that can direct actions of the genetically modified cell when the tag cassette is bound by a cognate binding molecule. Accordingly, intracellular components of expressed chimeric molecules can include effector domains. Effector domains are capable of transmitting functional signals to a cell. In particular embodiments, an effector domain will directly or indirectly promote a cellular response by associating with one or more other proteins that directly promote a cellular response. Effector domains can provide for activation of at least one function of a modified cell upon binding to the tag cassette. Activation of the modified cell can include one or more of expansion, differentiation, and/or activation of effector functions.

An effector domain can include one, two, three or more receptor signaling domains, intracellular signaling domains (e.g., cytoplasmic signaling sequences), costimulatory domains, or combinations thereof. Exemplary effector domains include signaling and stimulatory domains selected from: 4-1BB, CARD11, CD3 gamma, CD3 delta, CD3 epsilon, CD3ζ, CD27, CD28, CD79A, CD79B, DAP10, FcRα, FcRβ, FcRγ, Fyn, HVEM, ICOS, LAG3, LAT, Lck, LRP, NKG2D, NOTCH1, pTα, PTCH2, OX40, ROR2, Ryk, SLAMF1, Slp76, TCRα, TCRβ, TRIM, Wnt, Zap70, or any combination thereof.

Primary cytoplasmic signaling sequences that act in a stimulatory manner may contain signaling motifs which are known as receptor tyrosine-based activation motifs or iTAMs. Examples of iTAM containing primary cytoplasmic signaling sequences include those derived from CD3γ, CD3δ, CD3ε, CD3ζ, CD5, CD22, CD66d, CD79a, CD79b, and FeR gamma. In particular embodiments, variants of CD3ζ retain at least one, two, three, or all ITAM regions as shown in FIG. 2 (SEQ ID NO: 49-51).

In particular embodiments, an effector domain includes a cytoplasmic portion that associates with a cytoplasmic signaling protein, wherein the cytoplasmic signaling protein is a lymphocyte receptor or signaling domain thereof, a protein including a plurality of ITAMs, a costimulatory domain, or any combination thereof.

Examples of intracellular signaling domains include the cytoplasmic sequences of the CD3ζ chain, and/or co-receptors that act in concert to initiate signal transduction following engagement.

In particular embodiments, an intracellular signaling domain of a molecule expressed by a modified cell can be designed to include an intracellular signaling domain combined with any other desired cytoplasmic domain(s). For example, the intracellular signaling domain of a molecule can include an intracellular signaling domain and a costimulatory domain, such as a costimulatory signaling region.

The costimulatory signaling region refers to a portion of the molecule including the intracellular domain of a costimulatory domain. A costimulatory domain is a cell surface molecule that can be required for a cellular response to cognate molecule binding. Examples of such molecules include CD27, CD28, 4-1BB (CD 137; e.g., as in FIG. 2), OX40, CD30, CD40, lymphocyte function-associated antigen-1 (LFA-1), CD2, CD7, LIGHT, NKG2C, B7-H3, and a ligand that specifically binds with CD83.

In particular embodiments, the amino acid sequence of the intracellular signaling domain includes a variant of CD3ζ and a portion of the 4-1BB intracellular signaling domain as provided in FIG. 3 (SEQ ID NO: 53).

In particular embodiments, the intracellular signaling domain includes (i) all or a portion of the signaling domain of CD3ζ, (ii) all or a portion of the signaling domain of CD28, (iii) all or a portion of the signaling domain of 4-1BB, or (iv) all or a portion of the signaling domain of CD3ζ, CD28 and/or 4-1BB.

Additional exemplary effector domains useful in the chimeric molecules of this disclosure may be from a protein of a Wnt signaling pathway (e.g., LRP, Ryk, ROR2), NOTCH signaling pathway (e.g., NOTCH1, NOTCH2, NOTCH3, NOTCH4), Hedgehog signaling pathway (e.g., PTCH, SMO), receptor tyrosine kinases (RTKs) (e.g., epidermal growth factor (EGF) receptor family, fibroblast growth factor (FGF) receptor family, hepatocyte growth factor (HGF) receptor family, Insulin receptor (IR) family, platelet-derived growth factor (PDGF) receptor family, vascular endothelial growth factor (VEGF) receptor family, tropomycin receptor kinase (Trk) receptor family, ephrin (Eph) receptor family, AXL receptor family, leukocyte tyrosine kinase (LTK) receptor family, tyrosine kinase with immunoglobulin-like and EGF-like domains 1 (TIE) receptor family, receptor tyrosine kinase-like orphan (ROR) receptor family, discoidin domain (DDR) receptor family, rearranged during transfection (RET) receptor family, tyrosine-protein kinase-like (PTK7) receptor family, related to receptor tyrosine kinase (RYK) receptor family, muscle specific kinase (MuSK) receptor family); G-protein-coupled receptors, GPCRs (Frizzled, Smoothened); serine/threonine kinase receptors (BMPR, TGFR); or cytokine receptors (IL1R, IL2R, IL7R, IL15R).

As will be understood by one of ordinary skill in the art, selection of particular intracellular components and effector domains will depend on the intended use of a modified cell in its undifferentiated and/or differentiated state.

The intracellular signaling domain sequences of the expressed chimeric molecule can be linked to each other in a random or specified order. Optionally, a short oligo- or protein linker, preferably between 2 and 10 amino acids in length may form the linkage.

Thus, an effector domain contained in a chimeric molecule will be an intracellular component and capable of transmitting functional signals to a cell. In certain embodiments, a single chain chimeric molecule will dimerize with a second single chain chimeric molecule, respectively, wherein the dimerization allows the intracellular component including an effector domains to be in close proximity and promote signal transduction when exposed to the proper signal. As indicated, in addition to forming such dimer protein complexes, the effector domains may further associate with other signaling factors, such as costimulatory factors, to form multiprotein complexes that produce an intracellular signal. In certain embodiments, an effector domain will indirectly promote a cellular response by associating with one or more other proteins that directly promote a cellular response. An effector domain may include one, two, three or more receptor signaling domains, costimulatory domains, or combinations thereof. Any intracellular component including an effector domain, costimulatory domain or both from any of a variety of signaling molecules (e.g., signal transduction receptors) may be used in the fusion proteins of this disclosure.

The design of particular molecules to be expressed by the modified cells can be customized depending on the type of tag cassette, and/or the intracellular signaling domain, when present. In particular embodiments, a number of constructs are tested in vitro and in in vivo models to determine the ability of modified cells to expand in culture and/or differentiate. In particular embodiments, a molecule is selected that provides for capability of at least 30% of modified-differentiated cells to proliferate through at least two generations in vitro and/or within 72 hours after introduction in vivo. In particular embodiments, a molecule is not selected that results in greater than 50% of the cells undergoing activation induced cell death (AICD) within 72 hours in vivo in immunodeficient mice.

Stem Cells. As used herein the term "stem cells" has its ordinary meaning in the art and refers to totipotent stem cells, pluripotent stem cells (including induced pluripotent stem cells) and multipotent stem cells. Stem cells include embryonic stem cells, as well as, without limitation, all other types of stem cells referenced herein.

"Embryonic stem cells" or "ES cells" or "ESCs" refer to undifferentiated ESCs that have the ability to integrate into and become part of the germ line of a developing embryo. ESCs are capable of differentiating into any tissue or organ. ESCs that are suitable for use herein include cells from the J1 ES cell line, 129J ES cell line, murine stem cell line D3 (American Type Culture Collection), the R1 or E14K cell lines derived from 129/Sv mice, cell lines derived from Balb/c and C57Bl/6 mice, and human (h) ESCs (e.g. from WiCell Research Institute, WI; or ES cell International, Melbourne, Australia).

ESCs can differentiate into the mesoderm, endoderm and ectoderm. Mesodermal stem cells further differentiate into cell types including cardiac muscle cells, skeletal muscle cells, tubule cells of the kidney, red blood cells, and smooth muscle cells in the gut. Endodermal stem cells further differentiate into cell types including lung cells (e.g., alveolar cells), thyroid cells, and pancreatic cells. Ectodermal stem cells further differentiate into cell types including skin cells of the epidermis, neuron cells, and pigment cells. Thus, the central nervous system, hair, and the epidermis are all derived from ectodermal stem cells. Mesenchymal stem cells differentiate into bone, cartilage, adipose tissue, muscle, tendon, ligament, neural tissue and others.

"Umbilical cord blood-derived mesenchymal stem cells" refer to mesenchymal stem cells isolated from an umbilical cord blood of a mammal.

A neural stem cell is an undifferentiated neural cell that is capable of self-maintenance, meaning that with each cell division, one daughter cell will also be a stem cell. The non-stem cell progeny of a neural stem cell are neural progenitor cells. Neural progenitor cells generated from a neural stem cell are capable of differentiating into neurons, astrocytes (type I and type II) and oligodendrocytes (astrocytes and oligodendrocytes are collectively called glia or glial cells) and/or Schwann cells. Hence, neural stem cells are pluripotent because their progeny have multiple differentiating pathways. Pluripotent neural stem cells may be obtained from embryonic or adult neural tissue and cultured by means known in the art, briefly summarized below for convenience.

Hematopoietic Stem/Progenitor Cells or HSPC refer to hematopoietic stem cells and/or hematopoietic progenitor cells. "Hematopoietic stem cells" refer to undifferentiated hematopoietic cells that are capable of self-renewal either in vivo, essentially unlimited propagation in vitro, and capable of differentiation to other cell types. A "hematopoietic progenitor cell" is a cell derived from hematopoietic stem cells or fetal tissue that is capable of further differentiation into mature cells types. In certain embodiments, hematopoietic progenitor cells are $CD24^{lo}$ $Lin^-$ $CD117^+$ hematopoietic progenitor cells. HSPC can self-renew or can differentiate into (i) myeloid progenitor cells which ultimately give rise to monocytes and macrophages, neutrophils, basophils, eosinophils, erythrocytes, megakaryocytes/platelets, or dendritic cells; or (ii) lymphoid progenitor cells which ultimately give rise to T-cells, B-cells, and lymphocyte-like cells called natural killer cells (NK-cells). For a general discussion of hematopoiesis and HSPC differentiation, see Chapter 17, Differentiated Cells and the Maintenance of Tissues, Alberts, et al., 1989, Molecular Biology of the Cell, 2nd Ed., Garland Publishing, New York, N.Y.; Chapter 2 of Regenerative Medicine, Department of Health and Human Services, Aug. 5, 2006, and Chapter 5 of Hematopoietic Stem Cells, 2009, Stem Cell Information, Department of Health and Human Services.

Exemplary sources of stem cells include umbilical cord blood, placental blood, and peripheral blood (see U.S. Pat. Nos. 5,004,681; 7,399,633; and 7,147,626; Craddock, et al., 1997, *Blood* 90(12):4779-4788; Jin, et al., 2008, *Journal of Translational Medicine* 6:39; Pelus, 2008, *Curr. Opin. Hematol.* 15(4):285-292; Papayannopoulou, et al., 1998, *Blood* 91(7):2231-2239; Tricot, et al., 2008, *Haematologica* 93(11):1739-1742; and Weaver, et al., 2001, *Bone Marrow Transplantation* 27(2):S23-S29). Methods regarding collection, anti-coagulation and processing, etc. of blood samples can be found in, e.g., Alsever, et al., 1941, *N.Y. St. J. Med.* 41:126; De Gowin, et al., 1940, *J. Am. Med. Ass.* 114:850; Smith, et al., 1959, *J. Thorac. Cardiovasc. Surg.* 38:573; Rous and Turner, 1916, *J. Exp. Med.* 23:219; and Hum, 1968, Storage of Blood, Academic Press, New York, pp. 26-160. Sources of stem cells also include bone marrow (see Kodo, et al., 1984, *J. Clin Invest.* 73:1377-1384), embryonic cells, aortal-gonadal-mesonephros derived cells, lymph, liver, thymus, and spleen from age-appropriate donors. All collected samples of stem cells can be screened for undesirable components and discarded, treated, or used according to accepted current standards at the time.

Stem cells initially can be collected and isolated from a sample using any appropriate technique. Appropriate collection and isolation procedures include magnetic separation; fluorescence activated cell sorting (FACS; Williams, et al., 1985, *J. Immunol.* 135:1004; Lu, et al., 1986, *Blood* 68(1):126-133); affinity chromatography; cytotoxic agents joined to a monoclonal antibody or used in conjunction with a monoclonal antibody, e.g., complement and cytotoxins; "panning" with antibody attached to a solid matrix (Broxmeyer, et al., 1984, *J. Clin. Invest.* 73:939-953); and/or selective agglutination using a lectin such as soybean (Reisner, et al., 1980, *Proc. Natl. Acad. Sci.* U.S.A. 77:1164); etc.

In particular embodiments, a stem cell sample (e.g., a fresh cord blood unit) initially can be processed to select/enrich for a selected stem cell type using appropriate anti-stem cell marker antibodies directly or indirectly conjugated to magnetic particles in connection with a magnetic cell separator, e.g., the CLINIMACS® Cell Separation System (Miltenyi Biotec, Bergisch Gladbach, Germany). See also, sec. 5.4.1.1 of U.S. Pat. No. 7,399,633 which describes enrichment of $CD34^+$ HSPC from 1-2% of a normal bone marrow cell population to 50-80% of the population.

Following isolation and/or enrichment, stem cells can be expanded in order to increase their number. Isolation and/or expansion methods are described in, e.g., U.S. Pat. Nos. 7,399,633 and 5,004,681; U.S. Publication No. 2010/0183564; International Patent Publication Nos. (WO) WO 2006/047569; WO 2007/095594; WO 2011/127470; and WO 2011/127472; Varnum-Finney, et al., 1993, *Blood* 101: 1784-1789; Delaney, et al., 2005, *Blood* 106:2693-2699; Ohishi, et al., 2002, *J. Clin. Invest.* 110:1165-1174; Delaney, et al., 2010, *Nature Med.* 16(2): 232-236; and Chapter 2 of Regenerative Medicine, Department of Health and Human Services, August 2006, and the references cited therein. Each of the referenced methods of collection, isolation, and expansion can be used in particular embodiments of the disclosure.

Preferred methods of expanding stem cells include expansion with a Notch agonist. For information regarding expansion of stem cells using Notch agonists, see sec. 5.1 and 5.3 of U.S. Pat. Nos. 7,399,633; 5,780,300; 5,648,464; 5,849,869; and 5,856,441; WO 1992/119734; Schlondorfiand Blobel, 1999, *J. Cell Sci.* 112:3603-3617; Olkkonen and Stenmark, 1997, *Int. Rev. Cytol.* 176:1-85; Kopan, et al., 2009, *Cell* 137:216-233; Rebay, et al., 1991, *Cell* 67:687-699 and Jarriault, et al., 1998, *Mol. Cell. Biol.* 18:7423-7431. In particular embodiments, the Notch agonist is immobilized during expansion.

Notch agonists include any compound that binds to or otherwise interacts with Notch proteins or other proteins in the Notch pathway such that Notch pathway activity is promoted. Exemplary Notch agonists are the extracellular binding ligands Delta and Serrate (e.g., Jagged), RBP JϰI Suppressor of Hairless, Deltex, Fringe, or fragments thereof which promote Notch pathway activation. Nucleic acid and amino acid sequences of Delta family members and Serrate family members have been isolated from several species and are described in, e.g., WO 1993/12141; WO 1996/27610; WO 1997/01571; and Gray, et al., 1999, *Am. J. Path.* 154:785-794.

In particular embodiments, the Notch agonist is $Delta1^{ext-IgG}$. In particular embodiments, $Delta1^{ext-IgG}$ is applied to a solid phase at a concentration between 0.2 and 20 µg/ml, between 1.25 and 10 µg/ml, or between 2 and 6 µg/ml.

In particular embodiments, during expansion, stem cells are cultured in the presence of a Notch agonist and an aryl hydrocarbon receptor antagonist. The Notch agonist can be immobilized and the aryl hydrocarbon receptor antagonist can be in a fluid contacting the cells.

Additional culture conditions can include expansion in the presence of one more growth factors, such as: angiopoietin-like proteins (Angptls, e.g., Angptl2, Angptl3, Angptl7, Angptl5, and Mfap4); erythropoietin; fibroblast growth factor-1 (FGF-1); Flt-3 ligand (Flt-3L); granulocyte colony stimulating factor (G-CSF); granulocyte-macrophage colony stimulating factor (GM-CSF); insulin growth factor-2 (IFG-2); interleukin-3 (IL-3); interleukin-6 (IL-6); interleukin-7 (IL-7); interleukin-11 (IL-11); stem cell factor (SCF; also known as the c-kit ligand or mast cell growth factor); thrombopoietin (TPO); and analogs thereof (wherein the analogs include any structural variants of the growth factors having the biological activity of the naturally occurring growth factor; see, e.g., WO 2007/1145227 and U.S. Publication No. 2010/0183564).

In particular embodiments, the amount or concentration of growth factors suitable for expanding stem cells is the amount or concentration effective to promote proliferation of stem cells, but substantially no differentiation of the stem cells. Cell populations are also preferably expanded until a sufficient number of cells are obtained to provide for at least one infusion into a human subject, typically around $10^4$ cells/kg to $10^9$ cells/kg.

The amount or concentration of growth factors suitable for expanding stem cells depends on the activity of the growth factor preparation, and the species correspondence between the growth factors and stem cells, etc. Generally, when the growth factor(s) and stem cells are of the same species, the total amount of growth factor in the culture medium ranges from 1 ng/ml to 5 µg/ml, from 5 ng/ml to 1 µg/ml, or from 5 ng/ml to 250 ng/ml. In additional embodiments, the amount of growth factors can be in the range of 5-1000 or 50-100 ng/ml.

In particular embodiments, the foregoing growth factors are present in the culture condition for expanding stem cells at the following concentrations: 25-300 ng/ml SCF, 25-300 ng/ml Flt-3L, 25-100 ng/ml TPO, 25-100 ng/ml IL-6 and 10 ng/ml IL-3. In more specific embodiments, 50, 100, or 200 ng/ml SCF; 50, 100, or 200 ng/ml of Flt-3L; 50 or 100 ng/ml TPO; 50 or 100 ng/ml IL-6; and 10 ng/ml IL-3 can be used.

In particular embodiments, stem cells can be expanded by exposing them to an immobilized Notch agonist, and 50 ng/ml or 100 ng/ml SCF; to an immobilized Notch agonist, and 50 ng/ml or 100 ng/ml of each of Flt-3L, IL-6, TPO, and SCF; or an immobilized Notch agonist, and 50 ng/ml or 100 ng/ml of each of Flt-3L, IL-6, TPO, and SCF, and 10 ng/ml of IL-11 or IL-3.

Stem cells can be expanded in a tissue culture dish onto which an extracellular matrix protein such as fibronectin (FN), or a fragment thereof (e.g., CH-296 (Dao, et. al., 1998, *Blood* 92(12):4612-21)) or RETRONECTIN® (a recombinant human fibronectin fragment; Clontech Laboratories, Inc., Madison, Wis.) is bound.

Modified Stem Cells. As stated, stem cells are modified to express a tag cassette. The tag cassette can bind an exogenous cognate binding molecule (ExoCBM) or an endogenous cognate binding molecule (EndoCBM). Stem cells can also be modified to express (i) a hydrophobic portion; and (ii) an intracellular component. Various components of the expressed chimeric molecules can be linked directly or through spacer region(s), linker sequence(s) and/or junction amino acids. As will be understood by one of ordinary skill in the art, classification as a spacer region(s), linker sequence(s), junction amino acid and/or hydrophobic portion is not mutually exclusive, and there can be overlap between these functions.

Particular embodiments include modified stem cells expressing a chimeric molecule including (i) an extracellular component including a tag cassette; (ii) a hydrophobic component, and (iii) optionally an intracellular component connected to the extracellular component through the hydrophobic portion, wherein the extracellular component includes a tag cassette, and a hinge, and wherein the intracellular component includes an effector domain.

Particular embodiments include a method for targeting (e.g., for detection, enrichment, activation) a modified cell, such as a modified stem cell, including contacting the cell with a ExoCBM molecule specific for a tag cassette expressed by the cell, wherein the cell includes a nucleic acid molecule encoding a fusion protein to express the tag cassette and wherein the ExoCBM specific for the tag cassette is attached to a solid surface.

Particular embodiments include a method for promoting modified cell activation, such as modified stem cell enrichment and expansion including contacting the cell with (i) an ExoCBM specific for a tag cassette expressed by the cell and (ii) a growth factor cytokine for a time sufficient to allow cell expansion, wherein the cell includes a nucleic acid molecule including the tag cassette and the ExoCBM specific for the tag cassette is attached to a solid surface.

Particular embodiments include a method for detecting a modified cell, such as a modified stem cell, including contacting a sample including a modified cell with an ExoCBM specific for a tag cassette expressed by the modified cell wherein the ExoCBM specific for the tag cassette includes a detectable moiety, and detecting the presence of the modified cell.

Particular embodiments include a method for enriching for or isolating a modified cell, including contacting a sample including a modified cell with an ExoCBM specific for a tag cassette expressed by the modified cell, wherein the ExoCBM specific for the tag cassette includes a detectable moiety, and enriching for or isolating the modified cell expressing the tag cassette away from other cells not expressing the tag cassette in the sample.

In certain aspects, the present disclosure provides a single chain fusion protein, referred to as a chimeric molecule, which includes an extracellular component and an intracellular component connected by a hydrophobic portion, wherein the extracellular component includes a tag cassette and a hinge, and wherein the intracellular component includes an effector domain. In certain embodiments, an extracellular component further includes a linker sequence and one or more tag cassettes. In certain other embodiments, one or more tag cassettes are linked via linker sequences.

In further chimeric molecule embodiments, the fusion protein includes from amino-terminus to carboxy-terminus: a tag cassette, a hinge, a hydrophobic portion, and an intracellular component including an effector domain. In yet further chimeric molecule embodiments, the fusion protein includes from amino-terminus to carboxy-terminus: a first tag cassette, a second tag cassette, a hinge, a hydrophobic portion, and an intracellular component including an effector domain. In even further chimeric molecule embodiments, the fusion protein includes from amino-terminus to carboxy-terminus: a first tag cassette, a second tag cassette, a third tag cassette, a hinge, a hydrophobic portion, and an intracellular component including an effector domain. Each of the described embodiments can additionally include spacer regions, linker sequences and/or junction amino acids interposed between the stated components and/or at the amino terminus.

Modified stem cells or differentiated cells can additionally utilize positive and/or negative selection markers. For example, positive selectable markers may be encoded by a gene, which upon being introduced into the modified cell, expresses a dominant phenotype permitting positive selection of cells carrying the gene. Genes of this type include, hygromycin-B phosphotransferase gene (hph) which confers resistance to hygromycin B, the amino glycoside phosphotransferase gene (neo or aph) from Tn5 which codes for resistance to the antibiotic 0418, the dihydrofolate reductase (DHFR) gene, the adenosine deaminase gene (ADA), and the multi-drug resistance (MDR) gene.

In particular embodiments, functional genes can be introduced into the modified stem cells or differentiated functional cells to allow for negative selection in vivo. "Negative selection" means that an administered cell can be eliminated as a result of a change in the in vivo condition of a subject. The negative selectable phenotype can result from the insertion of a gene that confers sensitivity to an administered agent. Negative selectable genes include: the Herpes simplex virus type I thymidine kinase (HSV-I TK) gene which confers ganciclovir sensitivity; the cellular hypoxanthine phosphribosyltransferase (HPRT) gene, the cellular adenine phosphoribosyltransferase (APRT) gene, and bacterial cytosine deaminase. For additional supporting disclosure regarding negative selection, see Lupton S. D., et. al., *Mol. and Cell. Biol.* 11:6 (1991); Riddell, et al., *Human Gene Therapy* 3:319-338 (1992); WO 1992/008796 and WO 1994/028143 and U.S. Pat. No. 6,040,177 at columns 14-17).

Modified stem cells can be made recombinant by the introduction of a recombinant gene sequence into the stem cell. A description of genetically engineered stem cells can be found in sec. 5.1 of U.S. Pat. No. 7,399,633. A gene whose expression is desired in the modified cell is introduced into the cell such that it is expressible by the cells and/or their progeny.

Desired genes can be introduced into stem cells by any method known in the art, including transfection, electroporation, microinjection, lipofection, calcium phosphate mediated transfection, infection with a viral or bacteriophage vector containing the gene sequences, cell fusion, chromosome-mediated gene transfer, microcell-mediated gene transfer, sheroplast fusion, etc. Numerous techniques are known in the art for the introduction of foreign genes into cells (see e.g., Loeffler and Behr, 1993, *Meth. Enzymol.* 217:599-618; Cohen, et al., 1993, *Meth. Enzymol.* 217:618-644; Cline, 1985, *Pharmac. Ther.* 29:69-92) and may be used, provided that the necessary developmental and physiological functions of the recipient cells are not disrupted. The technique should provide for the stable transfer of the gene to the cell, so that the gene is expressible by the cell and preferably heritable and expressible by its cell progeny. As indicated, in particular embodiments, the method of transfer includes the transfer of a selectable tag cassette to the cells. The cells are then placed under selection to enrich for or isolate those cells that have taken up and are expressing the transferred gene.

The term "gene" refers to a nucleic acid sequence (used interchangeably with polynucleotide or nucleotide sequence) that encodes a chimeric molecule as described herein. This definition includes various sequence polymorphisms, mutations, and/or sequence variants wherein such alterations do not substantially affect the function of the encoded chimeric molecule. The term "gene" may include not only coding sequences but also regulatory regions such as promoters, enhancers, and termination regions. The term further can include all introns and other DNA sequences spliced from the mRNA transcript, along with variants resulting from alternative splice sites. Gene sequences encoding the molecule can be DNA or RNA that directs the expression of the chimeric molecule. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type. Portions of complete gene sequences are referenced throughout the disclosure as is understood by one of ordinary skill in the art.

A gene sequence encoding a tag cassette, hydrophobic portion, spacer region, linker sequence, or any other protein or peptide sequence described herein can be readily prepared by synthetic or recombinant methods from the relevant amino acid sequence. In embodiments, the gene sequence encoding any of these sequences can also have one or more restriction enzyme sites at the 5' and/or 3' ends of the coding sequence in order to provide for easy excision and replacement of the gene sequence encoding the sequence with another gene sequence encoding a different sequence. In embodiments, the gene sequence encoding the sequences can be codon optimized for expression in mammalian cells.

"Encoding" refers to the property of specific sequences of nucleotides in a gene, such as a cDNA, or an mRNA, to serve as templates for synthesis of other macromolecules such as defined sequences of amino acids. Thus, a gene codes for a protein if transcription and translation of mRNA corresponding to that gene produces the protein in a cell or other biological system. A "gene sequence encoding a protein" includes all nucleotide sequences that are degenerate versions of each other and that code for the same amino acid sequence or amino acid sequences of substantially similar form and function.

Polynucleotide gene sequences encoding more than one portion of an expressed chimeric molecule can be operably linked to each other and relevant regulatory sequences. For example, there can be a functional linkage between a regulatory sequence and an exogenous nucleic acid sequence resulting in expression of the latter. For another example, a first nucleic acid sequence can be operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary or helpful, join coding regions, into the same reading frame.

A "vector" is a nucleic acid molecule that is capable of transporting another nucleic acid. Vectors may be, e.g., plasmids, cosmids, viruses, or phage. An "expression vector" is a vector that is capable of directing the expression of a protein encoded by one or more genes carried by the vector when it is present in the appropriate environment.

"Retroviruses" are viruses having an RNA genome. "Gammaretrovirus" refers to a genus of the retroviridae family. Exemplary gammaretroviruses include mouse stem cell virus, murine leukemia virus, feline leukemia virus, feline sarcoma virus, and avian reticuloendotheliosis viruses.

Retroviral vectors (see Miller, et al., 1993, Meth. Enzymol. 217:581-599) can be used. In such embodiments, the gene to be expressed is cloned into the retroviral vector for its delivery into stem cells. In particular embodiments, a retroviral vector contains all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail about retroviral vectors can be found in Boesen, et al., 1994, Biotherapy 6:291-302; Clowes, et al., 1994, J. Clin. Invest. 93:644-651; Kiem, et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114. Adenoviruses, adena-associated viruses (AAV) and alphaviruses can also be used. See Kozarsky and Wilson, 1993, Current Opinion in Genetics and Development 3:499-503, Rosenfeld, et al., 1991, Science 252:431-434; Rosenfeld, et al., 1992, Cell 68:143-155; Mastrangeli, et al., 1993, J. Clin. Invest. 91:225-234; Walsh, et al., 1993, Proc. Soc. Exp. Bioi. Med. 204:289-300; and Lundstrom, 1999, J. Recept. Signal Transduct. Res. 19: 673-686. Other methods of gene delivery include use of mammalian artificial chromosomes (Vos, 1998, Curr. Op. Genet. Dev. 8:351-359); liposomes (Tarahovsky and Ivanitsky, 1998, Biochemistry (Mosc) 63:607-618); ribozymes (Branch and Klotman, 1998, Exp. Nephrol. 6:78-83); and triplex DNA (Chan and Glazer, 1997, J. Mol. Med. 75:267-282).

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

There are a large number of available viral vectors suitable within the current disclosure, including those identified for human gene therapy applications (see Pfeifer and Verma, 2001, Ann. Rev. Genomics Hum. Genet. 2:177). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing chimeric antigen receptor transgenes are described in, e.g., U.S. Pat. No. 8,119,772; Walchli, et al., 2011, PLoS One 6:327930; Zhao, et al., 2005, J. Immunol. 174:4415; Engels, et al., 2003, Hum. Gene Ther. 14:1155; Frecha, et al., 2010, Mol. Ther. 18:1748; and Verhoeyen, et al., 2009, Methods Mol. Biol. 506:97. Retroviral and lentiviral vector constructs and expression systems are also commercially available.

"Nucleic acid molecules", or polynucleotides, may be in the form of RNA or DNA, which includes cDNA, genomic DNA, and synthetic DNA. A nucleic acid molecule may be double stranded or single stranded, and if single stranded, may be the coding strand or non-coding (anti-sense strand). A coding molecule may have a coding sequence identical to a coding sequence known in the art or may have a different coding sequence, which, as the result of the redundancy or degeneracy of the genetic code, or by splicing, can encode the same polypeptide.

Additional embodiments include sequences having 70% sequence identity; 80% sequence identity; 81% sequence identity; 82% sequence identity; 83% sequence identity; 84% sequence identity; 85% sequence identity; 86% sequence identity; 87% sequence identity; 88% sequence identity; 89% sequence identity; 90% sequence identity; 91% sequence identity; 92% sequence identity; 93% sequence identity; 94% sequence identity; 95% sequence identity; 96% sequence identity; 97% sequence identity; 98% sequence identity; or 99% sequence identity to any gene, protein or peptide sequence disclosed herein.

"% sequence identity" refers to a relationship between two or more sequences, as determined by comparing the sequences. In the art, "identity" also means the degree of sequence relatedness between sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., 1990, *J. Mol. Biol.* 215:403-410; DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. "Default values" mean any set of values or parameters which originally load with the software when first initialized.

Without limiting the foregoing, proteins or peptides having a sequence identity to a sequence disclosed herein include variants and D-substituted analogs thereof.

"Variants" of sequences disclosed herein include sequences having one or more additions, deletions, stop positions, or substitutions, as compared to a sequence disclosed herein.

An amino acid substitution can be a conservative or a non-conservative substitution. Variants of protein or peptide sequences disclosed herein can include those having one or more conservative amino acid substitutions. A "conservative substitution" involves a substitution found in one of the following conservative substitutions groups: Group 1: alanine (Ala or A), glycine (Gly or G), Ser, Thr; Group 2: aspartic acid (Asp or D), Glu; Group 3: asparagine (Asn or N), glutamine (Gln or Q); Group 4: Arg, lysine (Lys or K), histidine (His or H); Group 5: Ile, leucine (Leu or L), methionine (Met or M), valine (Val or V); and Group 6: Phe, Tyr, Trp.

Additionally, amino acids can be grouped into conservative substitution groups by similar function, chemical structure, or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cys; acidic: Asp, Glu, Asn, and Gin; small aliphatic, nonpolar or slightly polar residues: Ala, Ser, Thr, Pro, and Gly; polar, negatively charged residues and their amides: Asp, Asn, Glu, and Gin; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

"D-substituted analogs" include proteins or peptides disclosed herein having one more L-amino acids substituted with one or more D-amino acids. The D-amino acid can be the same amino acid type as that found in the reference sequence or can be a different amino acid. Accordingly, D-analogs can also be variants.

Without limiting the foregoing, and for exemplary purposes only:

In particular embodiments, a tag cassette includes a sequence that has at least 80%; 81%; 82%; 83%; 84%; 85%; 86%; 87%; 88%; 89%; 90%; 91%; 92%; 93%; 94%; 95%; 96%; 97%; 98%; or 99% sequence identity to the sequence of Strep tag, His tag, Flag tag, Xpress tag, Avi tag, Calmodulin tag, Polyglutamate tag, HA tag, Myc tag, Nus tag, S tag, X tag, SBP tag, Softag, V5 tag, CBP, GST, MBP, GFP, Thioredoxin tag "Specifically binds" refers to an association or union of a tag cassette to a cognate binding molecule with an affinity or $K_a$ (i.e., an equilibrium association constant of a particular binding interaction with units of 1/M) equal to or greater than $10^5$ $M^{-1}$, while not significantly associating or uniting with any other molecules or components in a sample. Tag cassettes may be classified as "high affinity" or "low affinity". "High affinity" tag cassettes refer to those tag cassettes with a $K_a$ of at least $10^7$ $M^{-1}$, at least 108 $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" tag cassettes refer to those tag cassettes with a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M). In certain embodiments, a tag cassette may have "enhanced affinity," which refers to a selected or engineered tag cassette with stronger binding to a cognate binding molecule than a wild type (or parent) tag cassette. For example, enhanced affinity may be due to a Ka (equilibrium association constant) for the cognate binding molecule that is higher than the wild type tag cassette or due to a $K_d$ (dissociation constant) for the cognate binding molecule that is less than that of the wild type tag cassette, or due to an off-rate ($K_{off}$) for the cognate binding molecule that is less than that of the wild type tag cassette. A variety of assays are known for detecting tag cassettes that specifically bind a particular cognate binding molecule as well as determining tag cassette affinities, such as Western blot, ELISA, and BIACORE® analysis (see also, e.g., Scatchard, et al., 1949, *Ann. N.Y. Acad. Sci.* 51:660; and U.S. Pat. Nos. 5,283,173, 5,468,614, or the equivalent).

In particular embodiments, a tag cassette sequence can have at least 80%; 81%; 82%; 83%; 84%; 85%; 86%; 87%; 88%; 89%; 90%; 91%; 92%; 93%; 94%; 95%; 96%; 97%; 98%; or 99% sequence identity to a tag cassette sequence disclosed herein.

In particular embodiments, an intracellular signaling domain can have at least 80%; 81%; 82%; 83%; 84%; 85%; 86%; 87%; 88%; 89%; 90%; 91%; 92%; 93%; 94%; 95%; 96%; 97%; 98%; or 99% sequence identity to a CD3, having a sequence provided in FIG. 2.

In particular embodiments, a costimulatory signaling domain can have at least 80%; 81%; 82%; 83%; 84%; 85%; 86%; 87%; 88%; 89%; 90%; 91%; 92%; 93%; 94%; 95%; 96%; 97%; 98%; or 99% sequence identity to the intracellular domain of CD28 or to 4-1BB having a sequence provided in FIG. 2. In particular embodiments, a variant of the CD28 intracellular domain includes an amino acid substitution at positions 186-187, wherein LL is substituted with GG.

In particular embodiments, a transmembrane domain can be selected or modified by an amino acid substitution(s) to avoid binding of such domains to the transmembrane domains of the same or different surface membrane proteins to minimize interactions with other members of the receptor complex. In further particular embodiments, synthetic or variant transmembrane domains include predominantly hydrophobic residues such as leucine and valine. Variant transmembrane domains preferably have a hydrophobic score of at least 50 as calculated by Kyte Doolittle. In particular embodiments, a transmembrane domain can have at least 80%; 81%; 82%; 83%; 84%; 85%; 86%; 87%; 88%; 89%; 90%; 91%; 92%; 93%; 94%; 95%; 96%; 97%; 98%; or 99% sequence identity with a hydrophobic portion sequence of FIG. 2.

Proteins and peptides having the same functional capability as those expressly disclosed herein are also included.

When not expressly provided here, sequence information provided by public databases and the knowledge of those of ordinary skill in the art can be used to identify related and relevant protein and peptide sequences and gene sequences encoding such proteins and peptides.

Differentiation. In particular embodiments, modified stem cells are differentiated before or after administration to a subject. Where differentiation of modified stem cells is desired, stem cells can be exposed to one or more activation factors (e.g., growth factors, differentiation factors, and/or survival factors) that promote differentiation into a more committed cell type.

Many activation factors and cell culture conditions that promote differentiation are known in the art (see, e.g., U.S. Pat. No. 7,399,633 at Section 5.2 and Section 5.5). For example, SCF can be used in combination with GM-SCF or IL-7 to differentiate HSPC into myeloid stem/progenitor cells or lymphoid stem/progenitor cells, respectively. In particular embodiments, HSPC can be differentiated into a lymphoid stem/progenitor cell by exposing HSPC to 100 ng/ml of each of SCF and GM-SCF or IL-7. In particular embodiments, a retinoic acid receptor (RAR) agonist, or preferably all trans retinoic acid (ATRA) is used to promote the differentiation of HSPC. Differentiation into natural killer cells, e.g., can be achieved by exposing cultured HSPC to RPMI media supplemented with human serum, IL-2 at 50 U/mL and IL-15 at 500 ng/mL. In additional embodiments, RPMI media can also be supplemented L-glutamine.

Cardiomyocytes have been generated in vitro from a wide range of stem/progenitor cells, including iPSCs (see, e.g., Gai, et al., 2009, *Cell. Biol. Int.* 33:1184-93; Kuzmenkin, et al., 2009, *FASEB J.* 23:4168-80; Pfannkuche, et al., 2009, *Cell Physiol. Biochem.* 24:73-86), ESCs (see, e.g., Beqqali, et al., 2009, *Cell. Mol. Life Sci.* 66:800-13; Steel, et al., 2009, *Curr. Opin. Drug Discov. Dev* 12:133-40), HSPC (see, e.g., Choi, et al., 2008, *Biotechnol. Lett* 30:835-43; Antonitsis, et al., 2008, *Thorac. Cardiovasc. Surg* 56:77-82; Ge, et al., 2009, *Biochem. Biophys. Res. Commun.* 381:317-21; Gwak, et al., 2009, *Cell. Biochem. Funct.* 27:148-54), and cardiomyocyte progenitor cells (see, e.g., Smits, et al., 2009, *Nat. Protoc.* 4:232-43). Mummery, et al., 2012 Jul. 20, *Circ. Res.* 111(3): 344-358 provides a summary of methods to differentiate hESCs and induced pluripotent stem cells into cardiomyocytes. Methods to differentiate stem cells into cardiac cells are also described in, e.g., U.S. Publication No. 2015/0017718.

In particular embodiments, cardiomyocyte progenitors can be generated from hESC embryoid bodies (EBs) treated with Activin A, BMP4 or with 2+Wnt3 and bFGF. These progenitors express Nkx2.5, Tbx5/20, Gata-4, Mef2c and Hand1/2. Their further differentiation to functional cardiomyocytes can be promoted with VEGF and Dkk1 (Vidarsson, et al., 2010, *Stem Cell Rev.* 6:108-20).

Life Technologies offers the PSC Cardiomyocyte Differentiation Kit (supporting components available from Life Technologies include a Cardiomyocyte Maintenance Medium, a Geltrex™ LDEV-Free hESC-qualified Reduced Growth Factor Basement Membrane Matrix and a Human Cardiomyocyte Immunocytochemistry Kit that detects NKX2.5 for early cardiac mesoderm and TNNT2/cTNT for cardiomyocytes along with DAPI nuclear DNA counterstaining).

A protocol for generating insulin producing beta-cells from hESCs involves stepwise lineage restriction generating in sequence: definitive endodermal cells (Activin+Wnt3), primitive foregut endoderm (FGF10+KAAD-cyclopamine), posterior foregut endoderm (RA+FGF10+KAAD-cyclopamine), pancreatic endoderm and endocrine precursors (Extendin-4), and hormone producing cells (IGF1+HGF). Transcription factor profiles include: Sox17, CER, FoxA2, and the cytokine receptor CXCR4 (definitive endodermal cells), Hnf1B, Hnf4A (primitive foregut endoderm), Pdx1, Hnf6, H1xB9 (posterior foregut endoderm), and Nkx6.1, Nkx2.2, Ngn3, Pax4 (pancreatic endoderm and endocrine precursors). See, e.g., D'Amour, et al., 2006, *Nat. Biotechnol.* 24:1392-401; Kroon, et al., 2008, *Nat. Biotechnol.* 26:443-52). Another method to induce stem cells to commit to definitive endoderm, then to pancreatic endoderm, to pancreatic endocrine/exocrine cells and finally to more mature islet cells is described in Jiang, et al., 2007, *Stem Cells* 25(8): p. 1940-53.

Various types of retinal cells can be generated from hESCs (see, e.g., Lamba, et al., 2006, *Proc. Natl. Acad. Sci. USA* 103:12769-74; Reh, et al., 2010, *Methods Mol. Biol.* 636:139-53). EBs can be produced and thereafter treated with IGF1, Noggin (BMP inhibitor) and Dkk1 (Wnt inhibitor). This treatment directs hESCs to adopt a retinal progenitor phenotype, expressing Pax6 and Chx10. Exposing these progenitors to N—(N-(3,5-difluorophenacetyl)-1-alanyl)-S-phenylglycine t-butyl ester (DAPT), a blocker of Notch signaling, promotes neuronal differentiation. A similar protocol can be used to generate retinal cells from human iPSCs (Lamba, et al., 2010, *PLoS One* 5:e8763). The decision to undergo photoreceptor differentiation is under the control of the transcription factor, Blimp1 (Brzezinski, et al., 2010, *Development* 137:619-29).

In particular embodiments, neuronal differentiation can be achieved by replacing a stem cell culture media with a media including basic fibroblast growth factor (bFGF) heparin, and an N2 supplement (e.g., transferrin, insulin, progesterone, putrescine, and selenite). Two days later, differentiating cells can be attached by plating them onto dishes coated with laminin or polyornithine. After an additional 10-11 days in culture, primitive neuroepithelial cells will have formed. The identity of the cells can be confirmed by staining for PAX6 (paired box protein 6, a transcription factor), SOX2 (sex-determining region Y-box 2, another transcription factor), and N-cadherin (a calcium-dependent cell adhesion molecule specific to neural tissue). Neuroepithelial cells can be further differentiated into, e.g., motor neurons (see, e.g., Li, et al. 2005, *Nat. Biotechnol.* 23, 215-221), dopaminergic neurons (see, e.g., Yan, et al. 2005, *Stem Cells* 23, 781-790), and oligodendrocytes (Nistor, et al. 2005, *Glia* 49, 385-396).

Additional information regarding differentiation to motor neurons includes treatment with RA (Pax6 expressing primitive neuroepithelial cells), RA+Shh (Pax6/Sox1 expressing neuroepithelial cells), which gradually start to express the motor neuron progenitor marker Olig2. Reducing RA+Shh concentration promotes the emergence of motor neurons expressing HB9 and Islet1. The addition of brain-derived neurotrophic factor (BDNF), glial-derived neurotrophic factor (GDNF), insulin-like growth factor-1 (IGF1), and cAMP promotes process outgrowth (see, e.g., Hu, et al., 2009, *Nat. Protoc.* 4:1614-22; Hu, et al., 2010, *Proc. Natl. Acad. Sci. USA;* 107:4335-40).

Additional information regarding differentiation to dopaminergic neurons includes overexpression of the transcription factor Nurr1 followed by exposure to Shh, FGF-8 and ascorbic acid (see, e.g., Lee, et al., 2000 June, *Nat. Biotechnol.* 18(6):675-9; Kriks and Studer, 2009, *Adv. Exp. Med. Biol.* 651:101-11; Lindvall and Kokaia, 2009 May, *Trends Pharmacol. Sci.* 30(5):260-7.). The combination of stromal cell-derived factor 1 (SDF-1/CXCL12), pleiotrophin (PTN), insulin-like growth factor 2 (IGF2), and ephrin B1 (EFNB1) can induce hESCs to differentiate to TH-positive neurons in vitro, expressing midbrain specific markers, including Engrailed 1, Nurr1, Pitx3, and dopamine transporter (DAT). These neurons are capable of generating action potentials and forming functional synaptic connections (Vazin, et al., 2009, *PLoS One* 4:e6606).

U.S. Publication No. 2014/0335059 describes differentiation of human oral mucosa stem cells from the lamina propria (hOMSC) into dopaminergic neural cells by (a) incubating hOMSC for at least 48-96 hours, in a medium comprising at least one agent selected from: N-2 supplement, bFGF and EGF; and (b) incubating the hOMSC of (a) in a differentiation medium for at least 11 days in a medium including a plurality of agents selected from: B27, IBMX, dbcAMP, ascorbic acid, BNDF, Sonic Hedgehog, Wnt-1, FGF-8, and bFGF. Particular embodiments utilize a differentiating incubation medium including 0.1-5% B27, 85-750 ng/mL Sonic Hedgehog, 30-300 ng/mL Wnt-1, 30-300 ng/mL FGF-8, 15-150 ng/mL BDNF, 15-150 ng/mL bFGF, and 65-600 ng/mL of ascorbic acid. Additional particular embodiments utilize 0.1-5% B27, 100-400 ng/mL Sonic Hedgehog, 50-150 ng/mL Wnt-1, 50-150 ng/mL FGF-8, 25-100 ng/mL BDNF, 25-100 ng/mL bFGF, and 100-400 ng/mL of ascorbic acid.

A protocol to produce mature myelinating oligodendrocytes from hESCs is described in, e.g., Hu, et al., 2009, *Nat. Protoc.* 4:1614-22. hESCs are first directed toward neuroectoderm differentiation in the absence of growth factors for 2 weeks. These cells express neuroectoderm transcription factors, including Pax6 and Sox1. Next hESCs are exposed to the caudalizing factor retinoic acid (RA) and the ventralizing morphogen Shh for 10 days to begin expression of Olig2. To prevent the differentiation to motor neurons and promote the generation of oligodendrocyte precursor cells (OPC)s, cells are cultured with FGF2 for 10 days. By day 35, the Olig2 progenitors co-express NkxX2.2 and no longer give rise to motor neurons. The co-expression of Olig2 and Nkx2.2 reflects a stage prior to human OPCs (pre-OPCs). These pre-OPCs are finally cultured in a glia medium including triiodothyronine (T3), neurotrophin 3 (NT3), PDGF, cAMP, IGF-1 and biotin, which individually or synergistically can promote the survival and proliferation of the hESC derived OPCs, for another 8 weeks to generate OPCs. These OPCs are bipolar or multipolar, express Olig2, Nkx2.2, Sox10 and PDGFRα, become motile and are able to differentiate to competent oligodendrocytes. WO2007/066338 also describes differentiation protocols for the generation of oligodendrocyte-like cells.

A protocol to produce glutamatergic neurons includes use of ESCs to produce cell aggregates which are then treated for 8 days with RA. This results in Pax6 expressing radial glial cells, which after additional culturing in N2 followed by "complete" medium results in 95% glutamate neurons (Bibel, et al., 2007, *Nat. Protoc.* 2:1034-43).

A protocol to produce GABAergic neurons includes exposing EBs for 3 days to all-trans-RA. After subsequent culture in serum-free neuronal induction medium including Neurobasal medium supplemented with B27, bFGF and EGF, 95% GABA neurons develop (see, e.g., Chatzi, et al., 2009, *Exp. Neurol.* 217:407-16).

U.S. Publication No. 2013/0330306 describes compositions and methods to induce differentiation and proliferation of neural precursor cells or neural stem cells into neural cells using umbilical cord blood-derived mesenchymal stem cells; U.S. Publication No. 2007/0179092 describes use of pituitary adenylate cyclase activating polypeptide (PACAP) to enhance neural stem cell proliferation, differentiation and survival; U.S. Publication No. 2012/0329714 describes use of prolactin to increase neural stem cell numbers; while U.S. Publication No. 201210308530 describes a culture surface with amino groups that promotes neuronal differentiation into neurons, astrocytes and oligodendrocytes. U.S. Publication No. 2006/211109 describes improved methods for efficiently producing neuroprogenitor cells and differentiated neural cells such as dopaminergic neurons and serotonergic neurons from pluripotent stem cells, e.g., hESCs.

Thus, the fate of neural stem cells can be controlled by a variety of extracellular factors. Commonly used factors include amphiregulin; BMP-2 (U.S. Pat. Nos. 5,948,428 and 6,001,654); brain derived growth factor (BDNF; Shetty and Turner, 1998, *J. Neurobiol.* 35:395-425); neurotrophins (e.g., Neurotrophin-3 (NT-3) and Neurotrophin-4 (NT-4); Caldwell, et al., 2001, *Nat. Biotechnol.* 1; 19:475-9); ciliary neurotrophic factor (CNTF); cyclic adenosine monophosphate; epidermal growth factor (EGF); dexamethasone (glucocorticoid hormone); fibroblast growth factor (bFGF; U.S. Pat. No. 5,766,948; FGF-1, FGF-2); forskolin; GDNF family receptor ligands; growth hormone; interleukins; insulin-like growth factors; isobutyl 3-methylxanthine; leukemia inhibitory growth factor (LIF; U.S. Pat. No. 6,103,530); Notch antagonists (U.S. Pat. No. 6,149,902); platelet derived growth factor (PDGF; U.S. Pat. No. 5,753,506); potassium; retinoic acid (U.S. Pat. No. 6,395,546); somatostatin; tetanus toxin; and transforming growth factor-α and TGF-β (U.S. Pat. Nos. 5,851,832 and 5,753,506).

In particular embodiments, preferred proliferation-inducing neural growth factors include BNDF, EGF and FGF-1 or FGF-2. Growth factors can be usually added to the culture medium at concentrations ranging between about 1 fg/ml of a pharmaceutically acceptable composition (including, e.g., CNS compatible carriers, excipients and/or buffers) to 1 mg/ml.

Growth factor expanded stem cells can also differentiate into neurons and glia after mitogen withdrawal from a culture medium.

Additionally, WO 2004/046348 describes differentiation protocols for the generation of neural-like cells from bone marrow-derived stem cells. WO 2006/134602 describes differentiation protocols for the generation of neurotrophic factor secreting cells. Commercial kits are also available from Life Technologies and include PSC Neural Induction Medium, Geltrex™ LDEV-Free hESC-qualified Reduced Growth Factor Basement Membrane Matrix, and a Human Neural Stem Cell Immunocytochemistry kit. Stem cells differentiated into neural cells using the Life Technology kits can be further terminally differentiated into neurons, astrocytes and oligodendrocytes using Life Technologies' B-27® supplements, with N-2 supplement and NEUROBASAL® Medium.

Additional methods to assist with stem cell differentiation protocols include, e.g., culture vessels with a portion comprising an oxygen permeable substrate at least partially coated with a synthetic matrix having an average thickness of less than 100 nm. See, e.g., U.S. Publication No. 2014/0370598.

U.S. Publication No. 2013/0251690 describes methods to support stem cell differentiation in elderly populations.

A number of different differentiation methods have been described. Additional methods that can be used within the teaching of the current disclosure can be found in the art by those with ordinary skill. Furthermore, and as indicated, differentiation of stem cells can be confirmed by measuring cellular markers expressed by the desired differentiated cell.

The foregoing discussion describes in vitro or ex vivo differentiation methods. Modified stem cells disclosed herein can also differentiate in vivo following administration. In particular embodiments, components that support activation (e.g., expansion, differentiation and/or survival) of modified stem cells in vitro are administered in combination with modified stem cells to direct differentiation and survival following administration in vivo. In general, activation factors include any proteins, peptides or other molecules having a growth, proliferative, differentiative, or trophic effect on stem cells and/or stem cell progeny. Activation factors which may be used for inducing proliferation include any trophic factor that allows stem cells and precursor cells to proliferate, including any molecule which binds to a receptor on the surface of the cell to exert a trophic, or growth-inducing effect on the cell.

To support differentiation and/or survival of modified stem cells in vivo, stem-cell activation factors may be delivered or formulated for timed-release. Several examples of time-release formulations that may be used are described in, e.g., WO 2002/45695; U.S. Pat. Nos. 4,601,894; 4,687,757; 4,680,323; 4,994,276; and 3,538,214.

For preparation of stem cell grafts including activation factors stem cells can be substantially evenly distributed throughout a transplantation matrix with these factors. Transplantation matrices suitable for use in the body include e.g., the tissue adhesive compositions described in Petersen, et al., 2004, *Gastrointestinal Endoscopy* 60(3):327-333. A mixture of fibrin and thrombin can be particularly well-suited for stem cell delivery. Such mixtures are commercially available as fibrin glue products; e.g., a 50:50 mixture product from Sigma Chemicals. Stem cells can be evenly suspended in the tissue adhesive with activation factors, in particular embodiments, just prior to implantation.

Stem-cell activation factors may be loaded into mesoporous particles, e.g., mesoporous silica materials. The mesoporous particles can be a solvent extracted and/or a calcined material (see, e.g., Atluri, et al., 2008, *Chemistry of Materials* 20(12), 3857-3866). Materials may be mixed with the desired amount of stem-cell activation factors in a solvent that will dissolve or partially dissolve the aforementioned factors. The mixture may be stirred, centrifuged, spray dried, or filtered after periods between 0.5 hours and 2 days at temperatures between 0-80° C. If the sample is stirred, the recovered solid typically contains between 20-49 wt % of factors within the pores of the mesoporous silica particle. Higher amounts can be obtained if the loading process is repeated several times. For additional detail regarding these delivery particles and methods, see U.S. Publication No. 2013/0315962.

U.S. Publication No. 2014/0308256 describes co-administration of stem-cell activation factors with stem cells in neural applications. For example, this disclosure teaches that stem cell survival and axonal growth may be enhanced by supplying a neural stem cell graft with an activation factor source. The source may be provided by co-administration or separate delivery of an activation factor, such as NT-3, BDNF, CTNF, NGF, NT-4/5, FGF, EGF and GDNF (including GDNF family neurotrophins such as neurturin). Concentrations between 1 to 100 ng/ml are usually sufficient and may be conveniently added to the cell graft composition, co-administered into the graft and/or administered within diffusion distance of the graft. When the neural stem cells are implanted at a target lesion site, suspended evenly in a transplantation matrix in the presence of at least one activation factor, the grafted neural stem cells differentiate, undergo axonal myelination, and establish synaptic contacts with host circuitry. Reciprocally, host axons penetrate grafts in the lesion site and establish putative synaptic contacts.

Stem-cell activation factors may also be provided by expression from a co-administered recombinant expression vector or from donor cells. Coding polynucleotides, precursors and promoters for a number of activation factors are known. For example, GenBank M61176 sets forth the coding sequence (mRNA) for BDNF; BDNF precursor is set forth at BF439589; and a BDNF specific promoter is set forth at E05933. A similar range of coding sequences for other activation factors are also available through GenBank and other publicly accessible nucleotide sequence databases.

Suitable recombinant expression vectors are described elsewhere herein. Preparation of stem-cell activation factor-expressing donor cells (e.g., fibroblasts) may be as described in U.S. Pat. No. 6,451,306. Such cells may be co-grafted with stem cells, but need not be included within a stem cell/transplantation matrix composition.

An additional method to control stem cell differentiation after transplantation is by controlled expression of transcription factors in the transplanted cells using drug-inducible regulation systems as described, e.g., in WO 2008/002250. For example, using the tetracycline gene regulation system to induce expression of the key transcription factor Runx1 in Sox10 expressing neural crest stem cells, specific differentiation of nociceptor neurons was observed in vivo after transplantation. See, e.g., Aldskogius, et al., 2009, *Stem Cells* 27:1592-603.

Another method to promote stem cell differentiation and survival after administration is through use of osmotic minipumps that provide stem-cell activation factors for improved survival, differentiation and function of transplanted cells.

In particular embodiments, co-transplantation of neural crest stem cells with pancreatic islets creates beneficial effects for both islets and stem cells with improved insulin secretion, increased proliferation of beta-cells and advanced differentiation of neural crest stem cells in the vicinity of islets. Olerud, et al., 2010, *Diabetologia* 53:396.

Compositions and Formulations. Modified cells can be prepared as compositions and/or formulations for administration to a subject. A composition refers to a cell or modified cell prepared with a pharmaceutically acceptable carrier for administration to a subject. A formulation refers to at least two cell types within a pharmaceutically acceptable carrier (hereafter carrier) for administration to a subject.

At various points during preparation of a composition or formulation, it can be necessary or beneficial to cryopreserve a cell. The terms "frozen/freezing" and "cryopreserved/cryopreserving" can be used interchangeably. Freezing includes freeze drying.

As is understood by one of ordinary skill in the art, the freezing of cells can be destructive (see Mazur, P., 1977, *Cryobiology* 14:251-272) but there are numerous procedures available to prevent such damage. For example, damage can be avoided by (a) use of a cryoprotective agent, (b) control of the freezing rate, and/or (c) storage at a temperature sufficiently low to minimize degradative reactions. Exemplary cryoprotective agents include dimethyl sulfoxide (DMSO) (Lovelock and Bishop, 1959, *Nature* 183:1394-1395; Ashwood-Smith, 1961, *Nature* 190:1204-1205), glycerol, polyvinylpyrrolidine (Rinfret, 1960, *Ann. N.Y. Acad. Sci.* 85:576), polyethylene glycol (Sloviter and Ravdin, 1962, *Nature* 196:548), albumin, dextran, sucrose, ethylene glycol, i-erythritol, D-ribitol, D-mannitol (Rowe, et al., 1962, *Fed. Proc.* 21:157), D-sorbitol, i-inositol, D-lactose, choline chloride (Bender, et al., 1960, *J. Appl. Physiol.* 15:520), amino acids (Phan The Tran and Bender, 1960, *Exp. Cell Res.* 20:651), methanol, acetamide, glycerol monoacetate (Lovelock, 1954, *Biochem. J.* 56:265), and inorganic salts (Phan The Tran and Bender, 1960, *Proc. Soc. Exp. Biol. Med.* 104:388; Phan The Tran and Bender, 1961, in Radiobiology, Proceedings of the Third Australian Conference on Radiobiology, Ilbery ed., Butterworth, London, p. 59). In particular embodiments, DMSO can be used. Addition of plasma (e.g., to a concentration of 20-25%) can augment the protective effects of DMSO. After addition of DMSO, cells can be kept at 0° C. until freezing, because DMSO concentrations of 1% can be toxic at temperatures above 4° C.

In the cryopreservation of cells, slow controlled cooling rates can be critical and different cryoprotective agents (Rapatz, et al., 1968, *Cryobiology* 5(1): 18-25) and different cell types have different optimal cooling rates (see e.g., Rowe and Rinfret, 1962, *Blood* 20:636; Rowe, 1966, *Cryobiology* 3(1):12-18; Lewis, et al., 1967, *Transfusion* 7(1): 17-32; and Mazur, 1970, *Science* 168:939-949 for effects of cooling velocity on survival of stem cells and on their transplantation potential). The heat of fusion phase where water turns to ice should be minimal. The cooling procedure can be carried out by use of, e.g., a programmable freezing device or a methanol bath procedure. Programmable freezing apparatuses allow determination of optimal cooling rates and facilitate standard reproducible cooling.

In particular embodiments, DMSO-treated cells can be pre-cooled on ice and transferred to a tray containing chilled methanol which is placed, in turn, in a mechanical refrigerator (e.g., Harris or Revco) at −80° C. Thermocouple measurements of the methanol bath and the samples indicate a cooling rate of 1 to 3° C./minute can be preferred. After at least two hours, the specimens can have reached a temperature of −80° C. and can be placed directly into liquid nitrogen (−196° C.).

After thorough freezing, the cells can be rapidly transferred to a long-term cryogenic storage vessel. In a preferred embodiment, samples can be cryogenically stored in liquid nitrogen (−196° C.) or vapor (−1° C.). Such storage is facilitated by the availability of highly efficient liquid nitrogen refrigerators.

Further considerations and procedures for the manipulation, cryopreservation, and long-term storage of cells, can be found in the following exemplary references: U.S. Pat. Nos. 4,199,022; 3,753,357; and 4,559,298; Gorin, 1986, Clinics In Haematology 15(1):19-48; Bone-Marrow Conservation, Culture and Transplantation, Proceedings of a Panel, Moscow, Jul. 22-26, 1968, International Atomic Energy Agency, Vienna, pp. 107-186; Livesey and Linner, 1987, *Nature* 327:255; Linner, et al., 1986, *J. Histochem. Cytochem.* 34(9):1123-1135; Simione, 1992, *J. Parenter. Sci. Technol.* 46(6):226-32).

Following cryopreservation, frozen cells can be thawed for use in accordance with methods known to those of ordinary skill in the art. Frozen cells are preferably thawed quickly and chilled immediately upon thawing. In particular embodiments, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed on ice.

In particular embodiments, methods can be used to prevent cellular clumping during thawing. Exemplary methods include: the addition before and/or after freezing of DNase (Spitzer, et al., 1980, *Cancer* 45:3075-3085), low molecular weight dextran and citrate, hydroxyethyl starch (Stiff, et al., 1983, *Cryobiology* 20:17-24), etc.

As is understood by one of ordinary skill in the art, if a cryoprotective agent that is toxic to humans is used, it should be removed prior to therapeutic use. DMSO has no serious toxicity.

Exemplary carriers and modes of administration of cells are described at pages 14-15 of U.S. Publication No. 2010/0183564. Additional pharmaceutical carriers are described in Remington: The Science and Practice of Pharmacy, 21st Edition, David B. Troy, ed., Lippicott Williams & Wilkins (2005).

In particular embodiments, cells can be harvested from a culture medium, and washed and concentrated into a carrier in a therapeutically-effective amount. Exemplary carriers include saline, buffered saline, physiological saline, water, Hanks' solution, Ringer's solution, Nonnosol-R (Abbott Labs), PLASMA-LYTE A® (Baxter Laboratories, Inc., Morton Grove, Ill.), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% HAS or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, compositions or formulations can include a local anesthetic such as lidocaine to ease pain at a site of injection.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Therapeutically effective amounts of cells within compositions or formulations can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$.

In compositions and formulations disclosed herein, cells are generally in a volume of a liter or less, 500 mls or less, 250 mls or less or 100 mls or less. Hence the density of administered cells is typically greater than $10^4$ cells/ml, $10^7$ cells/ml or $10^8$ cells/ml.

As indicated, compositions include one cell type (e.g., modified stem cell or modified differentiated cell). Formulations can include stem cells, modified-stem cells and/or modified differentiated cells in combination. In particular embodiments, stem cells and modified-stem cells are combined. In other embodiments, modified-stem cells and modified differentiated cells are combined. In additional embodiments, stem cells and modified differentiated cells are combined. Similarly, all other aspects of an expressed chimeric molecule (e.g., tag cassettes, transmembrane domains, spacer regions, effector domains, etc.) can be the same or different in various combinations between modified stem cells and modified differentiated cells within a formulation. Additionally, modified stem cells expressing different chimeric molecules or components thereof can be included together within a formulation and modified differentiated cells expressing different chimeric molecules or components thereof can be included together within a formulation. In particular embodiments, a formulation can include at least two modified stem cells expressing different chimeric molecules and at least two modified differentiated cells expressing different chimeric molecules.

Stem cells, modified stem cells and modified differentiated cell types can be provided in different ratios e.g., a 1:1:1 ratio, 2:1:1 ratio, 1:2:1 ratio, 1:1:2 ratio, 5:1:1 ratio, 1:5:1 ratio, 1:1:5 ratio, 10:1:1 ratio, 1:10:1 ratio, 1:1:10 ratio, 2:2:1 ratio, 1:2:2 ratio, 2:1:2 ratio, 5:5:1 ratio, 1:5:5 ratio, 5:1:5 ratio, 10:10:1 ratio, 1:10:10 ratio, 10:1:10 ratio, etc. These ratios can also apply to numbers of cells expressing the same or different chimeric molecule components. If only two of the cell types are combined or only 2 combinations of expressed chimeric molecule components are included within a formulation, the ratio can include any 2 number combination that can be created from the 3 number combinations provided above. In embodiments, the combined cell populations are tested for efficacy and/or cell proliferation in vitro, in vivo and/or ex vivo, and the ratio of cells that provides for efficacy and/or proliferation of cells is selected.

The compositions and formulations disclosed herein can be prepared for administration by, e.g., injection, infusion, perfusion, or lavage. The compositions and formulations can further be formulated for bone marrow, intravenous, intradermal, intraarterial, intranodal, intralymphatic, intraperitoneal, intralesional, intraprostatic, intravaginal, intrarectal, topical, intrathecal, intratumoral, intramuscular, intravesicular, and/or subcutaneous injection.

Kits. Kits can include one or more containers including one or more of the cells, compositions or formulations described herein. In particular embodiments, the kits can include one or more containers containing one or more cells, compositions or formulations and/or compositions to be used in combination with other cells, compositions or formulations. Associated with such container(s) can be a notice in the form prescribed by a governmental agency regulating the manufacture, use, or sale of pharmaceuticals or biological products, which notice reflects approval by the agency of manufacture, use, or sale for human administration. The notice may state that the provided cells, compositions or formulations can be administered to a subject without immunological matching. The kits can include further instructions for using the kit, e.g., instructions regarding preparation of cells, compositions and/or formulations for administration; proper disposal of related waste; and the like. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website. In particular embodiments, kits can also include some or all of the necessary medical supplies needed to use the kit effectively, such as syringes, ampules, tubing, facemask, a needleless fluid transfer device, an injection cap, sponges, sterile adhesive strips, Chloraprep, gloves, and the like. Variations in contents of any of the kits described herein can be made.

Methods of Use. Methods disclosed herein include treating subjects (humans, veterinary animals (dogs, cats, reptiles, birds, etc.), livestock (horses, cattle, goats, pigs, chickens, etc.), and research animals (monkeys, rats, mice, fish, etc.) with cells disclosed herein. Treating subjects includes delivering therapeutically effective amounts. Therapeutically effective amounts include those that provide effective amounts, prophylactic treatments, and/or therapeutic treatments.

An "effective amount" is the number of cells necessary to result in a desired physiological change in a subject. Effective amounts are often administered for research purposes.

A "prophylactic treatment" includes a treatment administered to a subject who does not display signs or symptoms of a condition to be treated or displays only early signs or symptoms of the condition to be treated such that treatment is administered for the purpose of diminishing, preventing, or decreasing the risk of developing the condition. Thus, a prophylactic treatment functions as a preventative treatment against a condition.

A "therapeutic treatment" includes a treatment administered to a subject who displays symptoms or signs of a condition and is administered to the subject for the purpose of reducing the severity or progression of the condition.

The actual dose amount administered to a particular subject can be determined by a physician, veterinarian, or researcher taking into account parameters such as physical and physiological factors including body weight; type of condition; severity of condition; upcoming relevant events, when known; previous or concurrent therapeutic interventions; idiopathy of the subject; and route of administration, for example. In addition, in vivo and/or ex vivo assays can optionally be employed to help identify optimal dosage ranges.

Therapeutically effective amounts to administer can include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$.

As indicated, the compositions and formulations disclosed herein can be administered by, e.g., injection, infusion, perfusion, or lavage and can more particularly include administration through one or more bone marrow, intravenous, intradermal, intraarterial, intranodal, intralymphatic, intraperitoneal, intralesional, intraprostatic, intravaginal, intrarectal, topical, intrathecal, intratumoral, intramuscular, intravesicular, and/or subcutaneous infusions and/or bolus injections.

As is understood by one of ordinary skill in the art, modified stem cells and differentiated cells can be used in a variety of therapeutic applications. The following provides non-limiting examples of such uses.

U.S. Publication NO. 2005/0031600 describes use of mesenchymal stem cell transplantation to improve cardiac function of damaged or scarred myocardial tissue. Intravascular delivery or cardiac transplants of multipotent or pre-differentiated cardiogenic cells from mesenchymal stem cell sources have been shown to promote cardiac structural repair and functional restoration in animal models of myocardial injury (Fukushima, et al., 2008, *PLoS One* 3:e3071; Hendry, et al., 2008, *J. Thorac. Cardiovasc. Surg.* 136:1028-37; Matsuura, et al., 2009, *J. Clin. Invest.* 119:2204-17; Jin, et al., 2009, *Eur. J. Heart Fail.* 11:147-53; Okura, et al., 2010, *Tissue Eng. Part C Methods* 16:417-25). U.S. Publication Nos. 2012/0034595; 2010/0292747; 2010/0286736; and 2008/0213230 also describe use of stem cells to treat cardiac conditions and a number of clinical trials have been initiated. See, e.g., Segers, et al., 2008, *Nature* 451:937-42; Joggerst and Hatzopoulos, 2009 Jul. 8, *Exp. Rev. Molec. Med.* Epub. 11:e20; Piepoli, 2009, *J. Cardiovasc. Med.* 10:624-34).

Stem cells also find use in the treatment of neurodegenerative diseases. These include diseases which progressively degenerate neurons or neuronal function. Examples of neurodegenerative diseases include all forms of senile dementia including chronic disorders such as Alzheimer's disease and Huntington's Chorea, Parkinson's disease, amyotrophic lateral sclerosis, and acute disorders such as stroke, schizophrenia, epilepsy, and injury of the brain, peripheral nerves or spinal cord. U.S. Publication No. 2011/0201113 describes use of stem cells in the treatment of neurodegenerative disorders, neurotrauma, Alzheimer's disease, Parkinson's disease, and the like.

The U.S. Food and Drug Administration (FDA) approved study of autologous, mesenchymal stem cell-derived neural progenitor cells (MSC-NPs) as an Investigational New Drug (IND) for an open label, phase I clinical trial in the treatment of multiple sclerosis. The FDA also approved study of neural stem cells developed by Neuralstem, Inc. as an Investigational New Drug for injection along multiple sites of the spinal cord. Ryan Benton, a 28 year-old Duchenne's muscular dystrophy patient from Wichita, Kans., received an umbilical cord tissue-derived mesenchymal stem cell treatment following the FDA's approval of his doctor's application for a single patient, investigational new drug (IND) for compassionate use. An ocular stem cell therapy to treat an eye condition leading to blindness was recently approved in Europe.

U.S. Publication No. 2004/0185043 describes use of stem cells to treat autoimmune disease. U.S. Publication No. 2014/0363407 describes use of neural stem cells to treat diabetes and obesity. U.S. Publication No. 2013/0095081 describes use of stem cells to treat insulin-related disorders while U.S. Publication Nos. 2007/0077201 and 2007/0031384 describe regeneration of pancreatic islets.

U.S. Publication No. 2013/0095077 describes use of stem cells to treat degenerative diseases such as muscle-degenerative diseases. U.S. Publication No. 2010/0135965 describes use of stem cell to treat diseases caused by cartilage damage. U.S. Publication No. 2007/0207130 describes use of stem cells to treat symptoms of avian flu and other diseases. U.S. Publication No. 2012/0107282 describes use of neural stem cells to treat cancer.

Functional integration of administered cells into a subject's tissue can be assessed by examining the effectiveness of administered cells on restoring various functions. For example, cardiac outputs and exercise physiology stress tests can be used. For neural applications, motor, sensory, autonomic, endocrine, and cognitive function tests can be performed. Motor tests can include those which quantitate use of the limbs for motor tasks such as locomotion and food retrieval, accuracy of limb placement in walking over a grid, and walking on a treadmill. Sensory tasks can include measures of thermal sensitivity and allodynia, including von Frey hair analysis as well as visual, auditory and olfactory tests. Autonomic outcomes can be measured using assessment of heart rate, blood pressure and reflex responses to stimuli. Cognitive tests can include various tests of ability to perform everyday tasks, as well as various memory tests, including maze performance.

As indicated, the modified cells disclosed herein also have important uses in manufacturing and/or as research tools. With regard to uses as research tools, the modified cells can be administered and tracked. In particular embodiments, the modified cells can be tracked following in vivo activation or differentiation. The effect of depleting or eliminating the cells at various time points following administration can also be assessed. These examples are just a small subset of potential research uses of the modified cells disclosed herein.

As is understood by one of ordinary skill in the art, animal models of different conditions are well known and can be used to assess effectiveness of particular treatment paradigms, as necessary or beneficial.

The Examples and Exemplary Embodiments below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

1. A stem cell or differentiated cell genetically modified to express a chimeric molecule including an extracellular component including a tag cassette that specifically binds an exogenous cognate binding molecule (ExoCBM).

2. A stem cell or differentiated cell of embodiment 1 wherein the extracellular component has one, two, three, four or five tag cassettes.

3. A stem cell or differentiated cell of embodiment 1 or 2 wherein at least one tag cassette is or includes a Strep tag, His tag, Flag tag, Xpress tag, Avi tag, Calmodulin tag, Polyglutamate tag, HA tag, Myc tag, Nus tag, S tag, X tag, SBP tag, Softag, V5 tag, CBP, GST, MBP, GFP, Thioredoxin tag, or any combination thereof.

4. A stem cell or differentiated cell of any of embodiments 1-3 wherein at least one tag cassette is or includes a Strep tag including the amino acid sequence SEQ ID NO:1 or SEQ ID NO:17.

5. A stem cell or differentiated cell any of embodiments 1-5 wherein the extracellular component further includes a tag sequence that specifically binds an endogenous cognate binding molecule (EndoCBM).

6. A stem cell or differentiated cell of embodiment 5 wherein the EndoCBM is an activation factor.

7. A stem cell or differentiated cell of any of embodiments 6 wherein the activation factor is selected from Activin A, Amphiregulin, BDNF, bFGF, BMP2, BMP4, CNTF, Dkk1, EGF, IGF1, LIF, Neurotrophin-3, Neurotrophin-4, Noggin, PDGF, retinoic acid, TGF-α, TGF-β, and VEGF.

8. A stem cell or differentiated cell of any of embodiments 1-7 wherein the stem cell or differentiated cell is also genetically modified to express a hydrophobic portion.

9. A stem cell or differentiated cell of any of embodiment 8 wherein the hydrophobic portion includes a human transmembrane domain.

10. A stem cell or differentiated cell of embodiment 9 wherein the transmembrane domain is a CD28 transmembrane domain, a CD4 transmembrane domain, a CD8 transmembrane domain or a CD27 transmembrane domain.

11. A stem cell or differentiated cell of embodiments 1-10 wherein the chimeric molecule includes a linker sequence.

12. A stem cell or differentiated cell of embodiment 11 wherein the linker sequence includes a (GlyxSery)n sequence, wherein n is an integer from 1 to 10, and x and y are independently an integer from 0 to 10 provided that x and y are not both 0.

13. A stem cell or differentiated cell of embodiment 11 wherein the linker sequence is a portion of an Fc domain of a human antibody selected from CH2CH3 or a CH3.

14. A stem cell or differentiated cell of embodiment 11 wherein the linker sequence has an amino acid sequence of Gly-Gly-Gly-Gly-Ser (SEQ ID NO:25), (Gly-Gly-Gly-Gly-Ser)$_2$ (SEQ ID NO:5), or (Gly-Gly-Gly-Ser)$_2$-Gly-Gly-Ser (SEQ ID NO:7).

15. A stem cell or differentiated cell of any of embodiments 1-14 wherein the chimeric molecule includes a linker sequence adjacent to one or more tag cassettes, wherein the linker sequence and adjacent tag cassette collectively have an amino acid sequence of (Gly-Gly-Gly-Gly-Ser)$_2$-Trp-Ser-His-Pro-Gln-Phe-Glu-Lys (SEQ ID NO:19), Trp-Ser-His-Pro-Gln-Phe-Glu-Lys-(Gly-Gly-Gly-Gly-Ser)$_2$ (SEQ ID NO:20), (Gly-Gly-Gly-Gly-Ser)$_2$-Trp-Ser-His-Pro-Gln-Phe-Glu-Lys-(Gly-Gly-Gly-Gly-Ser)$_2$-Gly-Gly-Ser-Trp-Ser-His-Pro-Gln-Phe-Glu-Lys (SEQ ID NO:21), Trp-Ser-His-Pro-Gln-Phe-Glu-Lys-(Gly-Gly-Gly-Gly-Ser)$_2$-Gly-Gly-Ser-Trp-Ser-His-Pro-G n-Phe-Glu-Lys-(Gly-Gly-Gly-Gly-Ser)$_2$ (SEQ ID NO:22), (Gly-Gly-Gly-Gly-Ser)$_2$-Trp-Ser-His-Pro-Gln-Phe-Glu-Lys-(Gly-Gly-Gly-Gly-Ser)$_2$-Gly-Gly-Ser-Trp-Ser-His-Pro-Gln-Phe-Glu-Lys-(Gly-Gly-Gly-Gly-Ser)$_2$-Trp-Ser-His-Pro-Gln-Phe-Glu-Lys (SEQ ID NO:23), or Trp-Ser-His-Pro-Gln-Phe-Glu-Lys-(Gly-Gly-Gly-Gly-Ser)$_2$-Trp-Ser-His-Pro-Gln-Phe-Glu-Lys-(Gly-Gly-Gly-Gly-Ser)$_2$-Gly-Gly-Ser-Trp-Ser-His-Pro-Gln-Phe-Glu-Lys-(Gly-Gly-Gly-Gly-Ser)$_2$ (SEQ ID NO:24).

16. A stem cell or differentiated cell of any of embodiments 1-15 wherein the extracellular component includes a spacer region.

17. A stem cell or differentiated cell of embodiment 16 wherein the spacer region is of a length selected from 12 amino acids or less, 119 amino acids or less, or 229 amino acids or less.

18. A stem cell or differentiated cell of embodiment 16 wherein the spacer region is SEQ ID NO:31, or SEQ ID NO:30.

19. A stem cell or differentiated cell of embodiment 16 wherein the spacer region includes a hinge.

20. A stem cell or differentiated cell of embodiment 16 wherein the spacer region includes a portion of a hinge region of a human antibody.

21. A stem cell or differentiated cell of embodiment 16 wherein the spacer region includes a Fc domain and a human IgG4 heavy chain hinge.

22. A stem cell or differentiated cell of embodiment 16 wherein the spacer region includes a hinge region and at least one other portion of an Fc domain of a human antibody selected from CH1, CH2, CH3, or combinations thereof.

23. A stem cell or differentiated cell of embodiment 8 wherein the hydrophobic portion links the extracellular component to an intracellular component.

24. A stem cell or differentiated cell of embodiment 23 wherein the intracellular component includes an effector domain.

25. A stem cell or differentiated cell of embodiment 23 wherein the effector domain includes one or more signaling, stimulatory or co-stimulatory domains selected from: 4-1BB, B7-H3, CARD11, CD2, CD3γ, CD3δ, CD3ε, CD3ζ, CD7, CD25, CD27, CD28, CD30, CD40, CD79A, CD79B, DAP10, FcRα, FcRβ, FcRγ, Fyn, HVEM, ICOS, LAG3, LAT, Lck, LFA-1, LIGHT, LRP, NKG2C, NKG2D, NOTCH1, NOTCH2, NOTCH3, NOTCH4, pTα, PTCH2, OX40, ROR2, Ryk, SLAMF1, Slp76, TCRα, TCRβ, TRIM, Wnt, and Zap70.

26. A stem cell or differentiated cell of embodiment 23 wherein the intracellular component includes an effector domain including an intracellular signaling domain including (i) all or a portion of the signaling domain of CD3ζ, (ii) all or a portion of the signaling domain of CD28, (iii) all or a portion of the signaling domain of 4-1BB, or (iv) all or a portion of the signaling domain of CD3ζ, CD28, and/or 4-1BB.

27. A stem cell or differentiated cell of embodiment 23 wherein the intracellular component includes an effector domain including a variant of CD3ζ and/or a portion of the 4-1BB intracellular signaling domain.

28. A stem cell or differentiated cell of embodiment 23 wherein the extracellular component includes a spacer region including a hinge region of human IgG4; wherein the intracellular component includes an effector domain including a cytoplasmic domain of CD28 or 4-1BB; and wherein the hydrophobic portion includes a human transmembrane domain.

29. A stem cell or differentiated cell of any of embodiments 1-28 wherein the chimeric molecule includes from amino-terminus to carboxy-terminus: a tag cassette, a hinge, and a hydrophobic portion.

30. A stem cell or differentiated cell any of embodiments 1-28 wherein the chimeric molecule includes from amino-terminus to carboxy-terminus: a first tag cassette, a second tag cassette, a hinge, and a hydrophobic portion.

31. A stem cell or differentiated cell of any of embodiments 1-28 wherein the chimeric molecule includes from amino-terminus to carboxy-terminus: a first tag cassette, a second tag cassette, a hinge, a third tag cassette, a second hinge, and a hydrophobic portion.

32. A stem cell or differentiated cell of any of embodiments 1-28 including a tag cassette located immediately amino-terminal to a spacer region, linker sequence, junction amino acid or hydrophobic portion; interposed between and connecting a spacer region, linker sequence, junction amino acid or hydrophobic portion, and/or immediately carboxy-terminal to a spacer region, linker sequence, junction amino acid or hydrophobic portion.

33. A stem cell or differentiated cell of any of embodiments 1-28 wherein the chimeric molecule includes from amino-terminus to carboxy-terminus: a tag cassette, a hinge, a hydrophobic portion, and an intracellular component including an effector domain.

34. A stem cell or differentiated cell of any of embodiments 1-28 wherein the chimeric molecule includes from amino-terminus to carboxy-terminus: two to five tag cassettes, a hinge, a hydrophobic portion, and an intracellular component including an effector domain.

35. A stem cell or differentiated cell of any of embodiments 1-28 wherein the chimeric molecule further includes a cytotoxic, radioisotope, radiometal, or detectable agent.

36. A stem cell or differentiated cell of any of embodiments 1-28 wherein the extracellular component further includes a cytotoxic, radioisotope, radiometal, or detectable agent.

37. A stem cell or differentiated cell of any of embodiments 1-36 wherein the stem cell is an embryonic stem cell.

38. A stem cell or differentiated cell of any of embodiments 1-36 wherein the differentiated cell is a cardiomyocyte, a neuron or an islet cell.

39. A composition including a pharmaceutically acceptable carrier and a genetically modified stem cell or differentiated cell of any one of embodiments 1-38.

40. A composition of embodiment 39 further including an ExoCBM that specifically binds a tag cassette expressed by the stem cell or differentiated cell within the composition.

41. A composition of embodiment 40 wherein the ExoCBM is selected from a cognate receptor, an anti-tag antibody, and/or an anti-tag scFv.

42. A composition of embodiment 39 or 40 further including an EndoCBM that specifically binds a stimulatory molecule expressed by the stem cell or differentiated cell within the composition.

43. A composition of embodiment 42 wherein the EndoCBM is selected from BDNF, bFGF, TGF-α, TGF-β, or VEGF.

44. A composition of embodiment 39 further including an ExoCBM that specifically binds a tag cassette expressed by the stem cell or differentiated cell within the composition and an EndoCBM that specifically binds a stimulatory molecule expressed by the stem cell or differentiated cell within the composition.

45. A composition of embodiment 44 wherein the ExoCBM is selected from a cognate receptor, an anti-tag antibody, and/or an anti-tag scFv.

46. A composition of embodiment 44 or 45 wherein the EndoCBM is selected from BDNF, bFGF, TGF-α, TGF-β, or VEGF.

47. A composition of any of embodiments 39-46 formulated for infusion or injection.

48. A formulation including a pharmaceutically acceptable carrier and a genetically modified stem cell or differentiated cell of any one of embodiments 1-38.

49. A formulation of embodiment 48 further including an ExoCBM that specifically binds a tag cassette expressed by the stem cell or differentiated cell within the composition.

50. A formulation of embodiment 48 or 49 wherein the ExoCBM is selected from a cognate receptor, an anti-tag antibody, and/or an anti-tag scFv.

51. A formulation of embodiment 50 further including an EndoCBM that specifically binds a stimulatory molecule expressed by the stem cell or differentiated cell within the composition.

52. A formulation of embodiment 51 wherein the EndoCBM is selected from BDNF, bFGF, TGF-α, TGF-β, or VEGF.

53. A formulation of embodiment 48 further including an ExoCBM that specifically binds a tag cassette expressed by stem cell or differentiated cell within the composition and an EndoCBM that specifically binds a stimulatory molecule expressed by the stem cell or differentiated cell within the composition.

54. A formulation of embodiment 53 wherein the ExoCBM is selected from a cognate receptor, an anti-tag antibody, and/or an anti-tag scFv.

55. A formulation of embodiment 53 or 54 wherein the EndoCBM is selected from BDNF, bFGF, TGF-α, TGF-β, or VEGF.

56. A formulation of any of embodiments 48-55 formulated for infusion or injection.

57. A method for activating a stem cell or differentiated cell of any one of embodiments 1-38 including contacting the stem cell or differentiated cell with an ExoCBM that specifically binds a tag cassette expressed by the stem cell or differentiated cell thereby activating the stem cell or differentiated cell.

58. A method of embodiment 57 further including contacting the stem cell or differentiated cell with an activating factor that specifically binds a stimulatory molecule expressed by the stem cell or differentiated cell.

59. A method of embodiment 58 wherein the activating factor is selected from Activin A, Amphiregulin, BDNF, bFGF, BMP2, BMP4, CNTF, Dkk1, EGF, IGF1, LIF, Neurotrophin-3, Neurotrophin-4, Noggin, PDGF, retinoic acid, TGF-α, TGF-β, and VEGF.

60. A method of embodiment 57 wherein the ExoCBM is a cognate receptor, an anti-tag antibody, and/or an anti-tag scFv.

61. A method of any of embodiments 57-60 wherein the tag cassette is a Strep tag having amino acid sequence SEQ ID NO:1 or SEQ ID NO:17.

62. A method of any of embodiments 57-60 wherein the ExoCBM that specifically binds the tag cassette is a biotin binding protein or an anti-Strep tag antibody.

63. A method of any of embodiments 57-62 wherein the ExoCBM is attached to a solid surface.

64. A method of any of embodiments 57-62 wherein the ExoCBM is attached to a planar surface, agarose, resin, 3D fabric matrix, or a bead.
65. A method of any of embodiments 57-62 wherein the ExoCBM is attached to a microbead or a nanobead.
66. A method of any of embodiments 57-65 wherein the activating is performed in vitro, in vivo or ex vivo.
67. A method for promoting expansion of a stem cell or differentiated cell of any one of embodiments 1-38 including contacting the stem cell or differentiated cell with (i) an ExoCBM that specifically binds a tag cassette expressed by the stem cell or differentiated cell and (ii) an activating factor that specifically binds a stimulatory molecule expressed by the stem cell or differentiated cell for a time sufficient to promote stem cell or differentiated cell expansion.
68. A method of embodiment 67 wherein the activating factor is selected from is selected from a Notch agonist, an angiopoietin-like protein, erythropoietin, fibroblast growth factor-1 (FGF-1); Flt-3 ligand (Flt-3L); granulocyte colony stimulating factor (G-CSF); granulocyte-macrophage colony stimulating factor (GM-CSF); insulin growth factor-2 (IFG-2); interleukin-3 (IL-3); interleukin-6 (IL-6); interleukin-7 (IL-7); interleukin-11 (IL-11); stem cell factor (SCF); and thrombopoietin (TPO).
69. A method of embodiment 67 or 68 wherein the ExoCBM is a cognate receptor, an anti-tag antibody, and/or an anti-tag scFv.
70. A method of any of embodiments 67-69 wherein the tag cassette is a Strep tag having amino acid sequence SEQ ID NO:1 or SEQ ID NO:17.
71. A method of any of embodiments 67-69 wherein the ExoCBM that specifically binds the tag cassette is a biotin binding protein or an anti-Strep tag antibody.
72. A method of any of embodiments 67-71 wherein the ExoCBM is attached to a solid surface.
73. A method of any of embodiments 67-71 wherein the ExoCBM is attached to a planar surface, agarose, resin, 3D fabric matrix, or a bead.
74. A method of any of embodiments 67-71 wherein the ExoCBM is attached to a microbead or a nanobead.
75. A method of any of embodiments 67-74 wherein the activating is performed in vitro, in vivo or ex vivo.
76. A method for detecting a stem cell or differentiated cell including: contacting a sample including a stem cell or differentiated cell of any one of embodiments 1-38 with an ExoCBM that specifically binds a tag cassette expressed by the stem cell or differentiated cell, wherein the ExoCBM includes a detectable moiety, and detecting the presence of the stem cell or differentiated cell in the sample based on the specific binding of the ExoCBM including the detectable moiety.
77. A method of embodiment 76 wherein the ExoCBM is a cognate receptor, an anti-tag antibody, and/or an anti-tag scFv.
78. A method of embodiment 76 or 77 wherein the tag cassette is a Strep tag having amino acid sequence SEQ ID NO:1 or SEQ ID NO:17.
79. A method of embodiment 76 or 77 wherein the ExoCBM that specifically binds the tag cassette is a biotin binding protein or an anti-Strep tag antibody.
80. A method of any of embodiments 76-79 wherein the ExoCBM is attached to a solid surface.
81. A method of any of embodiments 76-79 wherein the ExoCBM is attached to a planar surface, agarose, resin, 3D fabric matrix, or a bead.
82. A method of any of embodiments 76-79 wherein the ExoCBM is attached to a microbead or a nanobead.
83. A method of any of embodiments 76-82 wherein the detecting is performed in vitro, in vivo or ex vivo.
84. A method of any of embodiments 76-83 wherein the detectable moiety is fluorescent marker.
85. A method of any of embodiments 76-84 wherein the detectable moiety is APC, PE, Pacific blue, Alex fluor, or FITC.
86. A method of any of embodiments 76-85 wherein detection occurs using flow cytometry.
87. A method for enriching for or isolating a stem cell or differentiated cell of any of embodiments 1-38 including contacting a sample including a stem cell or differentiated cell with an ExoCBM that specifically binds a tag cassette expressed by the stem cell or differentiated cell and enriching for or isolating the stem cell or differentiated cell away from other cells not expressing the tag cassette in the sample.
88. A method of embodiment 87 wherein the ExoCBM is a cognate receptor, an anti-tag antibody, and/or an anti-tag scFv.
89. A method of embodiment 87 or 88 wherein the tag cassette is a Strep tag having amino acid sequence SEQ ID NO:1 or SEQ ID NO:17.
90. A method of embodiment 87 or 88 wherein the ExoCBM that specifically binds the tag cassette is a biotin binding protein or an anti-Strep tag antibody.
91. A method of any of embodiments 87-90 wherein the ExoCBM is attached to a solid surface.
92. A method of any of embodiments 87-90 wherein the ExoCBM is attached to a planar surface, agarose, resin, 3D fabric matrix, or a bead.
93. A method of any of embodiments 87-90 wherein the ExoCBM is attached to a microbead or a nanobead.
94. A method of any of embodiments 87-93 wherein the stem cell or differentiated cell is enriched for or isolated by magnetic column chromatography.
95. A method of any of embodiments 87-94 including detecting the enriched for or isolated stem cell or differentiated cells by contacting the stem cell or differentiated cells with an ExoCBM that specifically binds the tag cassette expressed by the enriched or isolated stem cell or differentiated cells wherein the ExoCBM includes a detectable moiety and detecting the presence of the stem cell or differentiated cells in the sample based on the specific binding of the ExoCBM including the detectable moiety.
96. A method of embodiment 95 wherein the detectable moiety is fluorescent marker.
97. A method of embodiment 95 or 96 wherein the detectable moiety is APC, PE, Pacific blue, Alex fluor, or FITC.
98. A method of any of embodiments 95-97 wherein the detection occurs using flow cytometry.
99. A method for depleting or eliminating a stem cell or differentiated cell of any of embodiments 1-38 including contacting a sample including the stem cell or differentiated cell with an ExoCBM that specifically binds a tag cassette expressed by the stem cell or differentiated cell, wherein binding of the ExoCBM to the tag cassette leads to cell death of the stem cell or differentiated cell expressing the tag cassette.
100. A method of embodiment 99 wherein the ExoCBM includes a bispecific binding domain, wherein a first binding domain is specific for the tag cassette and the second binding domain is specific for CD3.

101. A method of embodiment 99 or 100 wherein the ExoCBM includes a cytotoxic, radioisotope, or radiometal agent.

102. A method of any of embodiments 99-101 wherein the ExoCBM includes a cognate receptor, an anti-tag antibody, an anti-tag scFv, or a cell with an anti-tag binding domain on its cell surface.

103. A method of any of embodiments 99-101 wherein the tag cassette is a Strep tag having amino acid sequence SEQ ID NO:1 or SEQ ID NO:17.

104. A method of any of embodiments 99-101 wherein the ExoCBM that specifically binds the tag cassette is a biotin binding protein or an anti-Strep tag antibody.

105. A method of any of embodiments 99-104 wherein the ExoCBM is attached to a solid surface.

106. A method of any of embodiments 99-104 wherein the ExoCBM is attached to a planar surface, agarose, resin, 3D fabric matrix, or a bead.

107. A method of any of embodiments 99-104 wherein the ExoCBM is attached to a microbead or a nanobead.

108. A method of tracking administered stem cell or differentiated cell of any of embodiments 1-38 including administering to a subject an ExoCBM that specifically binds a tag cassette expressed by the stem cell or differentiated cell wherein the ExoCBM includes a detectable moiety, and detecting the presence of the stem cell or differentiated cell within the subject based on the specific binding of the ExoCBM including the detectable moiety.

109. A method of embodiment 108 wherein the stem cell or differentiated cell and the ExoCBM are administered simultaneously.

110. A method of embodiment 108 or 109 wherein stem cell or differentiated cell and the ExoCBM are administered as a composition or formulation.

111. A method of any of embodiments 108-110 wherein the ExoCBM is a cognate receptor, an anti-tag antibody, and/or an anti-tag scFv.

112. A method of any of embodiments 108-110 wherein the tag cassette is a Strep tag having amino acid sequence SEQ ID NO:1 or SEQ ID NO:17.

113. A method of any of embodiments 108-110 wherein the ExoCBM that specifically binds the tag cassette is a biotin binding protein or an anti-Strep tag antibody.

114. A method of any of embodiments 108-113 wherein the ExoCBM is attached to a solid surface.

115. A method of any of embodiments 108-113 wherein the ExoCBM is attached to a planar surface, an agarose bead, a resin, a 3D fabric matrix, or a bead.

116. A method of any of embodiments 108-113 wherein the ExoCBM is attached to a microbead or a nanobead.

117. A method of any of embodiments 108-116 wherein the detectable moiety includes a fluorescent marker.

118. A method of any of embodiments 108-117 wherein the detectable moiety includes APC, PE, Pacific blue, Alex fluor, or FITC.

119. A method of any of embodiments 108-117 wherein the detectable moiety includes a magnetic particle, superparamagnetic iron oxide (SPIO), fluorodeoxyglucose (18F), fluorescent compounds, or any combination thereof.

120. A method of any of embodiments 108-119 wherein tracking includes use of MRI, PET, or near infrared imaging.

121. A method for activating administered stem cell or differentiated cell of any of embodiments 1-38 including administering to a subject (i) an ExoCBM that specifically binds a tag cassette expressed by the stem cell or differentiated cell; (ii) an EndoCBM that specifically binds a stimulatory molecule expressed by the stem cell or differentiated cell; wherein specific binding of the ExoCBM and the EndoCBM activates the stem cell or differentiated cell in vivo.

122. A method of embodiment 121 wherein the EndoCBM is selected from BDNF, bFGF, TGF-α, TGF-β, or VEGF.

123. A method of embodiment 121 or 122 wherein the stem cell or differentiated cell, the ExoCBM, and the EndoCBM are administered simultaneously.

124. A method of any of embodiments 121-123 wherein stem cell or differentiated cell, the ExoCBM, and the EndoCBM are administered as a composition or formulation.

125. A method any of embodiments 121-123 wherein the ExoCBM is a cognate receptor, an anti-tag antibody, and/or an anti-tag scFv.

126. A method of any of embodiments 121-123 wherein the tag cassette is a Strep tag having amino acid sequence SEQ ID NO:1 or SEQ ID NO:17.

127. A method of any of embodiments 121-123 wherein the ExoCBM that specifically binds the tag cassette is a biotin binding protein or an anti-Strep tag antibody.

128. A method of depleting or eliminating administered stem cell or differentiated cell of any of embodiments 1-38 including administering an ExoCBM that specifically binds a tag cassette expressed by the administered stem cell or differentiated cell, wherein binding of the ExoCBM to the tag cassette leads to cell death of the stem cell or differentiated cell expressing the tag cassette 129. A method of embodiment 128 wherein the ExoCBM includes a bispecific binding domain, wherein a first binding domain is specific for the tag cassette and the second binding domain is specific for CD3.

130. A method of embodiment 128 or 129 wherein the ExoCBM includes a cytotoxic, radioisotope, or radiometal agent.

131. A method of any of embodiments 128-130 wherein the ExoCBM includes a cognate receptor, an anti-tag antibody, an anti-tag scFv, or a cell with an anti-tag binding domain on its cell surface.

132. A method of any of embodiments 128-130 wherein the tag cassette is a Strep tag having amino acid sequence SEQ ID NO:1 or SEQ ID NO:17.

133. A method of any of embodiments 128-130 wherein the ExoCBM that specifically binds the tag cassette is a biotin binding protein or an anti-Strep tag antibody.

134. A method of any of embodiments 128-133 wherein the ExoCBM is attached to a solid surface.

135. A method of any of embodiments 128-133 wherein the ExoCBM is attached to a planar surface, agarose, resin, 3D fabric matrix, or a bead.

136. A method of any of embodiments 128-133 wherein the ExoCBM is attached to a microbead or a nanobead.

137. A method of treating a condition in a subject, including administering a therapeutically-effective amount of a stem cell or differentiated cell of any one of embodiments 1-38, a therapeutically effective amount of a composition of any one of embodiments 39-47, or a therapeutically effective amount of a formulation of any one of embodiments 48-56 to the subject, thereby treating the condition in the subject.

138. A method of embodiment 137 further including activating, tracking or depleting or eliminating the administered stem cell or differentiated cell according to any of the methods of embodiments 108-136.

139. A kit including administering a therapeutically-effective amount of a stem cell or differentiated cell of any one of embodiments 1-38, a therapeutically effective amount of a composition of any one of embodiments 39-47, or a therapeutically effective amount of a formulation of any one of embodiments 48-56 to the subject, thereby treating the condition in the subject.

Example 1

Design and cGMP production of two third generation lentiviral vectors for the coordinate expression of a tag cassette construct will be created. A SIN vesicular stomatitis virus G (VSV-G) pseudotyped lentiviral vector will contain a hybrid 5'LTR in which the U3 region is replaced with the CMV promoter, and a 3' LTR in which the cis-acting regulatory sequences are completely removed from the U3 region. As a result, both the 5' and 3' LTRs will be inactivated when the provirus is produced and integrated into a chromosome. The vector can encode for one or more tag cassettes selected from Strep-Tag II (SEQ ID NO:1); Myc tag (SEQ ID NO:2); V5 tag (SEQ ID NO:3); Flag Tag (SEQ ID NO:4); Xpress tag (SEQ ID NO:11); Avi Tag (SEQ ID NO:12); Calmodulin Tag (SEQ ID NO:13); HA Tag (SEQ ID NO:14); Soft Tag 1 (SEQ ID NO:15); Softag 3 (SEQ ID NO:16); Strep-Tag (SEQ ID NO:17); Engineered Tag of a Minimal Chelation Site (SEQ ID NO:18); one or more linkers selected from Linker (SEQ ID NO:5); Linker (SEQ ID NO:6); Linker (SEQ ID NO:7); Linker (SEQ ID NO:10); Linker (SEQ ID NO:25); Linker (SEQ ID NO:26); Linker (SEQ ID NO:27); Linker (SEQ ID NO:28); Linker (SEQ ID NO:29); and/or one or more linker and tag combinations selected from Linker+Tag (SEQ ID NO:19); Linker+Tag (SEQ ID NO:20); Linker+Tag (SEQ ID NO:21); Linker+ Tag (SEQ ID NO:22); Linker+Tag (SEQ ID NO:23); and/or Linker+Tag (SEQ ID NO:24). The vector can also optionally encode Core Hinge Region (SEQ ID NO:8); the human GMCSFRα chain leader sequence, the Fc and hinge regions of human IgG4 heavy chain, the human CD28 transmembrane region, and/or the cytoplasmic domain of CD3ζ and CD28 or 4-1BB. The selected construct can be cloned into a modified pHIV7 in which the CMV promoter can be swapped for the human EF-1 alpha promoter. Designed vectors can allow for 1:1 expression of selected components through use of a T2A element. An N-terminal leader peptide of the human GMCSF receptor alpha chain signal sequence to direct surface expression can also be used. Particular vector examples can also encode a tag cassette that binds an endogenous cognate binding molecule.

Example 1

Umbilical cord blood/placental blood unit(s) will be collected from human(s) at birth. The collected blood will be mixed with an anti-coagulant to prevent clotting and stored. Prior to planned initiation of expansion cultures, tissue culture vessels will be first coated overnight at 4° C. or a minimum of 2 hours at 37° C. with Delta1ext-IgG at 2.5 µg/ml and RETRONECTIN® (a recombinant human fibronectin fragment) (Clontech Laboratories, Inc., Madison, Wis.) at 5 µg/ml in phosphate buffered saline (PBS). The flasks will be then washed with PBS and blocked with PBS-2% Human Serum Albumin (HSA). The fresh cord blood unit will be red cell lysed and processed to select for selected stem cells using the AUTOMACS® Cell Separation System (Miltenyi Biotec GmbH, Gladbach, Germany). After enrichment, the percentage of selected stem cells in the sample is increased relative to the percentage of the selected stem cells in the sample prior to enrichment. The enriched selected stem cell fraction will be resuspended in final culture media, to prevent differentiation.

A SIN lentiviral vector that directs the co-expression of a tag cassette, linker, or linker+tag combination provided in Example 1 will be transduced into the Notch expanded selected stem cells on day 3 or 4 via centrifugation at 800×g for 45 minutes at 32° C. with lentiviral supernatant (MOI 3) and 4 µg/ml of protamine sulfate.

At the end of the expansion culture, cells will be differentiated and tested in an animal model.

Animals will be infused via tail vein injection with the progeny generated from 10,000-30,000 cells.

Results. Transduction efficiency will range from 10 to >90%. Copy number analysis will demonstrate between 1-4 copies/cell as determined by validated real time, quantitative PCR analysis, which is in line with the FDA requirements for clinical gene therapy cell products.

As indicated, the practice of the present disclosure can employ, unless otherwise indicated, conventional methods of virology, microbiology, molecular biology and recombinant DNA techniques within the ordinary skill of the art. Such techniques are explained fully in the literature; see, e.g., Sambrook, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, vol. I & II (P. Tijessen, ed.); Fundamental Virology, 2nd Edition, vol. I & II (B. N. Fields and D. M. Knipe, eds.) each of which is incorporated by reference herein for its teachings regarding the same.

As will be understood by one of ordinary skill in the art, each embodiment disclosed herein can comprise, consist essentially of or consist of its particular stated element, step, ingredient or component. "Includes" or "including" means "comprises, consists essentially of or consists of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would result in (i) a statistically significant reduction in the effectiveness of a cell administration to create an anti-cancer effect in a subject and/or (ii) a statistically significant reduction in the effectiveness of a cell administration to re-populate a subject's immune system.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Particular embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to books, journal articles, treatises, patents, printed publications, etc. (collectively "references") throughout this specification. Each of the above-cited references are individually incorporated by reference herein for their cited teachings.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A genetically modified stem cell or differentiated cell comprising a nucleic acid encoding a chimeric molecule wherein, when expressed by the genetically modified stem cell or differentiated cell, the chimeric molecule comprises
an extracellular component and an intracellular component connected by a hydrophobic portion, wherein the extracellular component consists essentially of
two or three tag cassettes wherein at least two tag cassettes have the amino acid sequence as set forth in SEQ ID NO.: 1,
two or more linker sequences wherein at least two linker sequences have the amino acid sequence as set forth in SEQ ID NO.: 5, and
one or more spacer regions, wherein at least one spacer region comprises an Fc domain and a human IgG4 heavy chain hinge,
wherein a first tag cassette and a second tag cassette having the amino acid sequence as set forth in SEQ ID NO.: 1 are each adjacent to at least one linker sequence having the amino acid sequence as set forth in SEQ ID NO.: 5,
wherein the chimeric molecule includes from amino-terminus to carboxy-terminus: (i) the first tag cassette having the amino acid sequence as set forth in SEQ ID NO.: 1 adjacent to the at least one linker sequence having the amino acid sequence as set forth in SEQ ID NO.: 5, (ii) the second tag cassette having the amino acid sequence as set forth in SEQ ID NO.: 1 adjacent to a linker sequence having the amino acid sequence as set forth in SEQ ID NO.: 5, (iii) the at least one spacer region, and (iv) the hydrophobic portion.

2. The genetically modified stem cell or differentiated cell of claim 1, wherein the differentiated cell is a cardiomyocyte, a neuron, an oligodendrocyte, an insulin producing beta cell, or a retinal cell.

3. The genetically modified stem cell or differentiated cell of claim 1, wherein the first tag cassette having the amino acid sequence as set forth in SEQ ID NO.: 1 and the adjacent at least one linker sequence having the amino acid sequence as set forth in SEQ ID NO.: 5 are within an amino acid sequence as set forth in SEQ ID NO.: 19, SEQ ID NO.: 20, SEQ ID NO.: 21, SEQ ID NO.: 22, SEQ ID NO.: 23, or SEQ ID NO.: 24.

4. The genetically modified stem cell or differentiated cell of claim 1, wherein the hydrophobic portion comprises a human transmembrane domain.

5. The genetically modified stem cell or differentiated cell of claim 1, wherein the chimeric molecule consists essentially of from amino-terminus to carboxy-terminus: (i) the first tag cassette having the amino acid sequence as set forth in SEQ ID NO.: 1 adjacent to the at least one linker sequence having the amino acid sequence as set forth in SEQ ID NO.:5, (ii) the second tag cassette having the amino acid sequence as set forth in SEQ ID NO.: 1 adjacent to a linker sequence having the amino acid sequence as set forth in SEQ ID NO.:5, (iii) the at least one spacer region, and (iv) the hydrophobic portion.

6. The genetically modified stem cell or differentiated cell of claim 1, wherein the hydrophobic portion comprises a CD28 transmembrane domain, a CD4 transmembrane domain, a CD8 transmembrane domain, or a CD27 transmembrane domain.

7. The genetically modified stem cell or differentiated cell of claim 1, wherein the hydrophobic portion comprises a human transmembrane domain.

8. The genetically modified stem cell or differentiated cell of claim 1, formulated for administration to a subject.

9. The genetically modified stem cell or differentiated cell of claim 2, wherein the neuron is a motor neuron, a dopaminergic neuron, a glutamatergic neuron, or a GABAergic neuron.

10. The genetically modified stem cell or differentiated cell of claim 1, wherein the intracellular component comprises an intracellular signaling domain.

11. A genetically modified stem cell or differentiated cell comprising a nucleic acid encoding a chimeric molecule wherein, when expressed by the genetically modified stem cell or differentiated cell, the chimeric molecule comprises
an extracellular component and an intracellular component connected by a hydrophobic portion, wherein the extracellular components consists essentially of
a first tag cassette, a second tag cassette, and a third tag cassette each having the amino acid sequence as set forth in SEQ ID NO.: 1,
three or more linker sequences wherein at least three linker sequences have the amino acid sequence as set forth in SEQ ID NO.: 5, and
two or more spacer regions, wherein at least one spacer region comprises an Fc domain and a human IgG4 heavy chain hinge, and
wherein the first tag cassette, the second tag cassette and the third tag cassette having the amino acid sequence as set forth in SEQ ID NO.: 1 are each adjacent to at least one linker sequence having the amino acid sequence as set forth in SEQ ID NO.: 5,
wherein the chimeric molecule includes from amino-terminus to carboxy-terminus: (i) the first tag cassette having the amino acid sequence as set forth in SEQ ID NO.: 1 adjacent to the at least one linker sequence having the amino acid sequence as set forth in SEQ ID NO.: 5, (ii) the second tag cassette having the amino acid sequence as set forth in SEQ ID NO.: 1 adjacent to a linker sequence having the amino acid sequence as set forth in SEQ ID NO.: 5, (iii) the at least one spacer region, wherein the at least one spacer region is a first spacer region, (iv) the third tag cassette having the amino acid sequence as set forth in SEQ ID NO.: 1 adjacent to a linker sequence having the amino acid sequence as set forth in SEQ ID NO.: 5, (v) a second spacer region comprising an Fc domain and a human IgG4 heavy chain hinge, and (vi) the hydrophobic portion.

12. A genetically modified stem cell or differentiated cell comprising a nucleic acid encoding a chimeric molecule wherein, when expressed by the genetically modified stem cell or differentiated cell, the chimeric molecule comprises
an extracellular component linked to a hydrophobic portion, wherein the extracellular component consists essentially of one or more tag cassettes wherein at least one tag cassette has the amino acid sequence set as forth in SEQ ID NO.: 1,
one or more linker sequences wherein at least one linker sequence has the amino acid sequence as set forth in SEQ ID NO.: 5, and
one or more spacer regions, wherein at least one spacer region comprises an Fc domain and a human IgG4 heavy chain hinge, and
wherein the at least one tag cassette having the amino acid sequence as set forth in SEQ ID NO.: 1 is adjacent to the at least one linker sequence having the amino acid sequence as set forth in SEQ ID NO.: 5,
wherein the hydrophobic portion links the extracellular component to an intracellular component, and
wherein the chimeric molecule includes from amino-terminus to carboxy-terminus: (i) the at least one tag cassette having the amino acid sequence as set forth in SEQ ID NO.: 1 adjacent to the at least one linker sequence having the amino acid sequence as set forth in SEQ ID NO.: 5, (ii) the at least one spacer region, (iii) the hydrophobic portion; and (iv) the intracellular component.

13. The genetically modified stem cell or differentiated cell of claim 12, wherein the first tag cassette having the amino acid sequence as set forth in SEQ ID NO.: 1 and the adjacent at least one linker sequence having the amino acid sequence as set forth in SEQ ID NO.: 5 are within an amino acid sequence as set forth in SEQ ID NO.: 19, SEQ ID NO.: 20, SEQ ID NO.: 21, SEQ ID NO.: 22, SEQ ID NO.: 23, or SEQ ID NO.: 24.

14. The genetically modified stem cell or differentiated cell of claim 12, wherein the differentiated cell is a cardiomyocyte, a neuron, an oligodendrocyte, an insulin producing beta cell, a retinal cell, a myeloid progenitor, or a lymphoid progenitor.

15. The genetically modified stem cell or differentiated cell of claim 14, wherein the neuron is a motor neuron, a dopaminergic neuron, a glutamatergic neuron, or a GABAergic neuron.

16. The genetically modified stem cell or differentiated cell of claim 12, wherein the hydrophobic portion comprises a CD28 transmembrane domain, a CD4 transmembrane domain, a CD8 transmembrane domain, or a CD27 transmembrane domain.

17. The genetically modified stem cell or differentiated cell of claim 12, formulated for administration to a subject.

* * * * *